US011060064B2

(12) United States Patent
Gerecht et al.

(10) Patent No.: US 11,060,064 B2
(45) Date of Patent: Jul. 13, 2021

(54) EARLY VASCULAR CELL POPULATION

(71) Applicant: THE JOHNS HOPKINS UNIVERSITY, Baltimore, MD (US)

(72) Inventors: Sharon Gerecht, Severna Park, MD (US); Sravanti Kusuma, Chicago, IL (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 16/000,289

(22) Filed: Jun. 5, 2018

(65) Prior Publication Data

US 2018/0298329 A1    Oct. 18, 2018

Related U.S. Application Data

(60) Division of application No. 14/777,258, filed as application No. PCT/US2014/030708 on Mar. 17, 2014, now Pat. No. 9,994,825, which is a continuation-in-part of application No. 13/844,313, filed on Mar. 15, 2013, now Pat. No. 9,506,037.

(60) Provisional application No. 61/846,369, filed on Jul. 15, 2013.

(51) Int. Cl.
| | |
|---|---|
| *C12N 5/02* | (2006.01) |
| *C12N 5/071* | (2010.01) |
| *A61K 38/39* | (2006.01) |
| *A61K 31/00* | (2006.01) |

(52) U.S. Cl.
CPC .......... *C12N 5/069* (2013.01); *C12N 5/0691* (2013.01); *A61K 31/00* (2013.01); *A61K 38/39* (2013.01); *C12N 5/0692* (2013.01); *C12N 2501/15* (2013.01); *C12N 2501/165* (2013.01); *C12N 2501/17* (2013.01); *C12N 2501/42* (2013.01); *C12N 2501/905* (2013.01); *C12N 2501/998* (2013.01); *C12N 2506/02* (2013.01); *C12N 2506/03* (2013.01); *C12N 2506/45* (2013.01); *C12N 2533/54* (2013.01); *C12N 2533/80* (2013.01)

(58) Field of Classification Search
CPC ........................... C12N 5/0691; C12N 5/0692; C12N 2506/02; C12N 2506/45
See application file for complete search history.

(56) References Cited

U.S. PATENT DOCUMENTS

| | | | | |
|---|---|---|---|---|
| 9,533,073 | B1 * | 1/2017 | Kong .................. | A61F 2/062 |
| 2005/0112106 | A1 | 5/2005 | Gerecht-Nir et al. | |
| 2009/0123430 | A1 | 5/2009 | DeSousa | |
| 2010/0216181 | A1 | 8/2010 | Daigh et al. | |
| 2010/0279403 | A1 | 11/2010 | Rajesh et al. | |
| 2011/0305672 | A1 | 12/2011 | Dalton et al. | |
| 2012/0015395 | A1 | 1/2012 | Shusta et al. | |
| 2012/0148546 | A1 | 6/2012 | Dar-Oaknin et al. | |
| 2012/0295347 | A1 | 11/2012 | Kessler | |

FOREIGN PATENT DOCUMENTS

| | | |
|---|---|---|
| EP | 2277993 A1 | 1/2011 |
| WO | 03/010303 A1 | 2/2003 |
| WO | 2010/099539 A1 | 9/2010 |
| WO | 2011/021194 A2 | 2/2011 |
| WO | 2011/090684 A2 | 7/2011 |
| WO | 2011/106681 A2 | 9/2011 |
| WO | 2012/006440 A2 | 1/2012 |
| WO | 2012/168167 A1 | 12/2012 |

OTHER PUBLICATIONS

Ingram et al., 2004, Blood, vol. 104, No. 9, p. 2752-2760.*
Nakao et al., 2008, US 20080025955 A1.*
Kusuma et al., "Self-organized vascular networks from human pluripotent stem cells in a synthetic matrix," PNAS, Jul. 2013, vol. 110, pp. 12601-12606.
Kusuma et al., (2012). The extracellular matrix is a novel attribute of endothelial progenitors and of hypoxic mature endothelial cells. The FASEB Journal. 4925-4936.
Lee et al., "Motion correction for phase-resolved dynamic optical coherence tomography imaging of rodent cerebral cortex," Biomed. Opt. Express 19(22), 21258-21270 (2012).
Lee et al., (2010). Derivation of neural crest cells from human pluripotent stem cells. Nat Protocols 5, 688-701.
Lee TH, Song SH, Kim KL, Yi JY, Shin GH, Kim JY et al. Functional Recapitulation of Smooth Muscle Cells Via Induced Pluripotent Stem Cells From Human Aortic Smooth Muscle Cells. Circ Res 2010;106:120-128.
Leitgeb et al., "Ultrahigh resolution Fourier domain optical coherence tomography," Opt. Express 12(10), 2156-2165(2004).
Levenberg S, et al. Endothelial cells derived from human embryonic stem cells PNAS USA, 2002, vol. 99, pp. 4391-4396.
Levenberg S., et al., Blood, 110, 805-814 (2007).
Lindskog et al. "New insights to vascular smooth muscle cell and pericyte differentiation of mouse embryonic stem cells in vitro" Arterioscler Thromb Vasc Biol, 2006, vol. 26, pp. 1457-1464.
Liu et al., "Distortion-free freehand-scanning OCT implemented with real-time scanning speed variance correction," Opt. Express 20(15), 16567-16583 (2012).
Lombardi MAR DM, Schwartz SM. Methodologic considerations important in the accurate quantitation of aortic smooth muscle cell replication in the normal rat. Am J Pathol. 1991;138:441-446.
Maguluri et al., "Three dimensional tracking for volumetric spectral-domain optical coherence tomography," Opt. Express 15(25), 16808-16817 ( 2007).
Mali et al, Butyrate Greatly Enhances Derivation of Human Induced Pluripotent Stem Cells by Promoting Epigenetic Remodeling and the Expression of Pluripotency-Associated Genes. Stem Cells, 28, 713-720 (2010).

(Continued)

Primary Examiner — Shin Lin Chen
(74) Attorney, Agent, or Firm — Venable LLP; Keith G. Haddaway; Miguel A. Lopez

(57) ABSTRACT

The present invention relates to the area of in vitro cell populations useful for generating vascular networks in vitro and are suitable for use in vivo for regeneration of vascular tissue. In some embodiments, the bipotent cell population of the present invention comprise endothelial cells and pericytes that express vascular endothelial cadherin and are 95% or more positive for CD105 and CD146, and which work syergistically to recreate vascular tissues in vitro.

7 Claims, 41 Drawing Sheets

(56) References Cited

OTHER PUBLICATIONS

Mead LE et al. "Isolation and characterization of endothelial progenitor cells from human blood" Current protocols in stem cell biology, 2008, Chapter 2.
Melero-Martin JM et al. "Engineering robust and functional vascular networks in vivo with human adult and cord blood-derived progenitor cells", Circulation Research, 2008, vol. 103, pp. 194-202.
Mulvany MJ, Aalkjaer C. Structure and function of small arteries. Physiol Rev 1990;70:921-961.
Narazaki Get al. "Directed and systematic differentiation of cardiovascular cells from mouse induced pluripotent stem cells" Circulation, 2008, vol. 118, pp. 498-506.
Nishikawa et al. "Progressive lineage analysis by cell sorting and culture identifies FLK1=VEcadherin+ cells at a diverging point of endothelial and hemopoietic lineages." Development, 125, 1747-1757 (1998).
Nourse et al., "VEGF Induces Differentiation of Functional Endothelium From Human Embryonic Stem Cells", Cell Biology/Signaling, vol. 30, pp. 80-89. (2009).
Orlidge et al., (1987). Inhibition of capillary endothelial cell growth by pericytes and smooth muscle cells. The Journal of Cell Biology 105, 1455-1462.
Owens GK, Kumar MS, Wamhoff BR. Molecular Regulation of Vascular Smooth Muscle Cell Differentiation in Development and Disease. Physiol Rev 2004;84:767-801.
Oyamada N, Itoh H, Sone M, Yamahara K, Miyashita K, Park K et al. Transplantation of vascular cells derived from human embryonic stem cells contributes to vascular regeneration after stroke in mice. J Transl Med. 2008;6:54.
Park et al., (2010). Efficient differentiation of human pluripotent stem cells into functional CD34+ progenitor cells by combined modulation of the MEK/ERK and BMP4 signaling pathways. Blood 116, 5762-5772.
Parmacek, MS. Transcriptional programs regulating vascular smooth muscle cell development and differentiation. Curr Top Dev Biol vol. vol. 51: Academic Press:69-89.
Patel A, Fine B, Sandig M, Mequanint K. Elastin biosynthesis: The missing link in tissueengineered blood vessels. Cardiovasc Res 2006;71:40-49.
Peerani et al. "Niche-mediated Control of Human Embryonic Stem Cell self-renewal and Differentiation." The EMBO Jounal (2007) 26, 4744-4755.
Pertoft, H. "Fractionation of cells and subcellular particles with Percoll", J. Bioochem Biophys Methods, 2000; vol. 44, pp. 1-30.
Phelps et al., Update on therapeutic vascularization strategies. Regen Med 2009;4:65-80.
Pittenger et al., (1999). Multilineage potential of adult human mesenchymal stem cells. Science 284, 143-147.
Potsaid et al., "Ultrahigh speed Spectral / Fourier domain OCT ophthalmic imaging at 70,000 to 312,500 axial scans per second," Opt. Express, vol. 16, pp. 15149-15169, 2008.
Potta SP et al. "Functional characterization and transcriptome analysis of embryonic stem cell derived contractile smooth muscle cells" Hypertension, 2009, vol. 53, pp. 196-204.
Prater DN, et al. "Working hypothesis to redefine endothelial progenitor cells" Leukemia, 2007, vol. 21, pp. 1141-1149.
Rensen SSM, et al. "Regulation and characteristics of vascular smooth muscle cell phenotypic diversity" Netherlands Hear Journal, 2007, vol. 15, pp. 100-108.
Reubinoff et. al. "Embryonic stem cell lines from human blastocysts: somatic differentiation in vitro," Nature Biotechnology, 2000, vol. 18, No. 4, pp. 399-404.
Rodriguez et al. "Clonogenic multi potent stem cells in human adipose tissue differentiate into functional smooth muscle cells". PNAS USA, 2006, vol. 103, pp. 12167-12172.
Sainson et al., (2008). Regulation of angiogenesis by homotypic and heterotypic notch signalling in endothelial cells and pericytes: from basic research to potential therapies. Angiogenesis 11, 41-51.
Sato et al., "Molecular signature of human embryonic stem cells and its comparison with the house," Developmental Biology, 2003, vol. 260, pp. 404-413.
Schenke-Layland K, Rhodes KE, Angelis E, Butylkova Y, Heydarkhan-Hagvall S, Gekas C et al. Reprogrammed Mouse Fibroblasts Differentiate into Cells of the Cardiovascular and Hematopoietic Lineages. Stem cells 2008;26:1537-1546.
Seifert et al., "Vasculogeneic maturation of E14 embryonic stem cells with evidence of early vascular endothelial growth factor independency," Differentiation, 2008, vol. 76, pp. 857-867.
Shah NM et al. "Alternative neural crest cells fates are instructively promoted by TGD-Beta superfamily members" Cell, 1996, vol. 85, pp. 331-343.
Shuldiner, M et al. "Effects of eight growth factors on the differentiation of cells derived from human embryonic stem cells", 2000, PNAS USA, vol. 97, pp. 11307-11312.
Singh et al., "Physiological tremor during retinal microsurgery," Proc. 28th Annual Conf. IEEE Eng. Med. Bio. Soc.,171-172(2002).
Sinha S et al. "Assessment of contractility of purified smooth muscle cells derived from embryonic stem cells" Stem Cells, 2006, vol. 24, pp. 1678-1688.
Sinha S, Hoofnagle MH, Kingston PA, McCanna ME, Owens GK. Transforming growth factorbeta1 signaling contributes to development of smooth muscle cells from embryonic stem cells. Am J Physiol Cell Physiol. 2004;287:C1560-1568.
Sobue K, Hayashi K, Nishida W, Expressional regulation of smooth muscle cell-specific genes in association with phenotypic modulation. Molecular and Cellular Biochemistry 1999;190:105-18.
Solan A et al. "Age effects on Vascular Smooth muscle: An engineered tissue approach" Cell Transplantation, 2005, vol. 14, pp. 481-488.
Sone et al. "Different differentiation kinetics of vascular progenitor cells in primate and mouse embryonic stem cells" Circulation, 2003, vol. 107, pp. 2085-2088.
Sone et al. "Pathway for Differentiation of Human Embryonic Stem Cells to Vascular Cell Components and Their Potential for Vascular Regeneration", Arterioscler Thromb. Vasco Biol., 2007, vol. 27, pp. 2127-2134.
Song et al., "Active tremor cancellation by a "Smart" handheld vitreoretinal microsurgical tool using swept source optical coherence tomography," Opt. Express 20, 23414-23421 (2012).
Stewart et al. "Deconstructing Human Embryonic Stem Cell Cultures: Niche Regulation of Self-Renewal and Pluripotency." J. Mol. Med. (2008) 86:875-86.
Extended European search report dated Jul. 26, 2016 for EP application 14763516.3.
Crisan, M., et al., "Perivascular cells for regenerative medicine", Journal of Cellular and Molecular Medicine, vol. 16, No. 12, pp. 2851-2860, Dec. 1, 2012.
Dar, A., et al., "Multipotent vasculogenic pericytes from human pluripotent stem cells promote recovery of murine ischemic limb", Circulation, vol. 125, No. 1, pp. 87-99, Jan. 3, 2012.
Hanjaya-Putra, D., et al., "Controlled activation of morphogenesis to generate a functional human microvasculature in a synthetic matrix", Blood, vol. 118, No. 3, pp. 804-815, Apr. 28, 2011.
James, D., et al., "Expansion and maintenance of human embryonic stem cell-derived endothelial cells by TGF[beta] inhibition is ld1 dependent", Nature Biotechnology, vol. 28, No. 2, pp. 161-166, Feb. 1, 2010.
Kusuma, S., et al., "Self-organized vascular networks from human pluripotent stem cells in a synthetic matrix", PNAS, vol. 110, No. 31, pp. 12601-12606, Jul. 15, 2013.
Nonaka, H., et al., "Development of stabilin2+ endothelial cells from mouse embryonic stem cells by inhibition of TGF[beta]/activin signaling", Biochemical and Biophysical Research Communications, Academic Press Inc. Orlando, FL, US, vol. 375, No. 2, pp. 256-260, Oct. 17, 2008.
Abaci et al., (2011). Unforeseen decreases in dissolved oxygen levels affect tube formation kinetics in collagen gels. American Journal of Physiology—Cell Physiology 301, C431-C440.
Abeyta et al., "Unique gene expression signatures of independently-derived human embryonic stem cell lines," Human Molecular Genetics, 2004, vol. 13, pp. 601-608.

(56) References Cited

OTHER PUBLICATIONS

Ahmad et al., "Cross-correlation-based image acquisition technique for manually-scanned optical coherence tomography," Opt. Express 17(10), 8125-8136 (2009).
Aikawa et al. (1993) "Human smooth muscle myosin heavy chain isoforms as molecular markers for vascular development and atherosclerosis" Circ Res 107,2085-8.
Airas et al., (1995). CD73 is involved in lymphocyte binding to the endothelium: characterization of lymphocyte-vascular adhesion protein 2 identifies it as CD73. The Journal of Experimental Medicine 182, 1603-1608.
Allegrucci et al., "Differences between human embryonic stem cell lines," Human Reproduction Update, vol. Advance Access, 2006, pp. 1-18.
Au P et al. "Bone marrow derived mesenchymal stem cells facilitate engineering of long-lasting functional vasculature", Blood, 2008, vol. 111, pp. 4551-4558.
Au P et al. "Differential in vivo potential of endothelial progenitor cells from human umbilical cord blood and adult peripheral blood to form functional long-lasting vessels" Blood, 2007, vol. 111, pp. 1302-1305.
Ball SG, Shuttleworth CA, Kielty CM. Platelet-derived growth factor receptors regulate mesenchymal stem cell fate: implications for neovascularization. Expert Opin Biol Ther 2010;10:57-71.
Bardin et al., (2001). Identification of CD146 as a component of the endothelial junction involved in the control of cell-cell cohesion. Blood 98, 3677-3684.
Beamish JA HP, Kottke-Marchant K, Marchant RE. Molecular regulation of contractile smooth muscle cell phenotype: implications for vascular tissue engineering. Tissue Eng Part B Rev. 2010;16:467-491.
Becker et al., "State estimation and feedforward tremor suppression for a handheld micromanipulator with a Kalman filter," IEEE/RSJ, International Conference on Intelligent Robots and Systems, 5160-6165(2011).
Bertolino P, Deckers M, Lebrin F, ten Dijke P. Transforming Growth Factor-β Signal Transduction in Angiogenesis and Vascular Disorders. Chest 2005;128:585S-590S.
Bettinger et al. "Enhancement of In Vitro Capillary Tube Formation by Substrate Nanotopography", Adv. Mater, 2008, vol. 20, pp. 99-103.
Ferreira et al. "Vascular progenitor cells isolated from human embryonic stem cells give rise to endothelial and smooth muscle like cells and form vascular networks in vivo", Circ. Res., 2007, vol. 101, pp. 286-294.
Boppart et al., "Forward-imaging instruments for optical coherence tomography, " Opt. Lett. 22(21), 1618-1620 (1997).
Boppart et al., "Intraoperative assessment of microsurgery with three-dimensional optical coherence tomography," Radiology, vol. 208, pp. 81-86, 1998.
Boppart et al., "Optical coherence tomography: feasibility for basic research and image-guided surgery of breast cancer," Breast Cancer Res. Treatment 84(2), 85-97(2004).
Carmeliet P. "Mechanisms of Angiogenesis and Arteriogenesis", Nat. Med, 2000, vol. 6, pp. 389-395.
Carmeliet, P. "Angiogenesis in health and disease" Nature Medicine, 2003, vol. 9, pp. 653-660.
Caspi et al. "Tissue engineering of vascularized cardiac muscle from human embryonic stem cells" Circ Res, 2007, vol. 100, pp. 263-272.
Cecchettini A, Rocchiccioli S, Boccardi C, Citti L. Chapter Two—Vascular Smooth-Muscle-Cell Activation: Proteomics Point of View. In: Kwang WJ, ed. International Review of Cell and Molecular Biology. vol. vol. 288: Academic Press; 2011:43-99.
Chan-Park MB, Shen JY, Cao Y, Xiong Y, Liu Y, Rayatpisheh S et al. Biomimetic control of vascular smooth muscle cell morphology and phenotype for functional tissue-engineered smalldiameter blood vessels. J Biomed Mater Res A 2009;88A:1104-1121.

Chen et al., "Noninvasive imaging of in vivo blood flow velocity using optical Doppler tomography," Opt. Lett. 22(14), 1119-1121(1997).
Chen J, Kitchen CM, Streb JW, Miano JM. Myocardin: a component of a molecular switch for smooth muscle differentiation. J Mol Cell Cardiol. 2002;34:1345-1356.
Chen S et al. "Transforming growth factor-beta-induced differentiation of smooth muscle from a neural crest stem cell line", Circulation Research, 2004, vol. 94, pp. 1195-1202.
Cheng L, Hansen NF, Zhao L, Du Y, Zou C, Donovan FX et al. Low incidence of DNA sequence variation in human induced pluripotent stem cells generated by nonintegrating plasmid expression. Cell Stem Cell 2012;10:337-344.
Chou et al., (2011). Efficient human iPS cell derivation by a non-integrating plasmid from blood cells with unique epigenetic and gene expression signatures. Cell Research 21, 518-529.
Crisan et al., (2008). A Perivascular Origin for Mesenchymal Stem Cells in Multiple Human Organs. Cell Stem Cell 3, 301-313.
Crisan et al., (2012). Perivascular cells for regenerative medicine. Journal of Cellular and Molecular Medicine, 2851-2860.
Dar et al., (2011). Multipotent Vasculogenic Pericytes From Human Pluripotent Stem Cells Promote Recovery of Murine Ischennic Limb / Clinical Perspective. Circulation 125, 87-99.
Darland DC, D'Amore PA. TGFP is required for the formation of capillary-like structures in threedimensional cocultures of 10I1/2 and endothelial cells. Angiogenesis 2001;4;11-20.
Dempsey EC, Badesch DB, Dobyns EL, Stenmark KR. Enhanced growth capacity of neonatal pulmonary artery smooth muscle cells in vitro: Dependence on cell size, time from birth, insulinlike growth factor I, and auto-activation of protein Kinase C. J Cell Physiol 1994;160:469-481.
Dickinson et al., (2010). Guiding endothelial progenitor cell tube formation using patterned fibronectin surfaces. Soft Matter 6, 5109-5119.
Ding R et al. "Endothelial-mesenchymal interactions in vitro reveal molecular mechanisms of smooth muscle/pericyte differentiation" Stem Cells and Development, 2004, vol. 13, pp. 509-520.
Dingemans KP, Teeling P, Lagendijk JH, Becker AE. Extracellular matrix of the human aortic media: An ultrastructural histochemical and immunohistochemical study of the adult aortic media. Anat Rec 2000;258:1-14.
Discher et al., (2009). Growth Factors, Matrices, and Forces Combine and Control Stem Cells. Science 324, 1673-1677.
Doi et al., "Notch signaling regulates the differentiation of bone marrow-derived cells into smooth muscle-like cells during arterial lesion formation" Biochemical and Biophysical Communications, vol. 381, pp. 654-659 (Feb. 27, 2009).
Drukker et al., (2012). Isolation of primitive endoderm, mesoderm, vascular endothelial and trophoblast progenitors from human pluripotent stem cells. Nature Biotechnology 30, 531-542.
Duband et al. "Calponin and SM 22 as differentiation markers of smooth muscle: spatiotemporal distribution during avian embryonic development", Differentiation, 1993, vol. 55, pp. 1-11.
Duff et al., (2003). CD105 is important for angiogenesis: Evidence and potential applications. FASEB Journal 17, 984-992.
Duncan et al., "Processing algorithms for tracking speckle shifts in optical elastography of biological tissues," J. Biomed. Opt. 6(4), 418-426(2001).
Folkman J et al. "Long-term culture of capillary endothelial cells", PNAS USA, 1979, vol. 76, pp. 5217-5221.
Ford et al., "PKH26 and 125I-PKH95: characterization and efficacy as labels for in vitro and in vivo endothelial cell localization and tracking," J. Surg. Res, vol. 62, pp. 23-28. (1996).
Freshney, R. Ian (Culture of Animal Cells: A manual of Basic Techniques and Specialized Applications, 6th ed. Wiley Blackwell, 2011. pp. 163-186.
Gaengel K, Genove G, Armulik A, Betsholtz C. Endothelial-Mural Cell Signaling in Vascular Development and Angiogenesis. Arterioscler Thromb Vasc Biol 2009;29:630-638.
Gerecht-Nir et al. "Human Embryonic Stem Cells as an In Vitro Model for Human Vascular Development and the Induction of Vascular Differentiation", Laboratory Investigation, 2003, vol. 83, pp. 1811-1820.

(56) References Cited

OTHER PUBLICATIONS

Gerecht-Nir et al., "Vascular Development in Early Human Embryos and in Teratomas Derived from Human Embryonic Stem Cells," Biology of Reproduction, 2004, vol. 71, pp. 2029-2036.

Gong et al. "Small-diameter human vessel wall engineered from bone marrow-derived mesenchymal stem cells (hMSCs)", FASEB Journal, 2008, vol. 22, pp. 1635-1648.

Gong Z et al. "Influence of culture medium on smooth muscle cell differentiation from human bone marrow-derived mesenchymal stem cells" Tissue Engineering—Part A, 2009, vol. 15, pp. 319-330.

Grainger D, Metcalfe J, Grace A, Mosedale D. Transforming growth factor-beta dynamically regulates vascular smooth muscle differentiation in vivo. J Cell Sci 1998;111:2977-2988.

Grayson et al., (2010). Engineering anatomically shaped human bone grafts. Proceedings of the National Academy of Sciences of the United States of America 107, 3299-3304.

Ha et al., "Compensation of motion artifacts in catheter-based optical frequency domain imaging," Opt. Express 18(11), 11418-11427 (2010).

Haase et al., (2009). Generation of Induced Pluripotent Stem Cells from Human Cord Blood. Cell Stem Cell 5, 434-441.

Han et al., "Handheld forward-imaging needle endoscope for ophthalmic optical coherence tomography inspection," J. Biomed. Opt. 13(2), 020505(2008).

Hanjaya-Putra et al. "Vascular endothelial growth factor and substrate mechanics regulate in vitro tubulogenesis of endothelial progenitor cells", J Cell Mol Med, 2009, vol. 14, No. 10, pp. 2436-2447.

Hanjaya-Putra et al., (2011). Controlled activation of morphogenesis to generate a functional human microvasculature in a synthetic matrix. Blood 118, 804-815.

Hashemi et al., "The promotion of stemness and pluripotency following feeder-free culture of embryonic stem cells on collagen-grafted 3-dimensional nanofibrous scaffold," Biomaterials, vol. 32, No. 30, 2011, pp. 7363-7374.

Hellstrom M, Kal n M, Lindahl P, Abramsson A, Betsholtz C. Role of PDGF-B and PDGFR-beta in recruitment of vascular smooth muscle cells and pericytes during embryonic blood vessel formation in the mouse. Development 1999;126:3047-3055.

Hill et al., "Human Embryonic Stem Cell Derived Vascular Progenitor Cells Capable of Endothelial and Smooth Muscle Cell Function", Experimental Hematology, vol. 38, No. 3, pp. 246-257. (2010).

Hirschi KK et al. Smooth Muscle Stem Cells:, Anatomical Record-Par A Discoveries in Molecular, Cellular, and Evolutionary Biology, 2004, vol. 276, pp. 22-33.

Hirschi KK et. al. "PDGF, TGF-β, and Heterotypic Cell-Cell Interactions Mediate Endothelial Cellinduced Recruitment of 10T1/2 Cells and Their Differentiation to a Smooth Muscle Fate", Journal of Cell Biology, 1998, vol. 252, pp. 805-814.

Hirschi KK, et al. "Assessing Identity, phenotype, and fate of endothelial progenitor cells", Arteriosclerosis, Thrombosis, and Vascular Biology, 2008, vol. 28, pp. 1584-1595.

Hirschi KK, et al. "Pericytes in the microvasculature" Cardiovascular Research, 1996, vol. 32, pp. 687-698.

Hofmann et al., (2007). Notch Signaling in Blood Vessels: Who Is Talking to Whom About What? Circulation Research 100, 1556-1568.

Hoofnagle MH, Neppl RL, Berzin EL, Teg Pipes GC, Olson EN, Wamhoff BW et al. Myocardin is differentially required for the development of smooth muscle cells and cardiomyocytes. Am J Physiol Heart Circ Physiol 2011;300:H1707-1712.

Huang et al., "Motion compensated fiber-optic confocal microscope based on a common-path optical coherence tomography distance sensor, " Opt. Eng. 50(8), 083201 (2011).

Huang et al., "Noncontact common-path Fourier domain optical coherence tomography method for in vitro intraocular lens power measurement", J. Biomed. Opt. 16(12), 126005(2011).

Huang et al., "Optical coherence tomography," Science, 254(5035), 1178-1181(1991).

Huang et al., "Real-time 3D and 4D Fourier domain Doppler optical coherence tomography based on dual graphics processing units," Biomed. Opt. Express 3(9), 2162-2174 ( 2012).

Huang et al., Differentiation of human embryonic stem cells into smooth muscle cells in adherent monolayer culture. Biochem Biophys Res Commun 2006;351:321-327.

Huo et al., "Forward-viewing resonant fiber-optic scanning endoscope of appropriate scanning speed for 3D OCT imaging," Opt. Express 18(14),14375-14384(2010).

Iftimia et al., "Adaptive ranging for optical coherence tomography," Opt. Express 12(17), 4025-4034 (2004).

Ingram et al. "Identification of a novel hierarchy of endothelial progenitor cells using human peripheral and umbilical cord blood" Blood, 2004, vol. 104, pp. 2752-2760.

Izzard TD, Taylor C, Birkett SD, Jackson CL, Newby AC. Mechanisms underlying maintenance of smooth muscle cell quiescence in rat aorta: role of the cyclin dependent kinases and their inhibitors. Cardiovasc Res 2002;53:242-252.

Jafri et al., "Optical coherence tomography guided neurosurgical procedures in small rodents," J. Neurosci. Methods 176(2), 85-89 (2009).

Jain RK. "Molecular regulation of vessel maturation", Nature Medicine, 2003, vol. 9, pp. 685-693.

James D et al. "Expansion and maintenance of human embryonic stem cell-derived endothelial cells by TGF (beta) inhibition is ldl dependent" Nat Biotech, 2010, vol. 28, pp. 161-166.

Jin S, Hansson EM, Tikka S, Lanner F, Sahlgren C, Farnebo F et al. Notch signaling regulates platelet-derived growth factor receptor-beta expression in vascular smooth muscle cell. Circ Res 2008;102:1483-1491.

Jung et al., "Three-dimensional optical coherence tomography employing a 2-axis microelectromechanical scanning mirror," IEEE J. Sel. Top. Quantum Electron. 11(4), 806-810(2005).

Kang et al., "Endoscopic functional Fourier domain common path optical coherence tomography for microsurgery," IEEE J. Sel. Top. Quantum Electron. 16(4), 781-792(2010).

Kang et al., "Real-time three-dimensional Fourier-domain optical coherence tomography video image guided microsurgeries," J. Biomed. Opt. 17(8), 081403 (2012).

Kang et al., (2011). Bioengineered human vascular networks transplanted into secondary mice reconnect with the host vasculature and re-establish perfusion. Blood. 6718-6721.

Karnik SK, Brooke BS, Bayes-Genis A, Sorensen L, Wythe JD, Schwartz RS et al. A critical role for elastin signaling in vascular morphogenesis and disease. Development. 2003;130:411-423.

Kaufman et al. "Hematopoietic colony-forming cells derived from human embryonic stem cells" PNAS USA, 2001, vol. 98, pp. 10716-10721.

Khetan et al., (2009). Sequential crosslinking to control cellular spreading in 3-dimensional hydrogels. Soft Matter 5, 1601-1606.

Khetan et al., (2010). Patterning network structure to spatially control cellular remodeling and stem cell fate within 3-dimensional hydrogels. Biomaterials 31, 8228-8234.

Klein et al., "Megahertz OCT for ultrawide-field retinal imaging with a 1050nm Fourier domain mode-locked laser," Opt. Express, vol. 19, pp. 3044-3062, 2011.

Kobayash et al., "Mechanical Stress Promotes the Expression of Smooth Muscle-Like Properties in Marrow Stromal Cells", Experimental Hematology, vol. 32, pp. 1238-1245. (2004).

Koike et al. "Tissue engineering: creation of long-lasting blood vessels" Nature, 2004, vol. 428, pp. 138-139.

Kuprinski et al., "Transforming Growth Factor-B and Notch Signaling Mediate Stem Cell Differentiation Into Smooth Muscle Cells", Stem Cells, vol. 28, pp. 734-742. (2010).

Kuro-o et al. "Developmentally regulated expression of vascular smooth muscle myosin heavy chain isoforms", Journal of Biological Chemistry, 1989, vol. 264, pp. 18272-18275.

Stewart et al., (2011). Delta-like ligand 4-Notch signaling regulates bone marrow-derived pericyte/vascular smooth muscle cell formation, Blood 117, 719-726.

Stratman et al., (2009a). Pericyte recruitment during vasculogenic tube assembly stimulates endothelial basement membrane matrix formation. Blood 114, 5091-5101.

(56) References Cited

OTHER PUBLICATIONS

Stratman et al., (2009b). Endothelial cell lumen and vascular guidance tunnel formation requires MT1-MMP-dependent proteolysis in 3-dimensional collagen matrices. Blood 114, 237-247.
Sugiyama et al., "Characterization of smooth muscle-like cells in circulating human peripheral Blood", Atherosclerosis, 2006, vol. 187, pp. 351-362.
Swistowski et al, Efficient Generation of Functional Dopaminergic Neurons from Human Induced Pluripotent Stem Cells Under Defined Conditions. Stem Cells, 28, 1893-1904 (2010).
Takahashi K, Tanabe K, Ohnuki M, Narita M, Ichisaka T, Tomoda K et al. Induction of Pluripotent Stem Cells from Adult Human Fibroblasts by Defined Factors. Cell 2007;131:861-872.
Tan et al., "In-fiber common-path optical coherence tomography using a conical-tip fiber," Opt. Express 17(4),2375-2384(2009).
Taura D et al. "Induction and isolation of vascular cells from human induced pluripotent stem cells-brief report", Arterioscler Thromb Vasc Biol, 2009, vol. 29, pp. 1100-1103.
Thomson, J.A. (1998). Embryonic stem cell lines derived from human blastocysts. Science 282, 1145-1147.
Thyberg J. Differences in caveolae dynamics in vascular smooth muscle cells of different phenotypes. Lab Invest 2000;80:915-929.
Timmermans F et al. "Endothelial progenitor cells: Identity defined?" Journal of Cellular and Molecular Medicine, 2009, vol. 13, pp. 87-102.
Traktuev DO et al. "A population of multipotent CD34-positive adipose stromal cells sharepericyte and mesenchymal surface markers, reside in a perlendothelial location, and stabilizeendothelial networks", Circulation Research, 2008, vol. 102, pp. 77-85.
Tsai, M-C et al. "Shear Stress Induces Synthetic-to-Contractile Phenotypic Modulation inSmooth Muscle Cells via Peroxisome Proliferator-Activated Receptor (alpha)/(delta)Activations by Prostacyclin Released by Sheared Endothelial Cells" Circ Res, 2009, vol. 105,pp. 471-480.
Tuna BG, Bakker ENTP, VanBavel E. Smooth Muscle Biomechanics and Plasticity: Relevance for Vascular Calibre and Remodelling. Basic Clin Pharmacol Toxicol 2012;110:35-41.
Vakhtin et al., "Common-path interferometer for frequency-domain optical coherence tomography," App. Opt. 42(34), 6953-6958 (2003).
Van Kooten et al., "Fluid Shear Induced Endothelial Cell Detachment From Modified Polystyrene Substrata", Colloids and Surfaces B: Biointerfaces, vol. 3, No. 3, pp. 147-158. (1994).
Vazao H, das Neves RP, Graos M, Ferreira L. Towards the maturation and characterization of smooth muscle cells derived from human embryonic stem cells. PLoS One.2011;6:e17771. 5s.
Vo et al., "Smooth-Muscle-Like Cells Derived From Human Embryonic Stem Cells Support and Augment Cord-Like Structures In Vitro", Stem Cells Reviews and Reports, vol. 6, No. 2, pp. 237-247. (2010).
Vodyanik et al, Current protocols in cell biology, Chapter 23 (2007).
Vodyanik et al., (2010). A mesoderm-derived precursor for mesenchymal stem and endothelial cells. Cell Stem Cell 7, 718-729.
Vunjak-Novakovic et al., (2011). Biomimetic Platforms for Human Stem Cell Research. Cell Stem Cell 8, 252-261.
Wang D, Chang PS, Wang Z, Sutherland L, Richardson JA, Small E et al. Activation of cardiac gene expression by myocardin, a transcriptional cofactor for serum response factor. Cell 2001;105:851-862.
Wang et al. "Human Embryonic Stem Cells Maintained in the Absence of Mouse Embryonic Fibroblasts or Conditioned Media are Capable of Hematopietic Development." Blood 2005 105:4598-4603.
Wang et al., (2007). Endothelial cells derived from human embryonic stem cells form durable blood vessels in vivo. Nat Biotech 25, 317-318.
Wang Z, Wang DZ, Pipes GC, Olson EN. Myocardin is a master regulator of smooth muscle gene expression. Proc Natl Acad Sci U S A 2003;100:7129-7134.
Wanjare et al., (2012). Derivation and maturation of synthetic and contractile vascular smooth muscle cells from human pluripotent stem cells. Cardiovascular Research. 321-330.
Wolinsky H, Glagov S. A Lamellar Unit of Aortic Medial Structure and Function in Mammals. Circ Res 1967;20:99-111.
Woodford et al., "Tissue engineering 2.0: guiding self-organization during pluripotent stem cell differentiation," Current Opinion in Biotechnology, 2012, vol. 23, pp. 810-819.
Xiao Q, Zeng L, Zhang Z, Hu Y, Xu Q. Stem cell-derived Sca-1+ progenitors differentiate into smooth muscle cells, which is mediated by collagen IV-integrin $\alpha1/\beta1/\alpha v$ and PDGF receptor pathways. Am J Physiol Cell Physiol 2007;292:C342-C352.
Xie C, Guo Y, Zhu T, Zhang J, Ma PX, Chen YE. Yap1 Protein Regulates Vascular Smooth Muscle Cell Phenotypic Switch by Interaction with Myocardin. J Biol Chem 2012;287:14598-14605.
Xie et al. "A comparison of murine smooth muscle cells generated from embryonic versus induced pluripotent stem cells" Stem Cells Dev, 2009, vol. 18, pp. 741-748.
Xie et al., "A Highly Efficient Method to Differentiate Smooth Muscle Cells Form Human Embryonic Stem Cells," Arteriosclerosis, Thrombosis, and Vascular Biology, vol. 27, No. 12, 2007, pp. e311-e312.
Xie W-B, Li Z, Miano JM, Long X, Chen S-Y. Smad3-mediated Myocardin Silencing. J Biol Chem 2011;286:15050-15057.
Xu Y, Stenmark KR, Das M, Walchak SJ, Ruff LJ, Dempsey EC. Pulmonary artery smooth muscle cells from chronically hypoxic neonatal calves retain fetal-like and acquire new growth properties. Am J Physiol Lung Cell Mol Physiol 1997;273:L234-L245.
Yamamoto M, Yamamoto K, Noumura T. Type I Collagen Promotes Modulation of Cultured Rabbit Arterial Smooth Muscle Cells from a Contractile to a Synthetic Phenotype. Exp Cell Res 1993;204:121-129.
Yamashita J, Itoh H, Hiroshima M, Ogawa M, Nishikawa S, Yurugi T et al. Flk1-positive cells derived from embryonic stem cells serve as vascular progenitors. Nature. 2000;408:92-96.
Yang et al., (2008). Human cardiovascular progenitor cells develop from a KDR+ embryonic-stemcell-derived population. Nature 453, 524-528.
Yu et al., "Oxidized low density lipoprotein-induced transdifferentiation of bone marrow-derived smooth muscle-like cells into foam-like cells in vitro" International Journal of Experimental Pathology, vol. 91, pp. 24-33 (Dec. 22, 2009).
Zhang et al., "Common-path low-coherence interferometry fiber-optic sensor guided microincision," J. Biomed. Opt. 16(9),095003(2011).
Zhang et al., "Real-time intraoperative 4D full-range FD-OCT based on the dual graphics processing units architecture for microsurgery guidance," Biomed. Opt. Express. 2(4), 764-770 (2011).
Zou et al., (2011). Site-specific gene correction of a point mutation in human iPS cells derived from an adult patient with sickle cell disease. Blood 118, 4599-4608.
Zysk et al., "Optical coherence tomography: a review of clinical development from bench to bedside," J. Biomed. Opt. 12(5), 051403 (2007).
Narsinh, et al., "Comparison of human induced pluripotent and embryonic stem cells: fraternal of identical twins" Molecular Therapy 2011, vol. 9, No. 4, pp. 635-638.
Bellin, et al., "Induced pluripotent stem cells: the new patient?" Nature reviews/Molecular Cell Biology 2012, vol. 13, pp. 713-726.
Burridge, et al., "A universal system for highly efficient cardiac differentiation of human induced pluripotent stem cells that eliminates interline variabiligy" PLoS One 2011, vol. 6, No. 4, e18293, pp. 1-16.
Wang, Yigang, "Myocardial reprogramming medicine: the development application and challenge of induced pluripotent stem cells" New Journal of Science 2014, Article ID 756240, pp. 1-22.

* cited by examiner

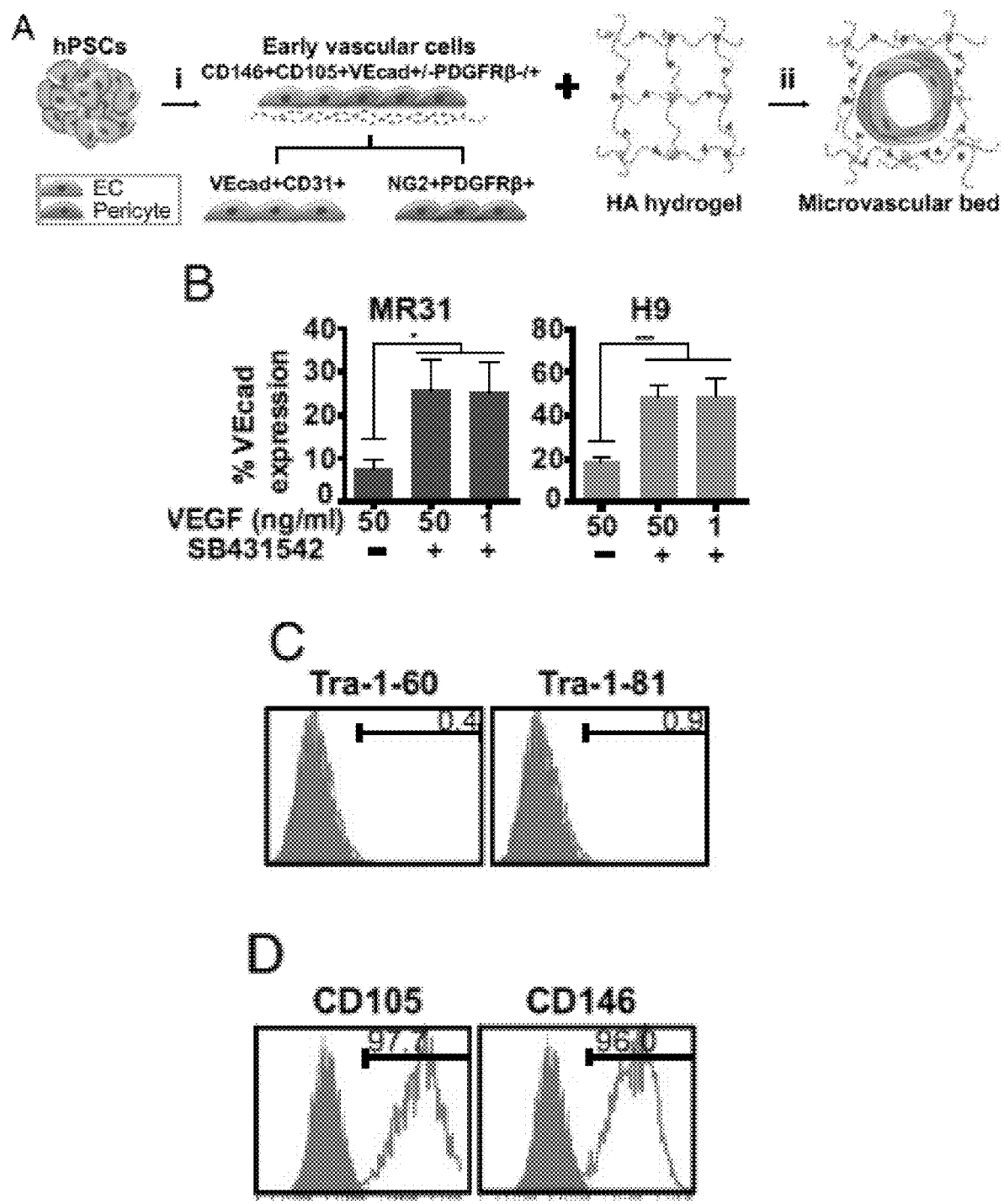
Figure 1A-D

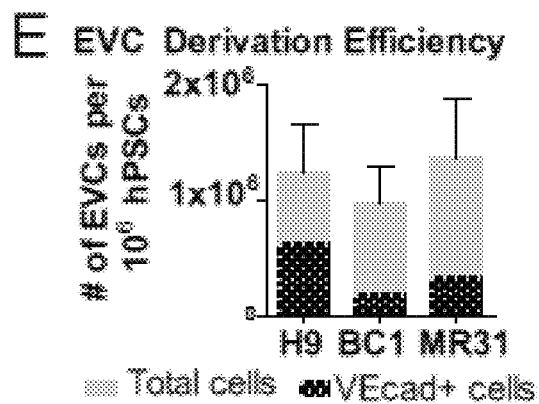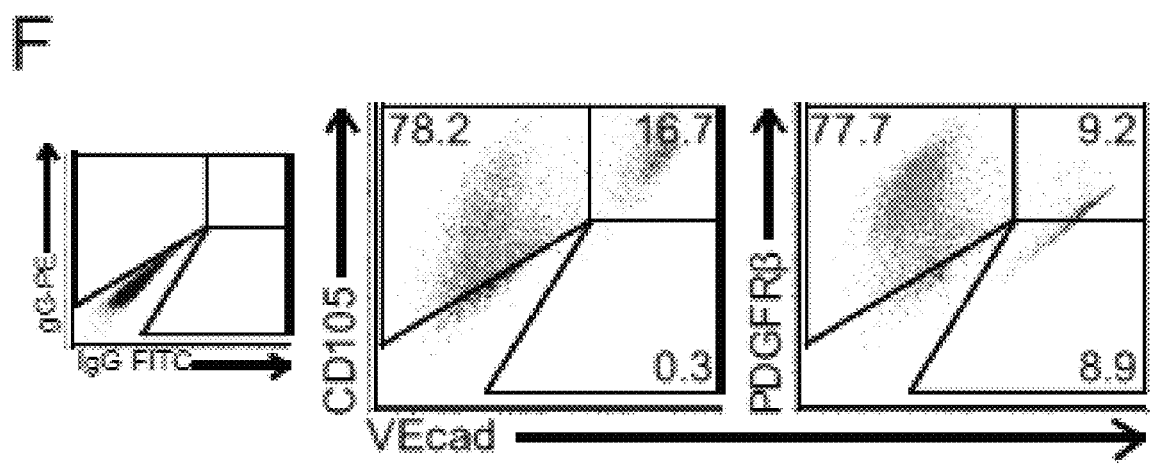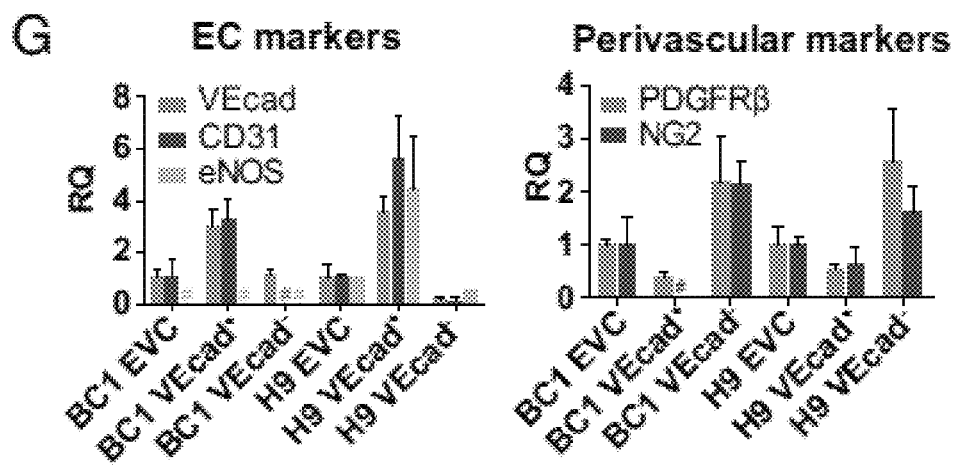
Figure 1E-G

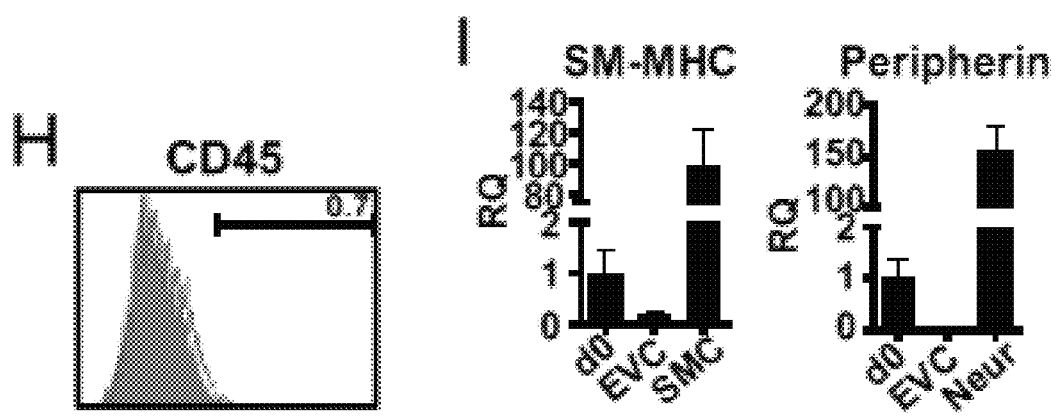
Figure 1H-I
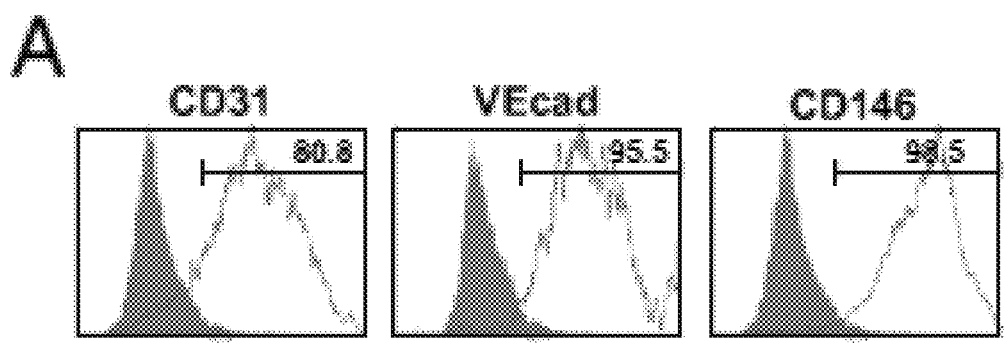
Figure 2A

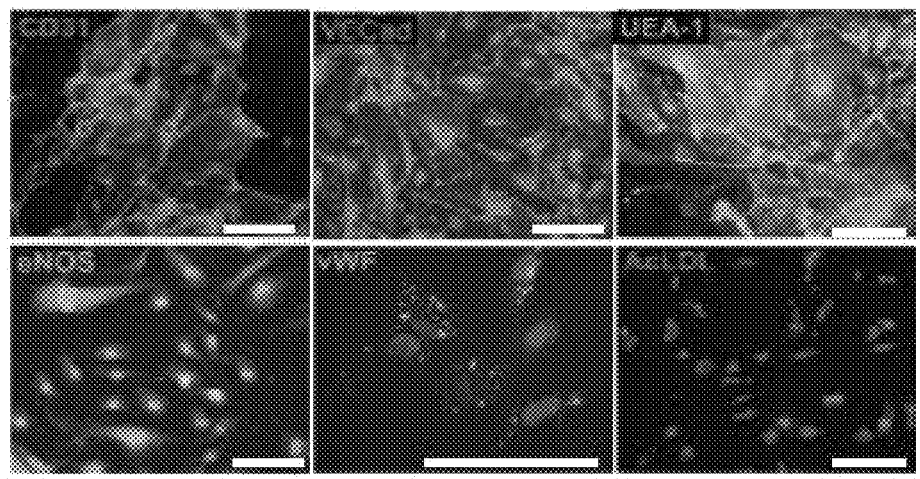
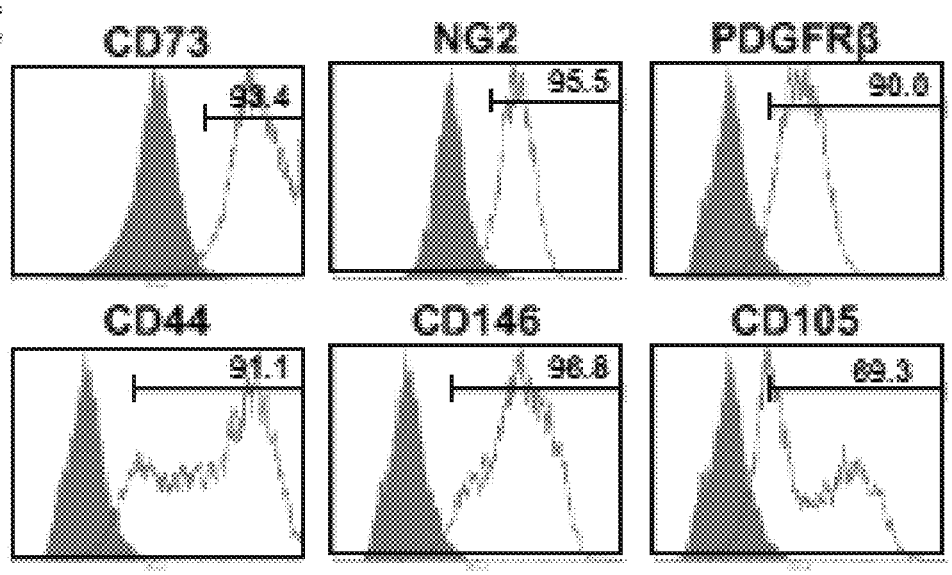
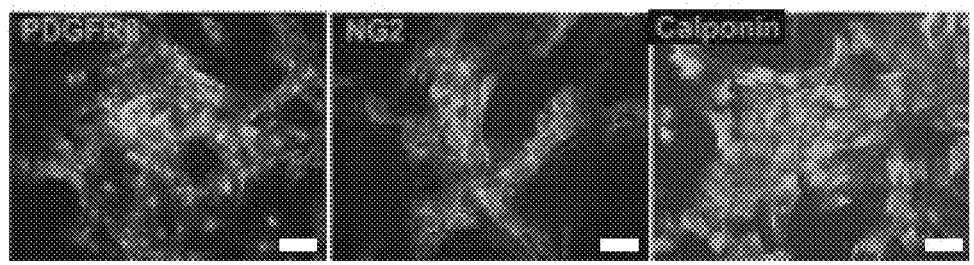
Figure 2 B-D

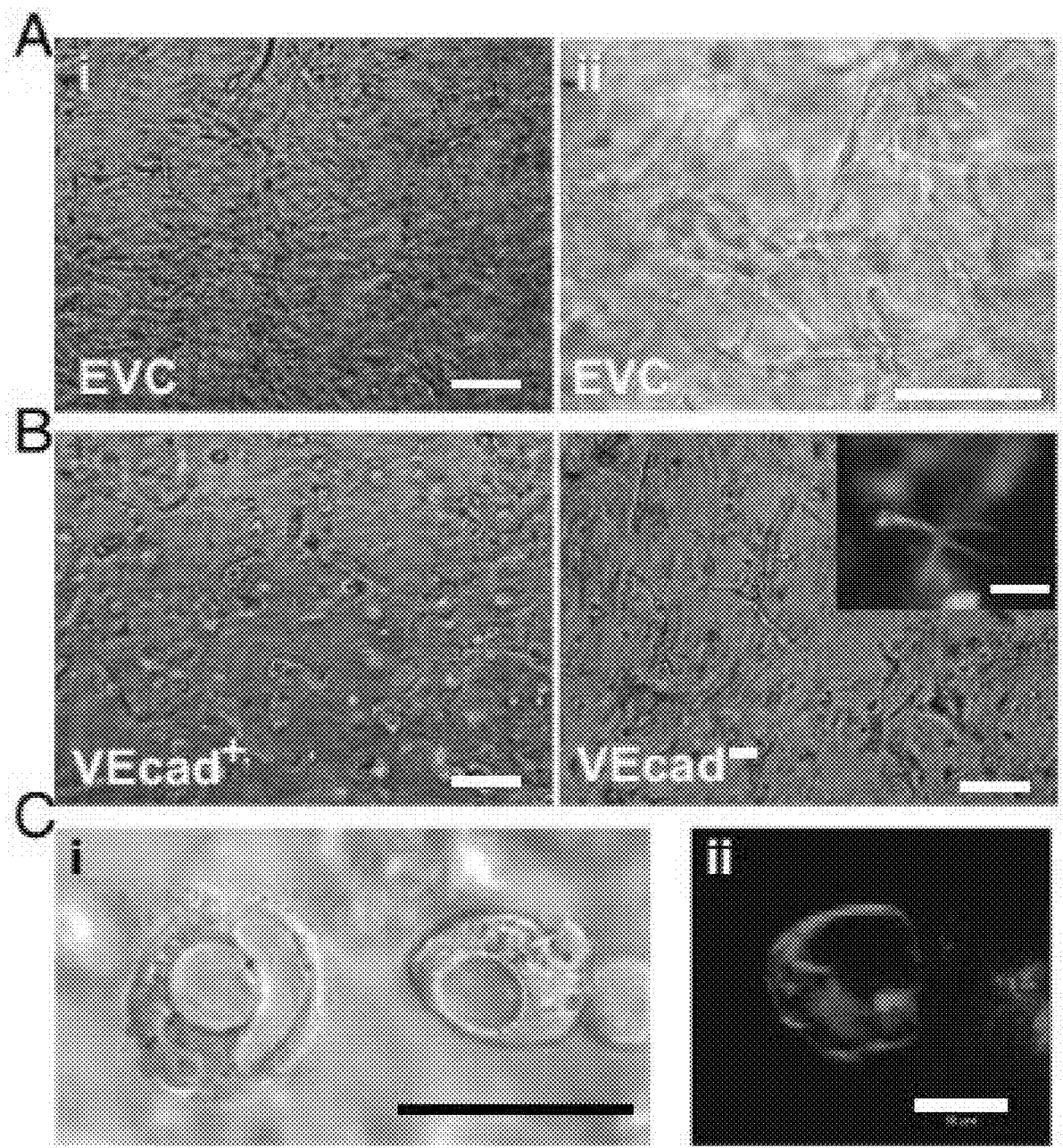
Figure 3A-C

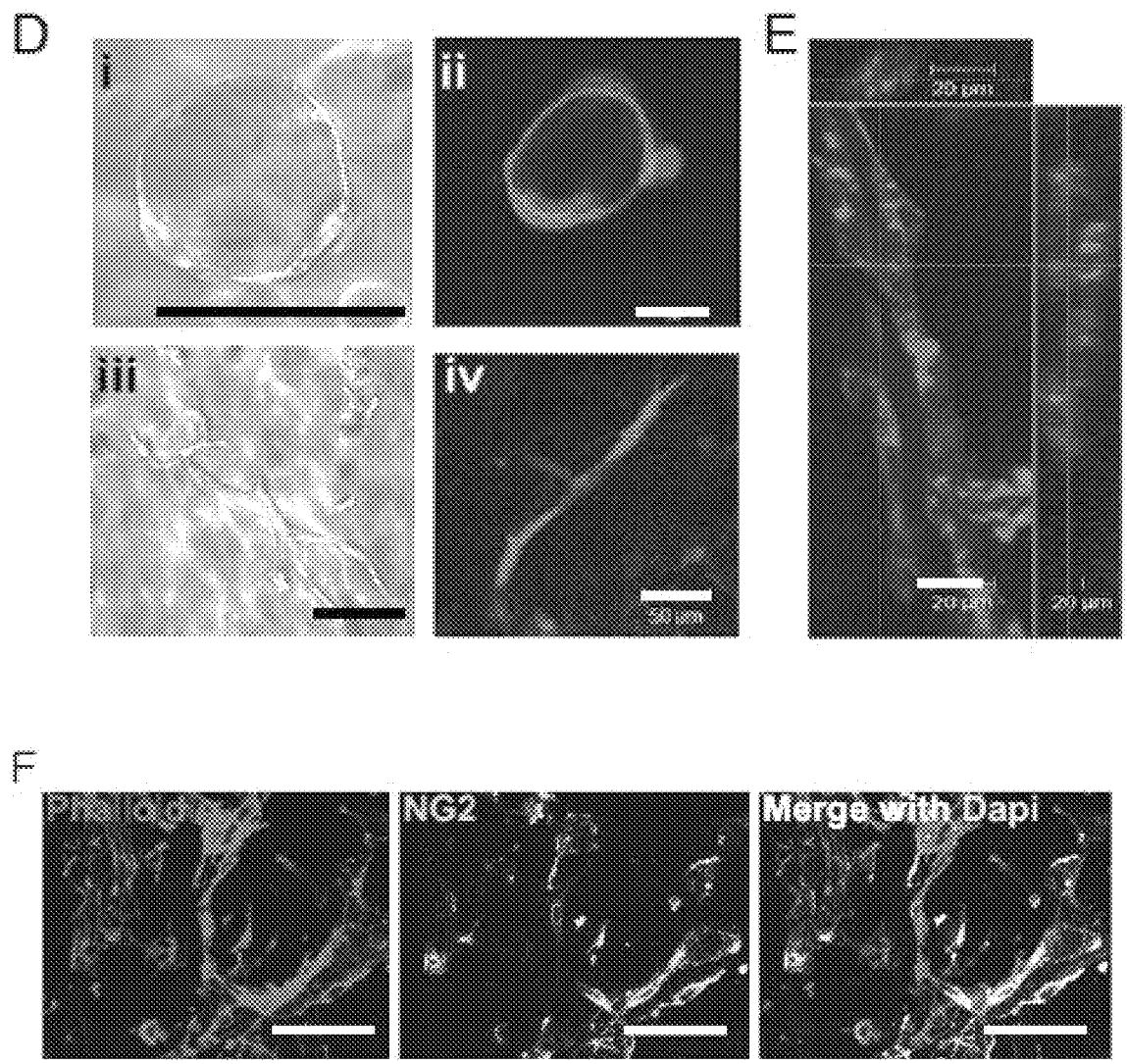
Figure 3D-F

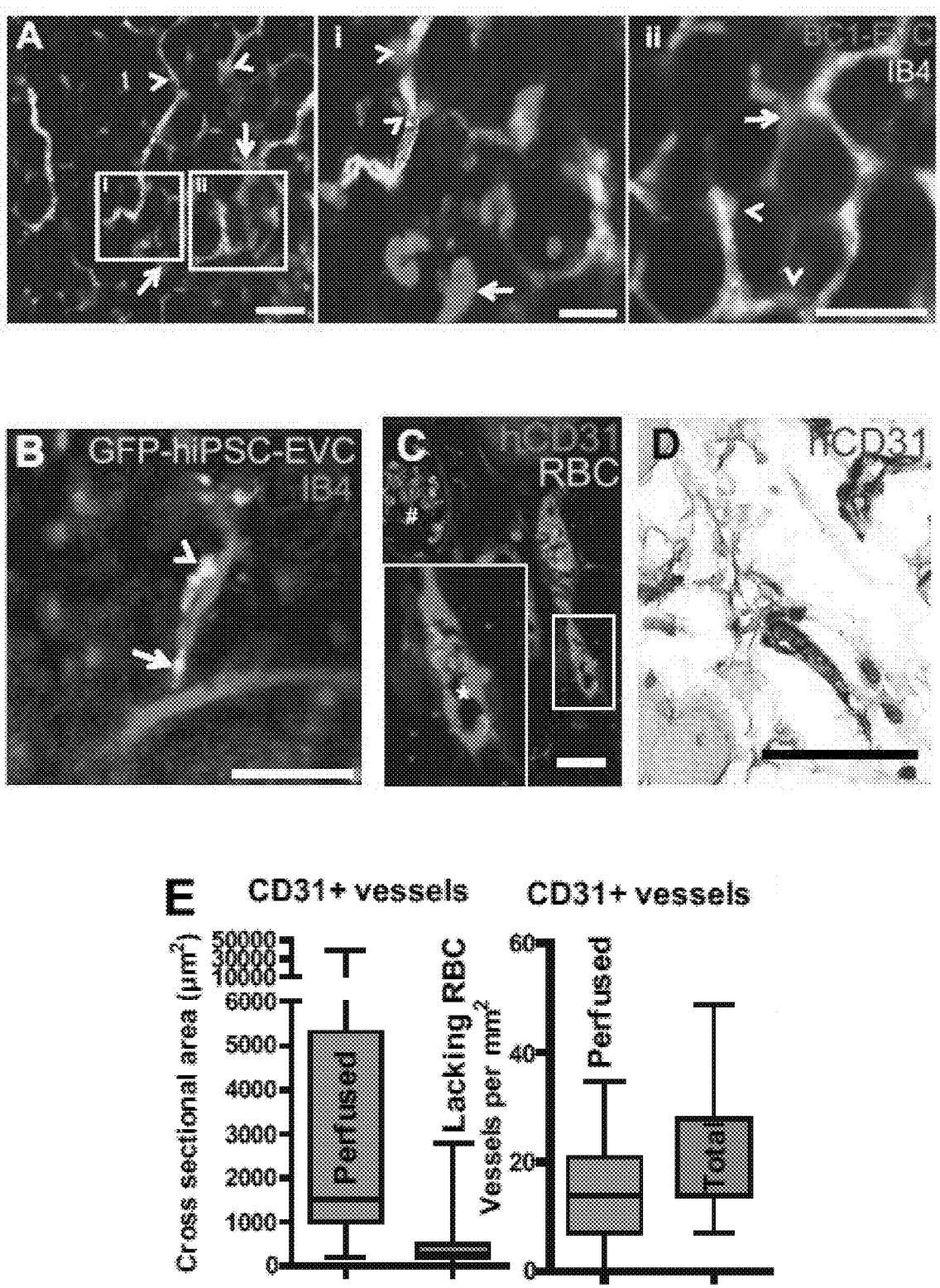
Figure 4A-E

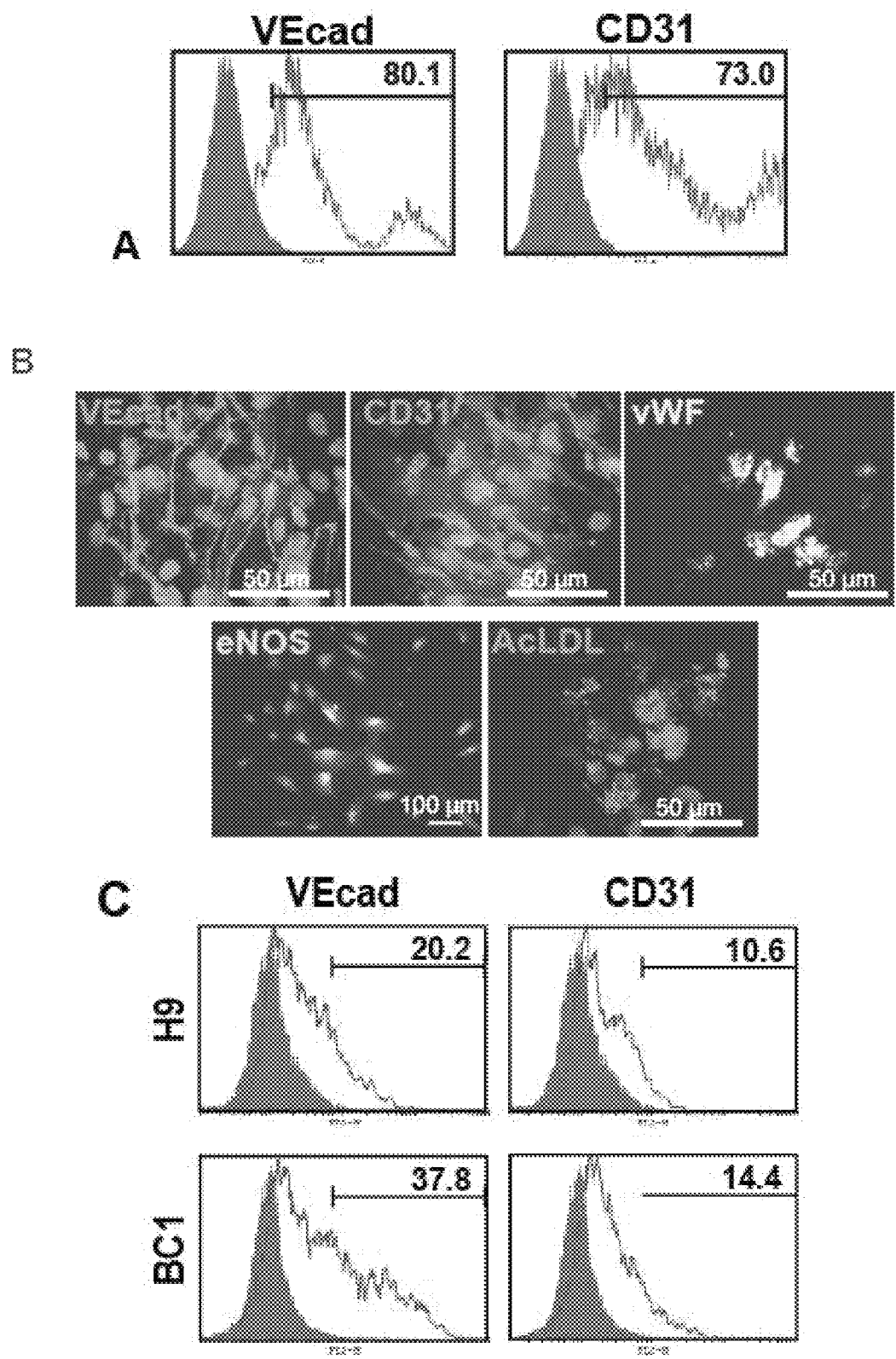
Figure 11A-C

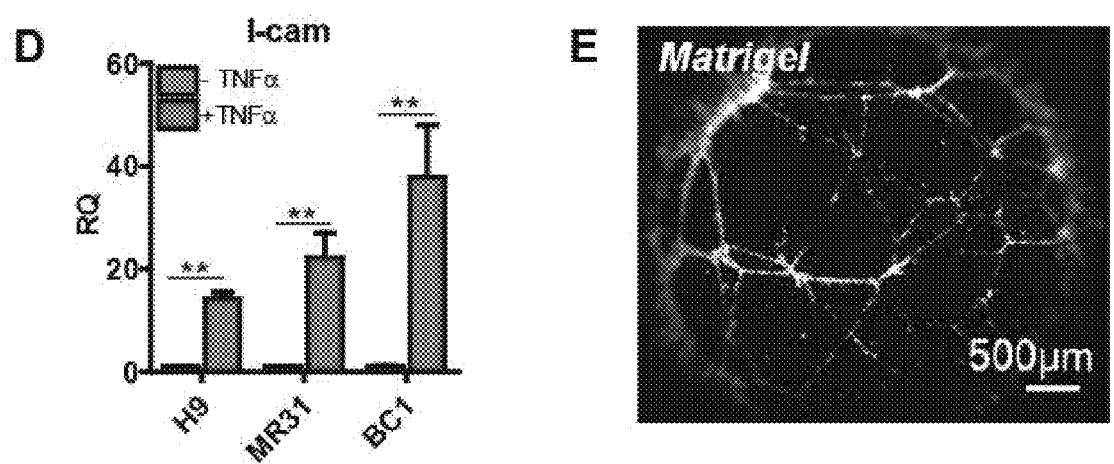
Figure 11 D-E

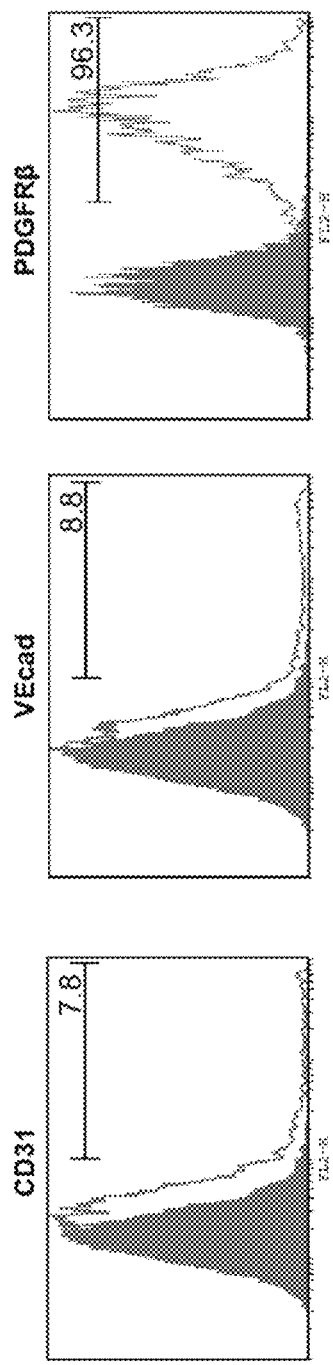
Figure 12
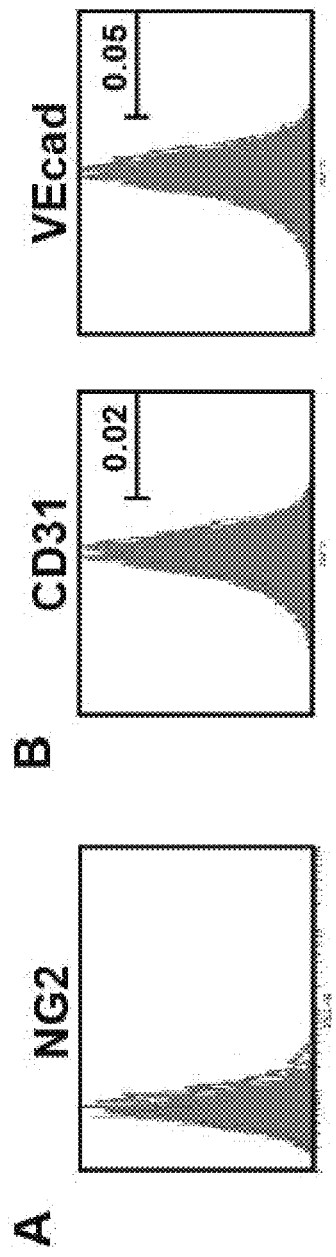
Figure 13A-B

Figure 13C-D

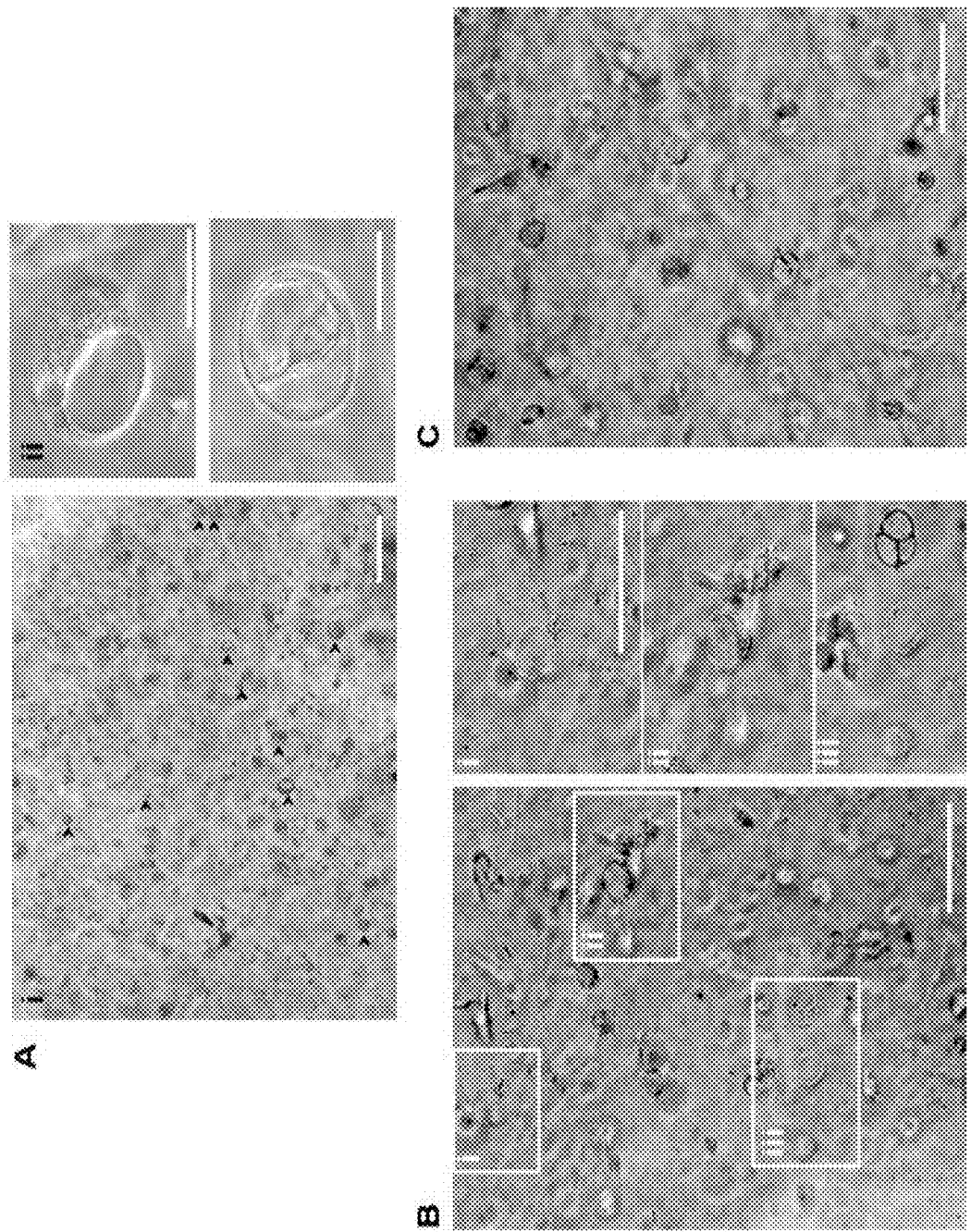
Figure 16A-C

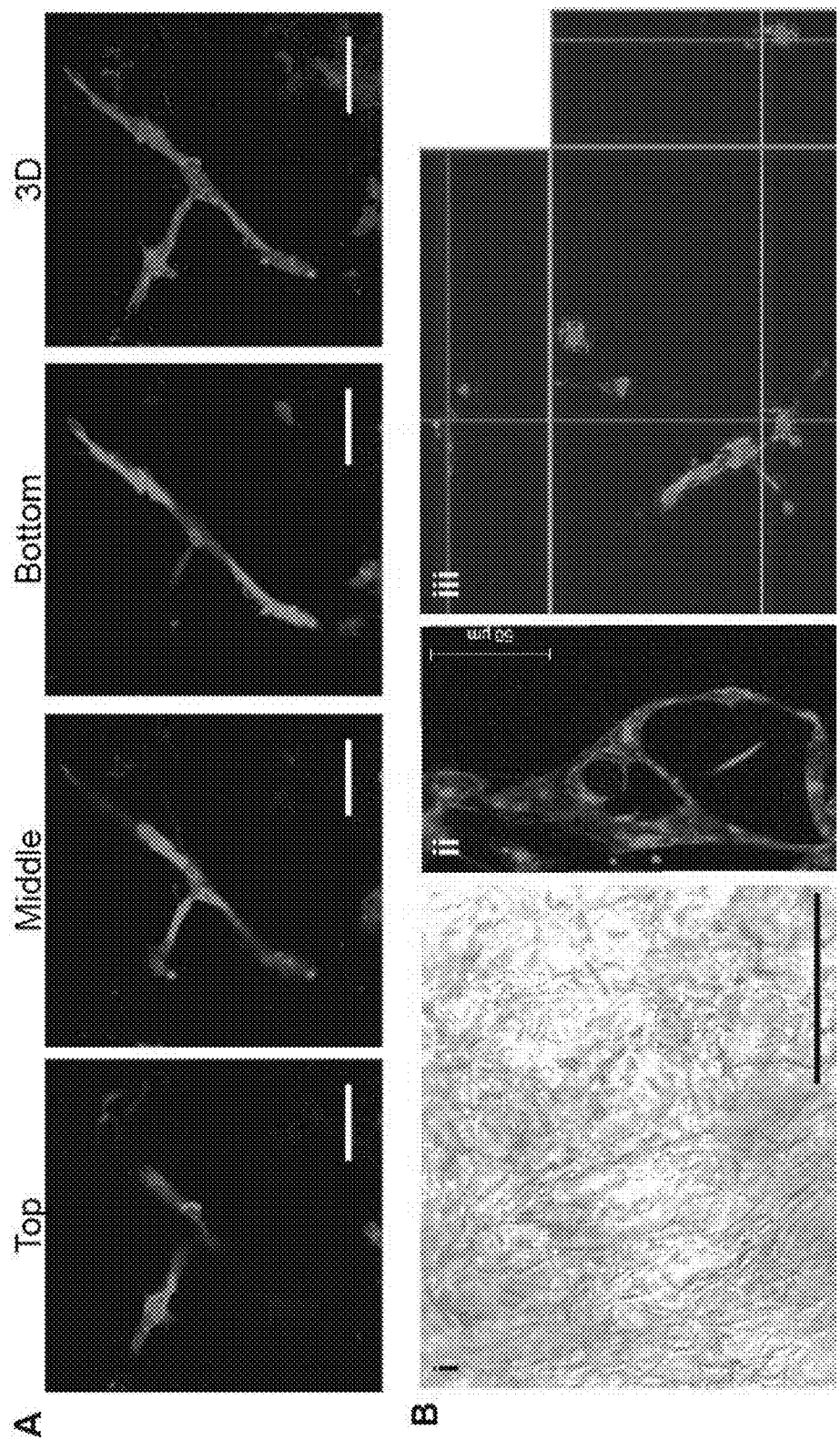
Figure 17A-B

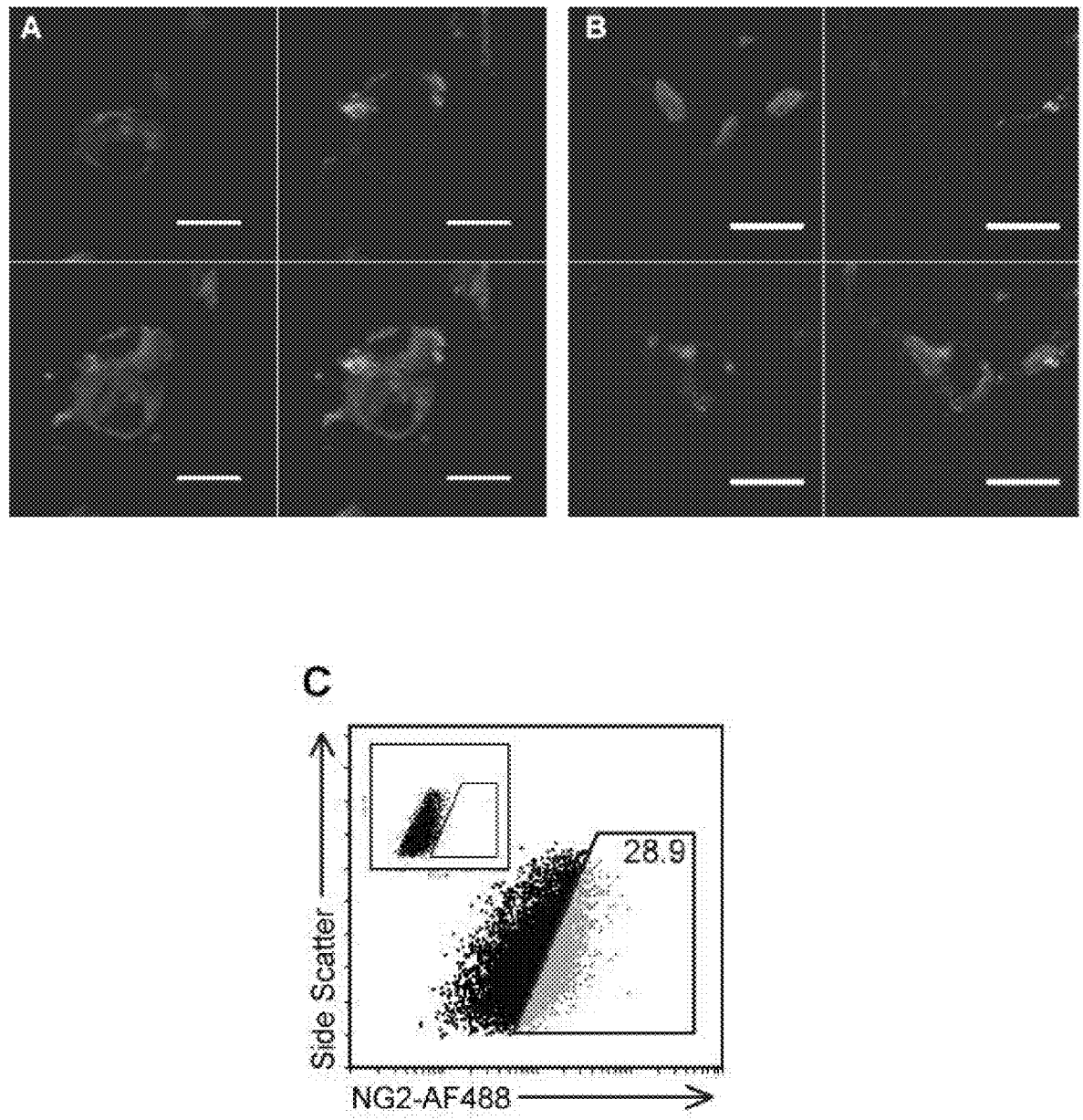
Figure 18A-C

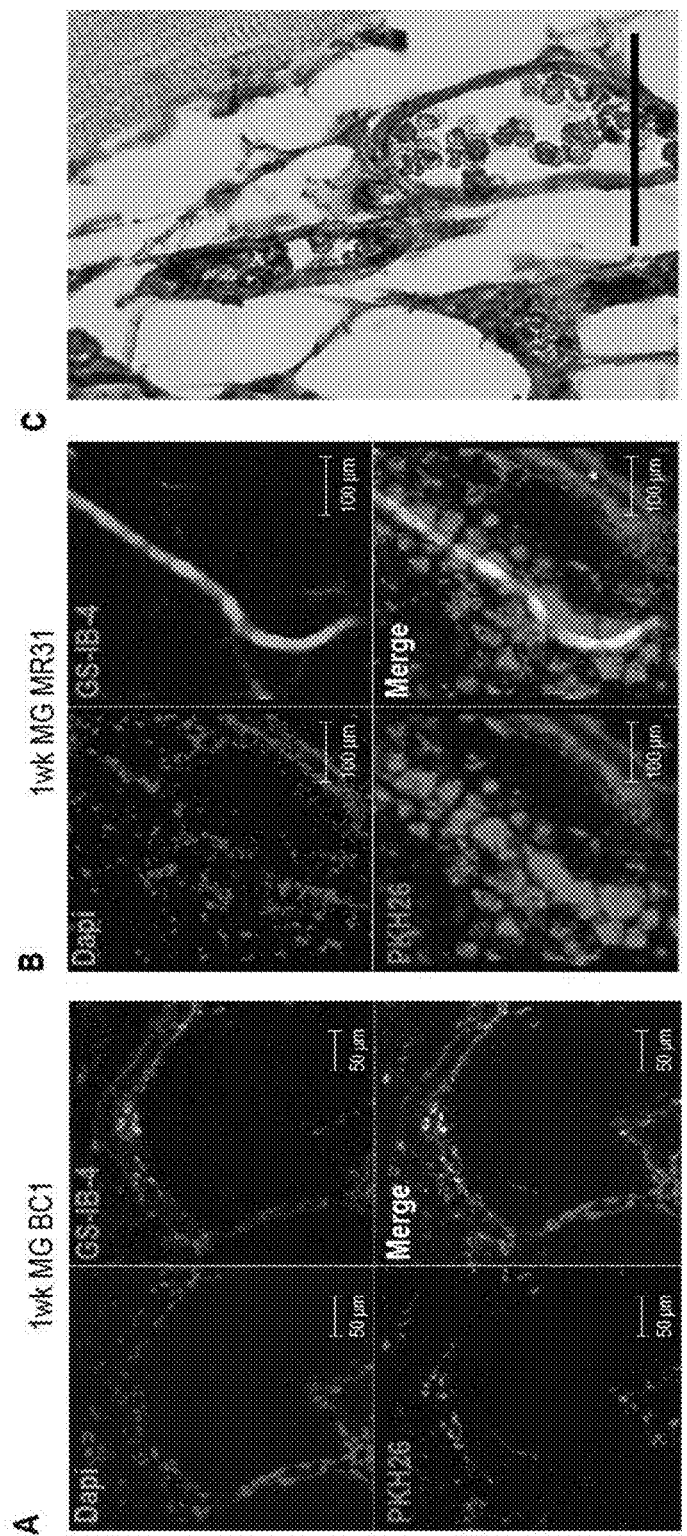
Figure 19A-C

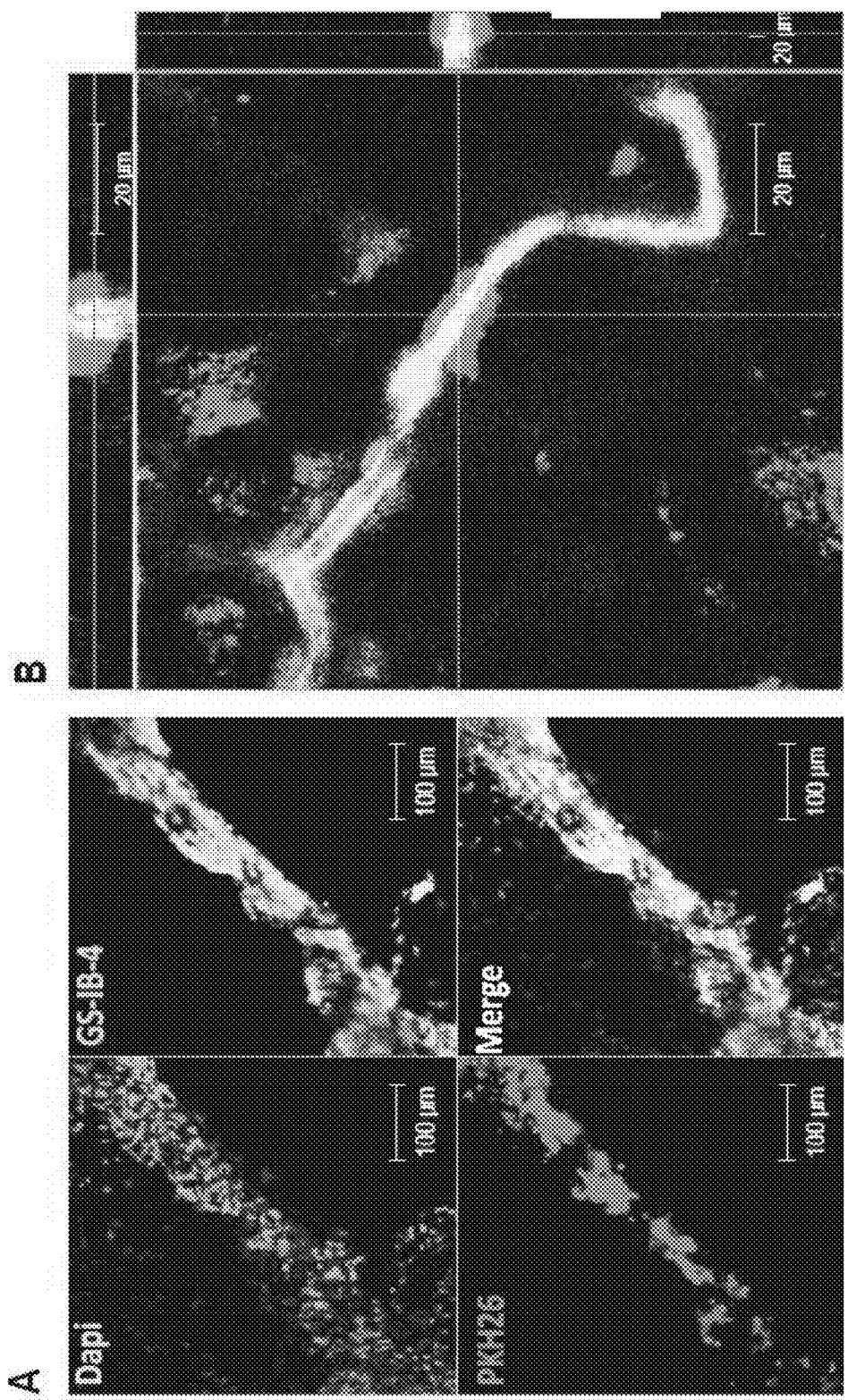
Figure 20A-B

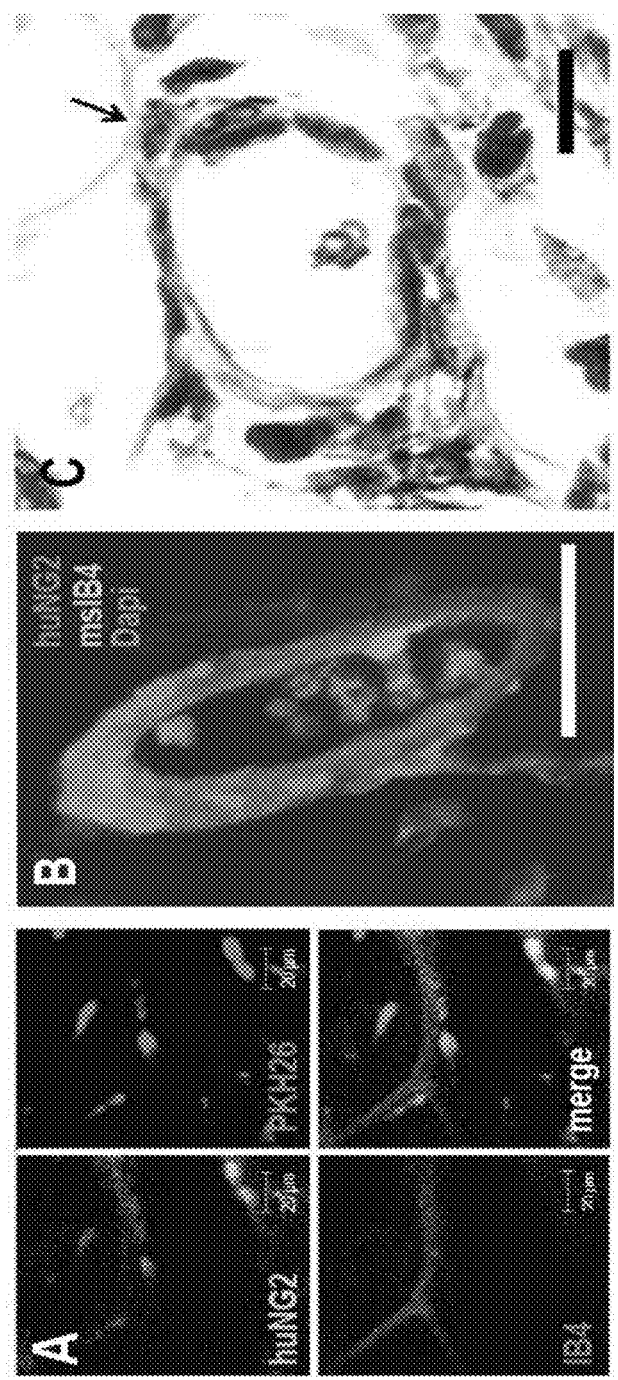
Figure 21A-C

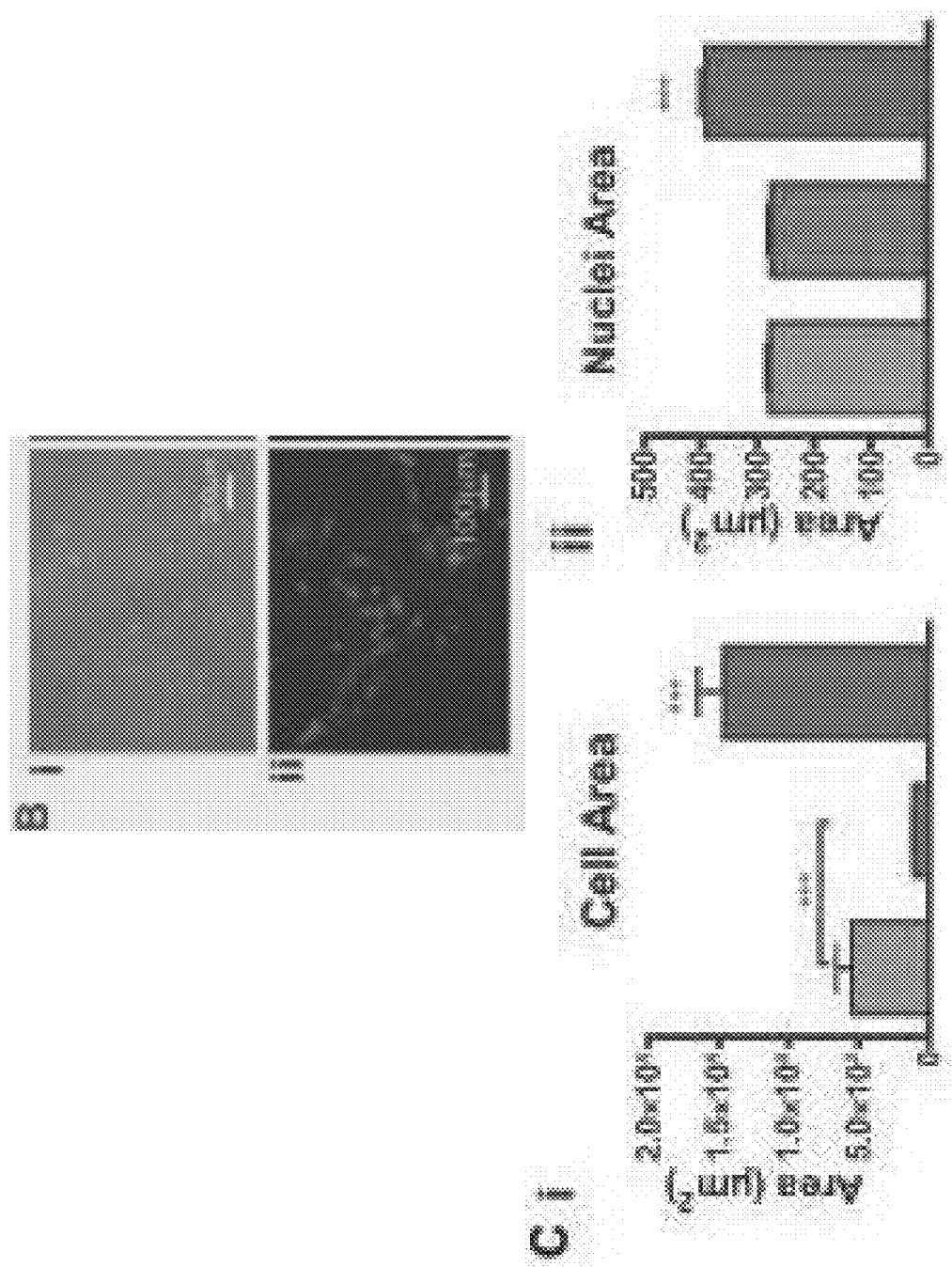
Figure 23B-C

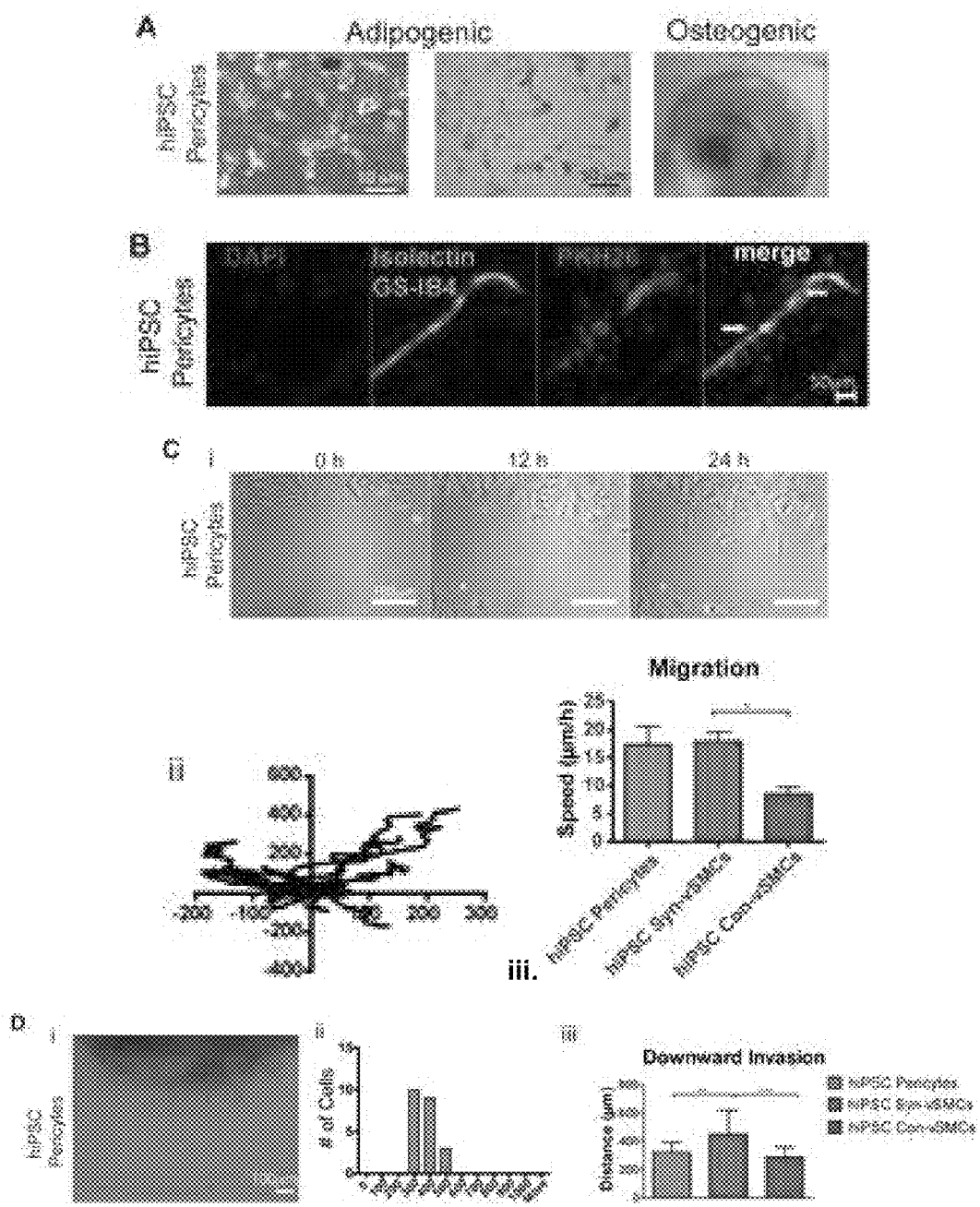
Figure 26A-D

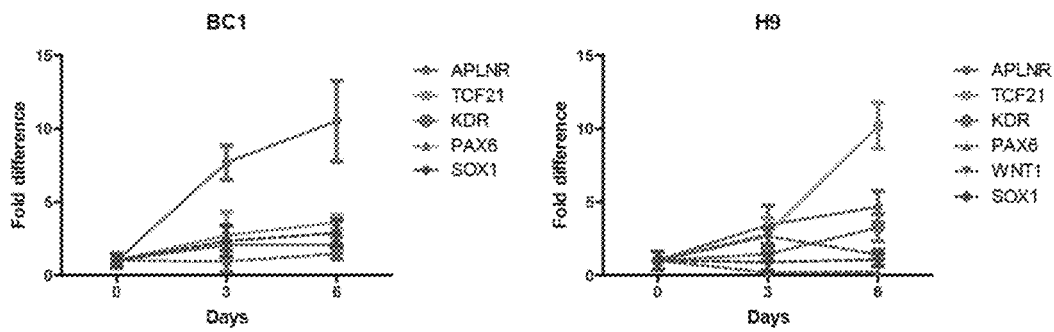
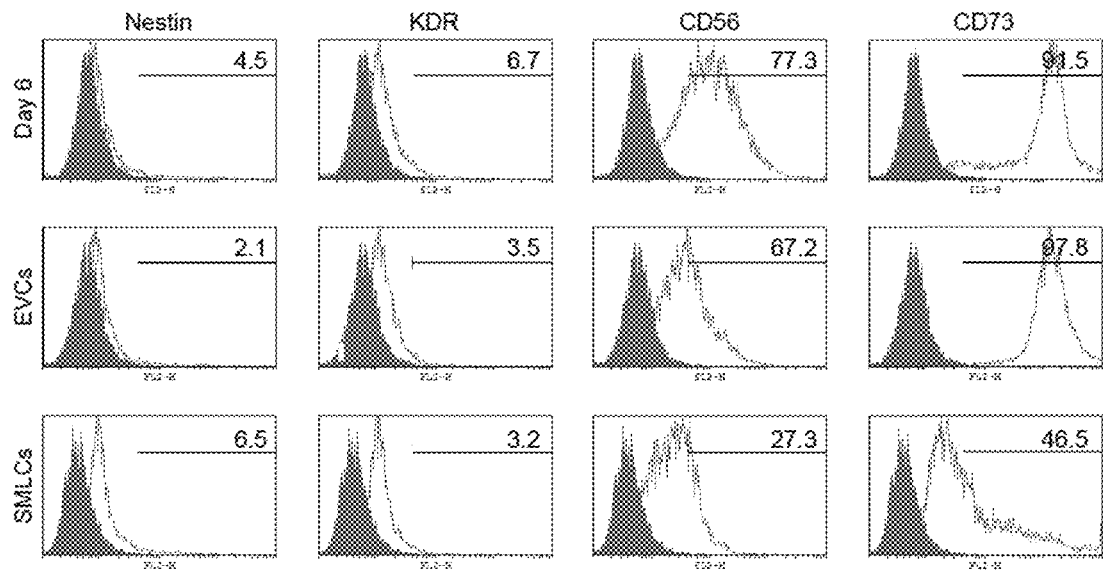
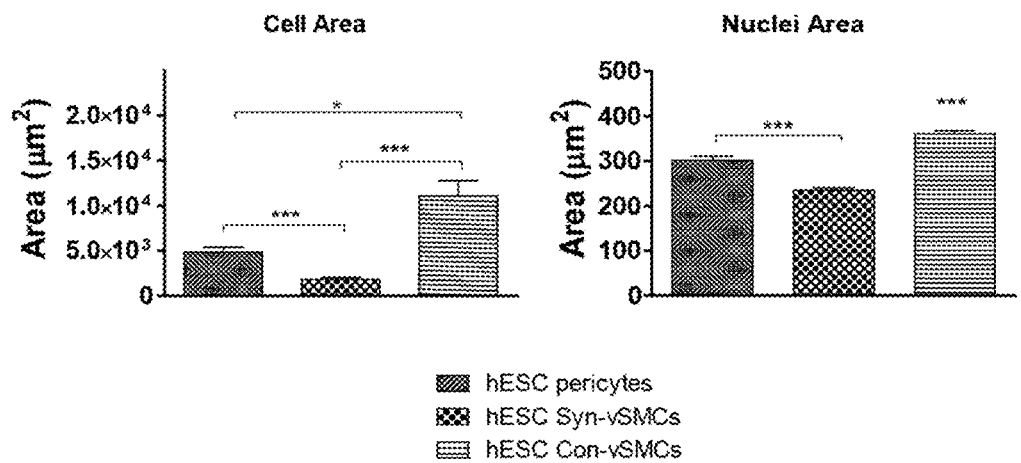
Figure 27A-C

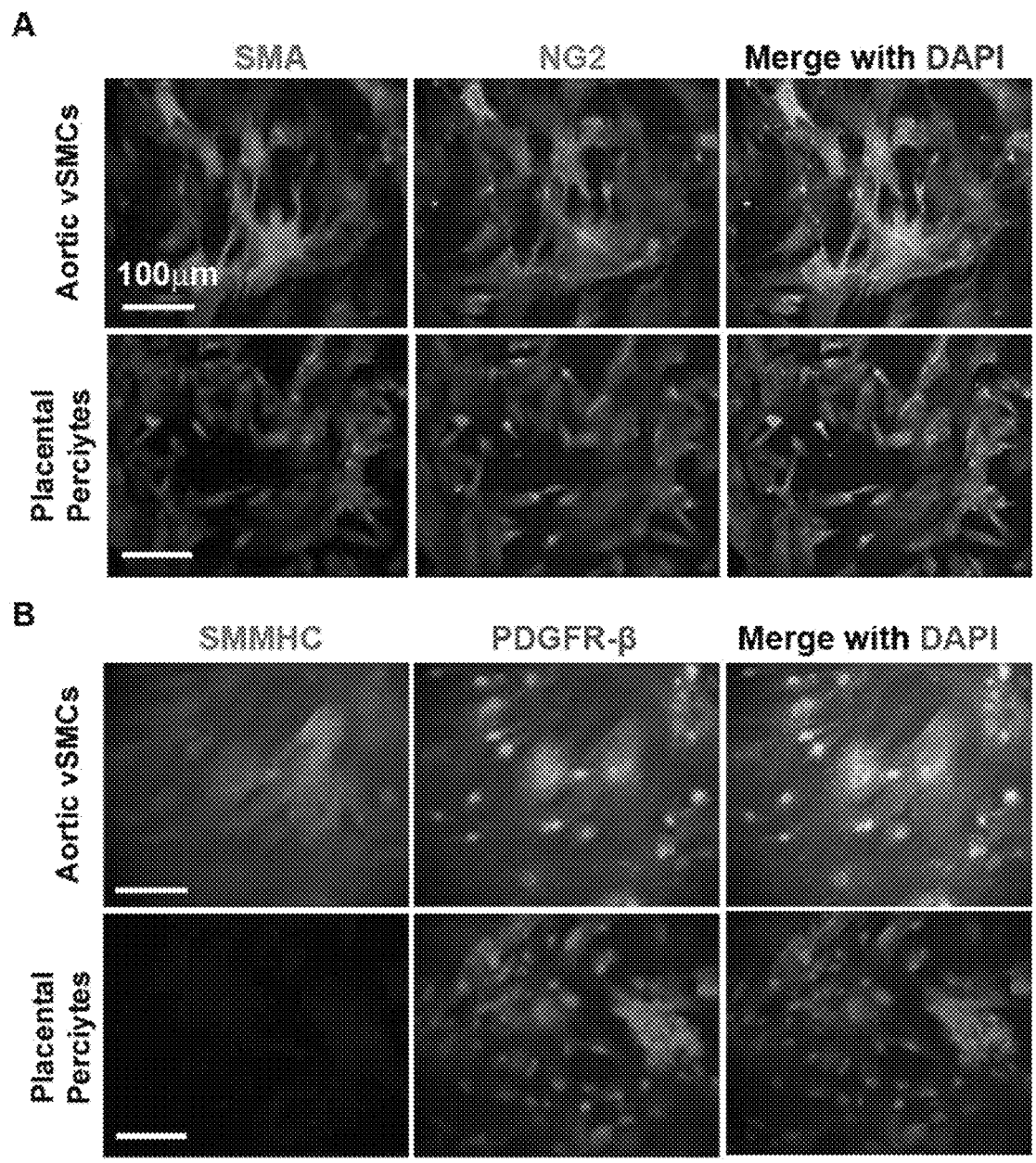
Figure 29 A-B

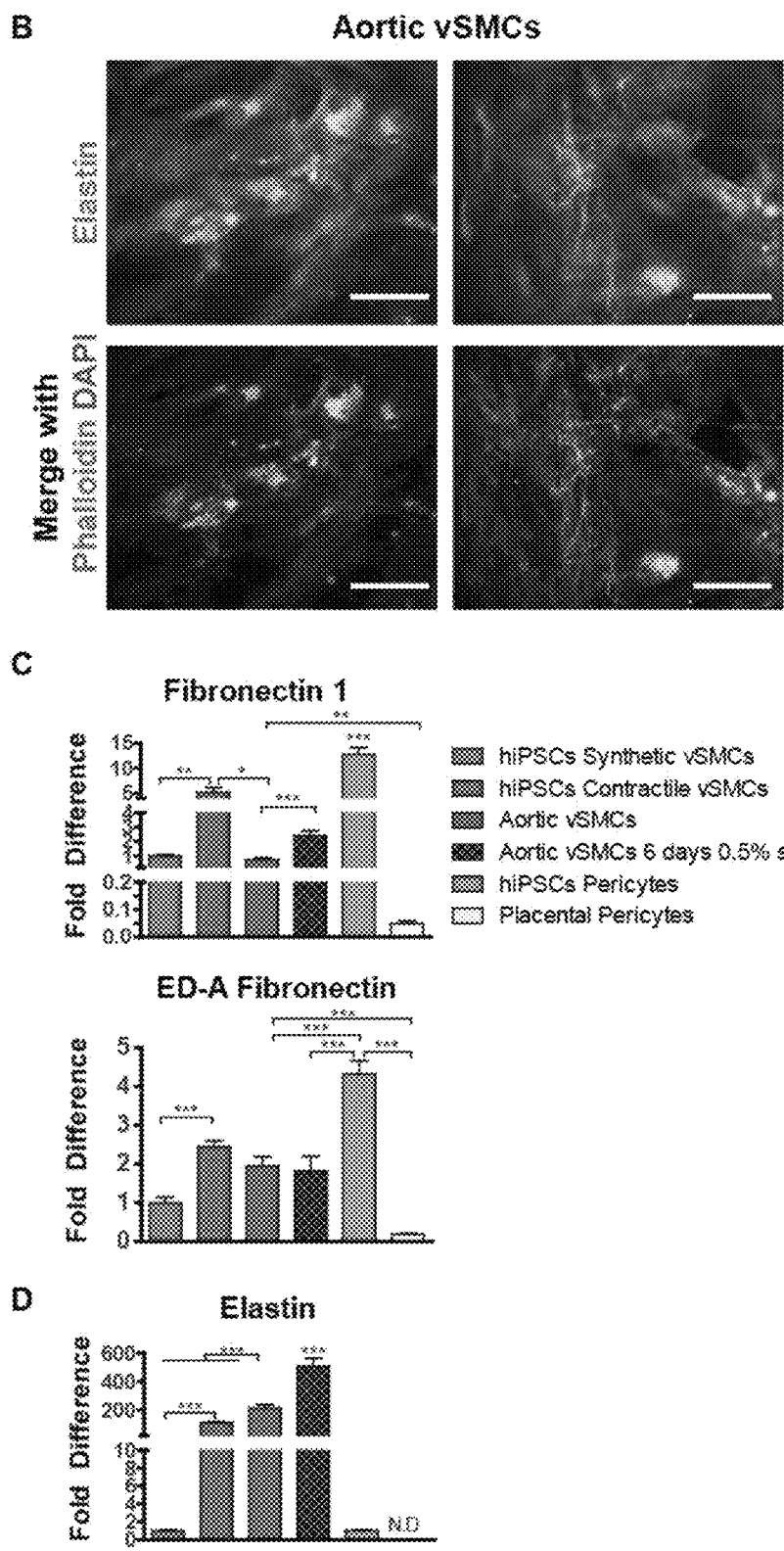
Figure 30B-D

EARLY VASCULAR CELL POPULATION

CROSS-REFERENCE TO PRIOR APPLICATIONS

This application is a Divisional of U.S. patent application Ser. No. 14/777,258, filed Sep. 15, 2015, now U.S. Pat. No. 9,994,825, issued Jun. 12, 2018, which is a 35 U.S.C. § 371 U.S. national entry of International Application PCT/US2014/030708, having an international filing date of Mar. 17, 2014, which claims the benefit of U.S. Provisional Application No. 61/846,369, filed Jul. 15, 2013, and is a U.S. Continuation-in-Part of U.S. application Ser. No. 13/844,313, filed Mar. 15, 2013, now U.S. Pat. No. 9,506,037, the content of each of the aforementioned applications is herein incorporated by reference in their entirety.

GOVERNMENT SUPPORT

This invention was made with government support under grant numbers HL112644, HL073781, HL107938, CA143868, awarded by the National Institutes of Health, and grant number 1054415, awarded by the National Science Foundation. The government has certain rights in the invention.

BACKGROUND OF THE INVENTION

Area of the Art

The present invention is in the area of pluripotent stem cells and more particularly deals with a method to differentiate a vascular network from stem cells.

Description of the Background Art

Perhaps the greatest roadblock to the success of tissue regenerative therapies is the establishment of a functional microvascular network to support tissue survival and growth (Discher et al., 2009). Microvascular construction or regeneration depends on endothelial morphogenesis into a three-dimensional, tubular network followed by stabilization of the assembling structures by recruited pericytes (Hanjaya-Putra et al., 2011; Stratman et al., 2009a). To create such a construct for therapeutic applications, patient-derived ECs and pericytes must be incorporated into a synthetic matrix, which confers the advantage to control and modulate vascular morphogenesis and simultaneously represents a clinically-relevant construct in which to deliver the engineered microvascular networks to in vivo environments (Vunjak-Novakovic and Scadden, 2011).

The vasculature is a multicellular system in which each cell type plays an important and indispensable role in its function. The inner lining of endothelial cells (ECs), which are in direct contact with the blood, is surrounded and supported by perivascular cells—either vascular smooth muscle cells (vSMCs) or pericytes. Vascular SMCs surround larger vessels such as arteries and veins, whereas pericytes typically surround smaller microvessels and capillaries (Bruce Alberts, 2002). The disparate vessel locations for each perivascular cell type suggests that further differences exist that should be investigated and better understood in vitro in order to appropriately rebuild blood vessels for therapeutic applications (Dar and Itskovitz-Eldor, 2013; Wanjare et al., 2013b).

As the vasculature's support system, perivascular cells are primarily responsible for imparting contractility and producing and depositing extracellular matrix (ECM) proteins. Both cell types migrate to sites of angiogenesis, the growth of blood vessels from pre-existing ones, to help stabilize and mature nascent endothelial tubes. Whether pericytes and vSMCs function similarly in these regards and to what extent has been unclear.

Along with the aforementioned functional similarities, perivascular cell types also exhibit overlapping marker expression. Adding to this complexity, neither perivascular cell type can be distinguished by one marker alone; instead, a combination of markers is needed for their identification. For example, both cell types have been demonstrated to express alpha smooth muscle actin ($\alpha$-SMA). The expression of $\alpha$-SMA and the transmembrane chondroitin sulfate proteoglycan neuron-glial 2 (NG2) help distinguish pericytes in different vessel types (Crisan et al., 2012); pericytes of the capillaries are NG2+ $\alpha$SMA−, of the venules are NG2−$\alpha$SMA+, and of the arterioles are NG2+ $\alpha$SMA+. When cultured in vitro, however, pericytes are positive for both of these markers. Other markers that are expressed on both perivascular cell types include calponin and PDGFR$\beta$ (Birukov et al., 1991; Dar et al., 2012).

Human pluripotent stem cells (hPSCs), including human embryonic stem cells (hESCs) and human induced PSCs (hiPSCs), offer the opportunity to derive early vascular cells (EVCs) from the same source, the latter of which offers patient specificity. Various cell markers have been proposed to identify vascular precursors (of ECs and pericytes) from differentiating hPSCs including CD34 (Ferreira et al., 2007; Park et al., 2010), KDR/VEGFR2 (Yang et al., 2008), and apelin receptor (Vodyanik et al., 2010). Purification of such progenitors is required from an uncontrolled differentiated cell population (i.e. via embryoid body [EB] formation or co-culture on mouse feeder layer) through marker enrichment or selection through genetic manipulation. Importantly, none of these derived cells have been demonstrated to self-assemble into functional microvasculature containing both ECs and pericytes.

Current approaches for the differentiation of hPSCs toward the vascular lineage build on the notion that a purified, single derivative—either a progenitor or matured cell type—is obligatory for the generation of functional vasculature. These approaches stem from the necessity to eliminate differentiation to undesirable lineages as well as to better understand the development of the vasculature. Indeed, from this body of work, it has become apparent that various cell markers and biochemical cues can be used to guide differentiation and derive functional ECs (Drukker et al., 2012; Ferreira et al., 2007; James et al., 2010; Wang et al., 2007), vascular smooth muscle cells (Drukker et al., 2012; Ferreira et al., 2007; Wanjare et al., 2012) and pericytes (Dar et al., 2011).

SUMMARY OF THE INVENTION

Here we disclose a new conceptual approach in which the cells of the microvasculature are derived in a single, bipotent type population. The developed protocol employs a monolayer culture and avoids an EB intermediate and sorting, thereby ensuring reproducibility and clinical applicability. The derived bipotent population is able to work synergistically to recreate the tissue. Thus, we harness intrinsic tissue-level differentiation and self-assembly capabilities toward the translational realization of hPSCs. This new paradigm could prove useful for the construction of other multicellular tissues for regeneration.

Additionally, an area of interest in the field is the ability to distinguish between perivascular cell types. As such, this remains a hurdle in vascular biology due to overlapping marker expressions and similar functionalities. Clarifying and defining heterogeneities in vitro among perivascular cells could lead to improved cell-based tissue regeneration strategies and a better understanding of human developmental processes. Here, we studied contractile vSMCs, synthetic vSMCs, and pericytes derived from a common human pluripotent stem cell source. Using in vitro cultures, we show unique cell morphology, subcellular organelle organization (namely endoplasmic reticulum, mitochondria, and stress fibers), and expression of smooth muscle myosin heavy chain and elastin for each cell type. Overall, we define a repertoire of functional phenotypes in vitro specific for each of the human perivascular cell types, enabling their study and use in basic and translational research.

The current disclosure demonstrates that hPSCs can be induced to differentiate into early derivatives of the vascular lineage (i.e. EVCs) that comprise the microvascular architecture without a specific differentiation-inducible feeder layer, EB formation, or genetic manipulation, and that such EVCs can mature into ECs and pericytes and can self-assemble to form functional vascular networks in an engineered matrix. In addition, it further discloses how different types of perivasulcar cells can be differentiated and identified.

The balance between commitment and plasticity of the EVCs specifically within the vascular lineage allows for vascular fate and functional network maturation. This controlled system is reproducible, generates physiologically relevant vascular networks in implantable matrices, and thus presents the next fundamental step toward patient-specific engineered tissue with clinically translatable potential.

DESCRIPTION OF THE FIGURES

FIG. 1A-1I shows derivation of EVCs from hPSCs. FIG. 1A, Schema for self-assembled vascular derivatives. (i) hPSCs are differentiated toward EVCs that can be matured into functional ECs and pericytes. (ii) Derived EVCs are embedded within a synthetic HA matrix that facilitates self-organization into vascular networks. FIG. 1B, VEcad expression in day 12 differentiated hiPSC-MR31 and hESC-H9 cell lines comparing the three tested differentiation conditions (flow cytometry analysis; n=3). FIG. 1C-D, Flow cytometry plots (n=3) of EVC derivatives assessing expression of (1C) pluripotent markers Tra-1-60 and Tra-1-81, and (1D) CD105, CD146. FIG. 1E, EVC differentiation efficiency from hPSC lines per 1 million input hPSCs. FIG. 1F, Flow cytometry plots (n=3) of EVC derivatives assessing expression of VEcad double labeled with CD105 or PDGFRβ. Isotype controls on the left panel. FIG. 1G, Quantitative real time RT-PCR analysis of EC and perivascular marker expression by EVCs and sorted VEcad$^+$ and VEcad$^-$ cells. # denotes 'not detected'. Data is normalized to EVCs of each specific hPSC type. FIG. 1H, Flow cytometry plots (n=3) of hematopoietic marker CD45 (hiPSC-BC1). FIG. 1I, Quantitative real time RT-PCR of H9-EVCs for the expression of SMMHC and peripherin, compared to undifferentiated cells (d0) and mature derivatives (Wanjare et al. (2012); Lee et al (2010)). Isotype controls for flow cytometry are in gray. Flow cytometry results shown are typical of the independent experiments. Significance levels were set at *p<0.05, p<0.01, and *p<0.001.

FIG. 2A-2D shows EVC maturation. FIG. 2A, sorted VEcad+ from hiPSC-BC1-derived EVCs sub-cultured for an additional 6 days in SB431542-supplemented conditions and analyzed for the expression of VEcad, CD31 and CD146 (representative flow cytometry plots; n=3); FIG. 2B, sub-cultured sorted VEcad+ exhibited membrane localization of CD31 and VEcad, cytoplasmic expression of eNOS, punctuated vWF, and uptake of AcLDL. FIG. 2C, hiPSC-BC1-derived EVCs sub-cultured for an additional 6 days in pericyte-inducing conditions (Orlidge and D'Amore, 1987) were analyzed for the expression of NG2, CD73, PDFGRβ, CD44, CD146 and CD105 via flow cytometry. In FIG. 2D cells exhibited appropriate localization of PDGFRβ, NG2 and calponin as demonstrated via immunofluorescence. Results shown are typical of the independent experiment. Scale bars are 100 µm.

FIG. 3A-3F shows self-assembly of EVCs to multicellular networks in three dimensional matrix. FIG. 3A shows network formation from EVCs in (i) collagen and (ii) HA hydrogels. FIG. 3B shows sorted VEcad+ and VEcad− cells encapsulated within collagen gels were unable to form networks (VEcad− insert is an example of a cell with typical stellate morphology); scale bars are 100 µm. FIG. 3C shows that vacuole formation was observed after one day as evident by: (i) light microscopy (LM) and (ii) confocal images of vacuole vital stain, FM4-64. Scale bar is 10 µm. FIG. 3D shows that on day 2, network formation with (i-ii) enlarged lumen and (iii-iv) cell sprouting were visualized by LM images. Scale bar in (i) and (iii) are 10 µm; in (ii) is 20 µm; and in (iv) is 50 µm. FIG. 3D shows that on day 3, complex networks were observed with enlarged and open lumen as indicated by confocal z-stacks and orthogonal sections of FM4-64. Scale bar is 20 µm. FIG. 3F shows that after 3 days, multilayered structures were also detected as demonstrated by 3D projection image of NG2, phalloidin, and nuclei showing NG2+ pericyte integrated onto hollow structures. Images shown are typical of the independent experiment. Scale bars are 50 µm.

FIG. 4A-4F shows perfusion of EVC networks in vivo in synthetic hydrogels. FIG. 4A-B shows that confocal images of two week explants of (4A) BC1-EVC or (4B) GFP-hiPSC-EVC networks in HA hydrogels demonstrate incorporation of human cells into host vessels (tail-vein injected, mouse specific (4A) Alexa Fluor 488-conjugated or (4B) Alexa Fluor 546-conjugated GS-IB4 lectin) and human cells exhibiting pericyte behavior (arrowheads). Scale bars are 50 µm. (i and ii: high mag of indicated regions) FIGS. 4C and 4D show histological examinations of the explants stained for CD31 expression via (FIG. 4C) immunofluorescence (CD31, red blood cells, and DAPI in red, green, and blue respectively; scale bar is 10 µm) and (FIG. 4D) immunohistochemistry (scale bar is 50 µm) reveal functional vessels containing human CD31+ cells with perfused blood cells. *perfused human vessel; #perfused mouse vessel FIG. 4E shows that quantification of cross-sectional areas and vessels per mm$^2$ of microvasculature containing human CD31+ cells depicts large perfused vessels and smaller non-perfused vessels in explants. FIG. 4F shows that immunofluorescence staining of sectioned explants for NG2+ cells reveals functional human pericytes wrapping perfused vessels. Scale bar is 10 µm.

(FIG. 8C) EVCs were also derived from a GFP transgenic hiPSC line (Haase et al., 2009) and confirmed for their marker expression profile by flow cytometry. (FIG. 8D) Flow cytometry analysis of CD105, CD146, and VEcad in hPSCs differentiated for 12 days lacking supplementation of VEGF or SB431542. Results shown are typical of the independent experiments.

FIG. 9a, hPSCs were differentiated in monolayer for 6 days followed by an additional 6 days in medium supplemented with and without SB431542 in low and high VEGF concentrations and analyzed using flow cytometry (n=3) for Tra-1-60 expression. Tra-1-60 expression was downregulated in all conditions examined. FIG. 9b, H9-EVCs differentiated in media supplemented with SB431542 and using high VEGF concentrations were analyzed for the expression of Tuj1 using quantitative real time RT-PCR compared to undifferentiated cells (d0) and mature derivatives (Lee et al., 2010). Significance levels were set at *p<0.05, p<0.01, and *p<0.001. Data are reported ±SEM. FIG. 9C shows PDGFRβ and VEcad expression in H9 EVCs. H9-EVCs differentiated in media supplemented with SB431542 and using high VEGF concentrations were double labeled for PDGFRβ and VEcad and analyzed via flow cytometry. Results shown are typical of the independent experiments.

FIG. 11A-11E shows EC maturation. hiPSC-MR31-derived EVCs were sub-cultured for an additional 6 days in 50 ng/ml VEGF and SB431542-supplemented conditions and analyzed for (11A) the expression of VEcad and CD31 expression (representative flow cytometry plots; n=3); and (11B) membrane localization of VEcad and CD31, cytoplasmic expression of vWF and eNOS and uptake of acLDL. (11C) Representative flow cytometry plots (n=3) of VEcad and CD31 expression in hiPSC-BC1- and hESC-H9-derived EVCs subcultured for an additional 6 days in SB431542-supplemented conditions. Isotype controls for flow cytometry are in gray. (11D-E) VEcad+ cells from EVCs of the different hPSC-lines were sub-cultured for an additional 6 days in SB431542-supplemented conditions and analyzed for (11D) the expression of I-cam in response to TNFα and (11E) network formation on Matrigel (hiPSC-MR31). Significance levels were set at *p<0.05, p<0.01, and *p<0.001. Data are reported ±SEM FIG. 12 shows sorted VEcad– cells. Sorted VEcad– cells from hiPSC-BC1-derived EVCs sub-cultured for an additional 6 days in SB431542-supplemented conditions and analyzed for the expression of VEcad, CD31, and PDGFRβ (representative flow cytometry plots; n=3). Isotype controls for flow cytometry are in gray. Results shown are typical of the independent experiments.

FIG. 13A: hiPSC-BC1-derived EVCs were negative for pericyte marker, NG2 (representative flow cytometry plots; n=3).

FIG. 14a, EVC derivatives (hESC-H9) were encapsulated in collagen gels and cord-like structure formation was observed during the culture period. Scale bars are 100 µm. EVCs were also derived from a GFP transgenic hiPSC line (Haase et al., 2009) and confirmed for their marker expression profile by flow cytometry.

FIG. 16A-16C shows vacuole formation after 1 day HA encapsulation. BC1-EVCs were encapsulated in HA hydrogels and visualized via light microscopy after 1 day. (FIG. 16A shows vacuole formation on day 1 via (i) low magnification (scale bar=100 µm; some vacuole are indicated by arrowheads) and (ii) high magnification of individual cells (scale bar is 5 µm). FIG. 16B shows BC1-EVC sorted VEcad⁺ subpopulation encapsulated in HA gels were able to form vacuoles whereas FIG. 16C illustrates BC1-EVC sorted VEcad– subpopulation were not. Scale bar in B, C are 10 µm. Images shown are typical of the independent experiments.

FIG. 17A-17B shows matrix from day 2 to 3. BC1-EVCs were encapsulated in HA hydrogels and the kinetics of network formation was documented with (17A) sprouting and initial network formation on day 2 as indicated by serial confocal z-stack images of vacuole vital stain, FM4-64 and nuclei (scale bar is 50 µm); and (17B) complex networks on day 3 as indicated by (i) light microscopy (scale bar is 100 µm), with enlarged and open lumen as indicated by (ii) confocal z-stacks and (iii) orthogonal sections of vacuole vital stain, FM4-64 and nuclei. Images shown are typical of the independent experiments.

FIG. 18A-18C shows derived pericytes in the vascular networks. EVCs were encapsulated in HA hydrogels and after three days in culture, multilayer structures were detected as demonstrated by confocal microscopy of NG2 (green), vacuole vital stain FM4-64 (red), and nuclei (blue) showing (FIG. 18A) pericytes integrated onto a hollow tubular structure (three dimensional projection) and (FIG. 18B) enclosing a luminal structure (confocal z-stack). FIG. 18C, Flow cytometry analysis (n=3) confirms that EVCs cultured in HA hydrogel culture media for three days acquire NG2 expression. Images shown are typical of the independent experiment. Inset is isotype control. Scale bar is 20 µm.

FIG. 19A-19C 19 shows in vivo functionality of EVCs. EVCs derived from (FIG. 19A) BC1 and (FIG. 19B) MR31 were dyed with PKH-26, implanted subcutaneously in Matrigel (MG) plugs and explants were analyzed after one week. Representative confocal z-stack images of perfused explants with fluorescein-conjugated GS-IB-4 lectin (green) show that EVCs integrated into host vasculature after one week (human cells in red). Some human vessels were not perfused (asterisk). Nuclei in blue. FIG. 19C, Histological examination of BC1-MG explants after 1 week reveals functional microvasculature containing human CD31+ cells as indicated by blood cell perfusion. Scale bar is 50 µm.

FIG. 20A-20B shows EC and pericyte phenotypes in in vivo explants of BC1-EVC HA constructs. EVCs derived from BC1 were dyed with PKH-26, encapsulated in HA hydrogels, and cultured for 3 days, after which were implanted subcutaneously. Confocal z-stack images of two week explants perfused with fluorescein-conjugated GS-IB-4 lectin showing human cells interacting with the host vessels via (FIG. 20A) incorporation into and (FIG. 20B) wrapping around penetrating host vessels.

FIG. 21A-21C shows derived pericytes in vivo. FIG. 21A, Confocal images of two week explants of BC1-EVC networks in HA hydrogels reveals functional human NG2+ pericytes proximal to host vessels in two week explants. Human cells are in red (PKH26). FIGS. 21B-C, Histological examination of in vivo explants of hESC-H9-EVC networks in HA hydrogels after two weeks also depict NG2+ pericytes wrapping perfused vessels via (FIG. 21B) immunofluorescence staining on cross sections of explants. Scale bar is 20 µm, and (FIG. 21C) immunohistochemistry for NG2 (an example is indicated by arrow). Scale bar is 10 µm.

FIG. 23A-23D shows Analysis of hPSC-derived perivascular cells. Derivatives were analyzed for: (A) proliferation using (i) stain for Ki67 and (ii) corresponding image quantification; (B) morphology using (i) light microscopy and (ii) FM4-64 membrane stain and dapi; (C) corresponding image quantification of (i) cell and (ii) nuclei area; and (D) sub-cellular organelle organization using TEM. CIV=Collagen type IV; ER=endoplasmic reticulum; mitoch=mitochondria. Scale bars in E are 1 µm. All graphical data are reported as mean±SEM. *p<0.05, p<0.01, and *p<0.001.

FIG. 26A-26D shows a Comparison of functionalities demonstrated by perivascular derivatives. (A) Differentiation potential of perivascular derivatives into mesenchymal lineages including adipocytes (Oil Red O stain) and osteoblasts (Alizarin Red S stain). (B) One-week subcutaneously transplanted perivascular derivatives (in red; PKH26) migrated to newly formed host blood vessels (mouse ECs in green (Alexa-488 conjugated isolectin IB4) within Matrigel, as indicated by representative confocal images. White arrows indicate occasions of circumferential wrapping of vasculature by the transplanted hiPSC derivatives; nuclei (DAPI). (C) Migration potential via a wound healing assay: (i) phase contrast images quantified for (ii) cell trajectories and (iii) speed. (D) Downward invasion of hiPSC perivascular cells through collagen gels towards ECs was examined after 48 h via (i) cross section of toluidine blue dyed cells and (ii) quantification of the cell number, distance of invasion, and (iii) the average distance traveled. All graphical data are reported as mean±SEM.*p<0.05, p<0.01, and *p<0.001.

FIG. 27A-27C shows marker assessment of perivascular derivatives related to FIG. 22. (A) Quantitative real time RT-PCR analysis of mesoderm (in solid lines) and neural crest (in dashed lines) genes at days 0, 3 and 6 along differentiation for BC1 and H9. (B-C) H9 differentiating cells analyzed for (B) marker expression by flow cytometry analysis of day 6 differentiating cells, EVCs, and SMLCs (isotype control in gray) and (B) perivascular cell and nuclei area.

FIG. 29A-29C shows perivascular marker expression in control cells related to FIG. 24. Organization of (A) SMA and NG2 and (B) SMMHC and PDGFRβ in aortic vSMCs and placenta pericytes. (C) Expression of NG2, SMMHC, PDGFRβ and caldesmon in the different cell types compared to aortic vSMCs starved in low serum using quantitative real time RT-PCR. *P<0.05; P<0.01; *P<0.001.

FIG. 30A-30D shows ECM in control cells related to FIG. 25. (A) Deposition of the ECM proteins collagen I, collagen IV, fibronectin, and laminin in placenta pericytes and aortic vSMCs. (B) Elastin organization in aortic vSMCs showing interacellular (left column) and extracellular (right column) deposition. (C-D) Expression of fibronectin, ED-A fibronectin and elastin, in the different cell types (compared to aortic vSMCs starved in low serum) using quantitative real time RT-PCR. *P<0.05; P<0.01; *P<0.001.

DETAILED DESCRIPTION OF THE INVENTION

Embodiments of the invention are discussed in detail below. In describing embodiments, specific terminology is employed for the sake of clarity. However, the invention is not intended to be limited to the specific terminology so selected. While specific exemplary embodiments are discussed, it should be understood that this is done for illustration purposes only. A person skilled in the relevant art will recognize that other components and configurations can be used without parting from the spirit and scope of the invention. All references cited herein are incorporated by reference as if each had been individually incorporated.

Derivation of EVCs from hPSCs

Figure 5:
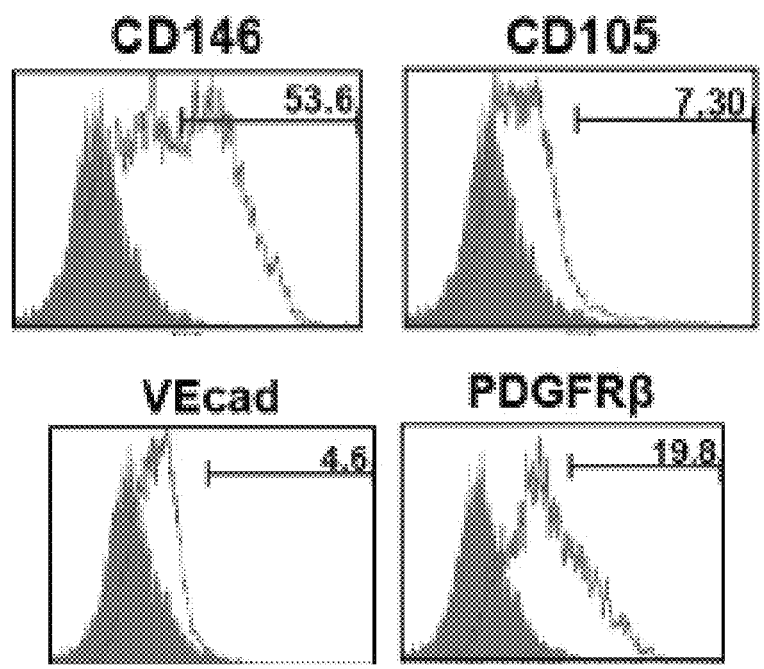
FIG. 5 shows differentiating hPSCs. hiPSC-BC1 were differentiated in monolayer for 6 days and analyzed using flow cytometry analysis (n=3) for markers of interest including CD146, CD105, VEcad, and PDGFRβ. Results shown are for hiPSC-BC1 cell line and typical of the independent experiments.
Figure 6:
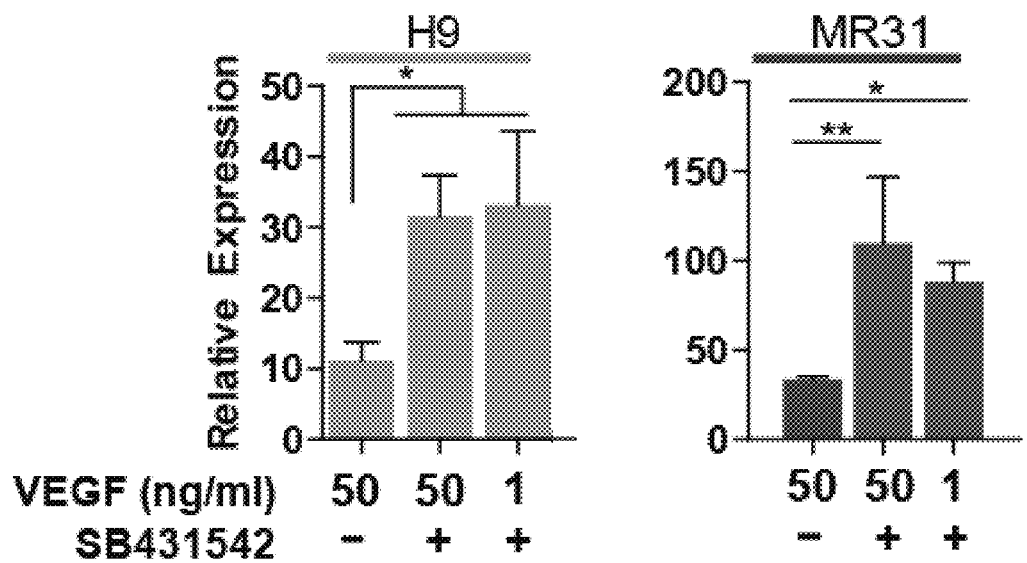
FIG. 6 shows the effect of VEGF and TGFβ inhibitor on VEcad expression. hPSCs were differentiated in monolayer for 6 days followed by an additional 6 days in medium supplemented with and without SB431542 in low and high VEGF concentrations and analyzed using real-time PCR for VEcad expression (n=3). VEcad expression was upregulated with the addition of TGFβ inhibitor independently of VEGF concentrations in all hPSC lines tested. Significance levels were set at *p<0.05, p<0.01, and *p<0.001. Data are reported ±SEM.
Figure 7:
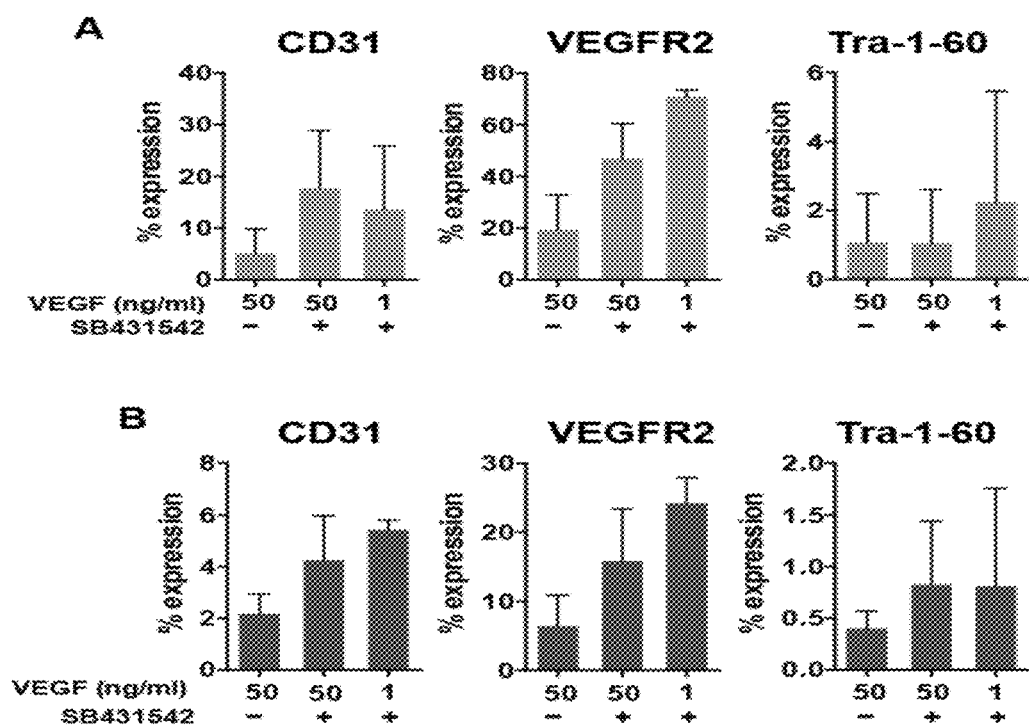
FIG. 7 shows the effect of VEGF and TGFβ inhibitor on CD31, VEGFR2 and Tra-1-60 expression. hPSCs were differentiated in monolayer for 6 days followed by an additional 6 days in medium supplemented with and without SB431542 in low and high VEGF concentrations and analyzed using flow cytometry (n=3) for CD31, VEGFR2, and Tra-1-60 expression in (A) hESC-H9 and (B) hiPSC-MR31 lines. CD31 expression did not change in the different treatments, while VEGFR2 expression was upregulated in media supplemented with low VEGF concentration. Tra-1-60 expression was downregulated to <1% in conditions supplemented with high VEGF. Data are reported ±SEM.

Toward clinically relevant outcomes and because microvascular architecture is a bicellular entity, we first sought to develop a robust and controlled method to differentiate hPSCs into a bicellular vasculogenic population with maturation capacity to both endothelial cells (ECs) and pericytes. CD105 and CD146 are common to both cell types (Dar A, et al. (2011); Duff et al. (2003); Bardin N, et al. (2001); Airas L, et al. (1995)), whereas vascular endothelial cadherin (VEcad) has been shown to specify lineage commitment of ECs (James et al., 2010), Though no single marker denotes a pericyte, it can be distinguished by expression of platelet derived growth factor β (PDGFRβ) in conjunction with CD146 (18). Acknowledging that co-cultures of pericytes and ECs typically result in pericyte-mediated EC growth inhibition (Dar et al., 2011; Orlidge and D'Amore, 1987), we focused on inducing VEcad+ cells early on in the differentiation scheme to ensure EC maturation. The present invention utilizes a step-wise differentiation procedure to induce vascular lineage specification, going beyond prior reported methods (James D, et al. (2010); Gerecht et al. (2003); Yamashita J, et al. (2000)) Human PSCs (H9, MR31, BC1 and GFP-hiPSC as listed in Table 1) were first allowed to undergo differentiation in monolayer (as seen in FIG. 5). The subsequent addition of transforming growth factor β inhibitor, SB431542 (James et al., 2010), supplemented with either high (50 ng/ml) or low (1 ng/ml) vascular endothelial growth factor-A (VEGF-A) concentrations yielded upregulation of VEcad expression, ranging from 20-60% VEcad+ cells (see FIG. 1B and FIG. 6) depending on hPSC line. Utilizing one embodiment of the present invention, human ESC line H9 exhibited the greatest potential to yield the largest percentage of VEcad+ cells compared to hiPSC line BC1 and MR31 under our differentiation strategy. The expression levels of CD31 were not altered at the different conditions while VEGF receptor-2 (VEGFR2/KDR) expression was higher in media supplemented with a low VEGF concentration (shown in FIG. 7). Expression of Tra-1-60 and Tra-1-81, markers of pluripotency, was <1% when using high VEGF concentrations, indicating the vast majority of cells had been differentiated (see FIG. 1C and FIG. 7A). Thus, for all studies EVCs were differentiated in media supplemented with SB431542 and using high VEGF concentrations.

TABLE 1

| hPSC line | Type | Reprogramming factors | Source | Ref. |
|---|---|---|---|---|
| H9 | hESC | — | blastocyst | (Thomson, 1998) |
| H13 | hESC | — | blastocyst | (Thomson, 1998) |
| MR31 | hiPSC | OSK | IMR90 (normal, fetal lung fibroblasts, XX) | (Mali et al., 2010) |
| MMW2 | hiPSC | OSKM | MSC1640 (normal MSCs from 24 y/o, XY) | (Zou et al., 2011) |
| BC1 | hiPSC | Plasmid encoding OSKML | CD34+ cells from bone marrow | (Cheng et al., 2012; Chou et al., 2011) |
| GFP-hiPSC | hiPSC | OSLN | Cord blood-derived ECs | (Haase et al., 2009) |

O=OCT4; S=SOX2; K=KLF4; M=c-MYC; L=LIN28; N=NANOG

Figure 8:
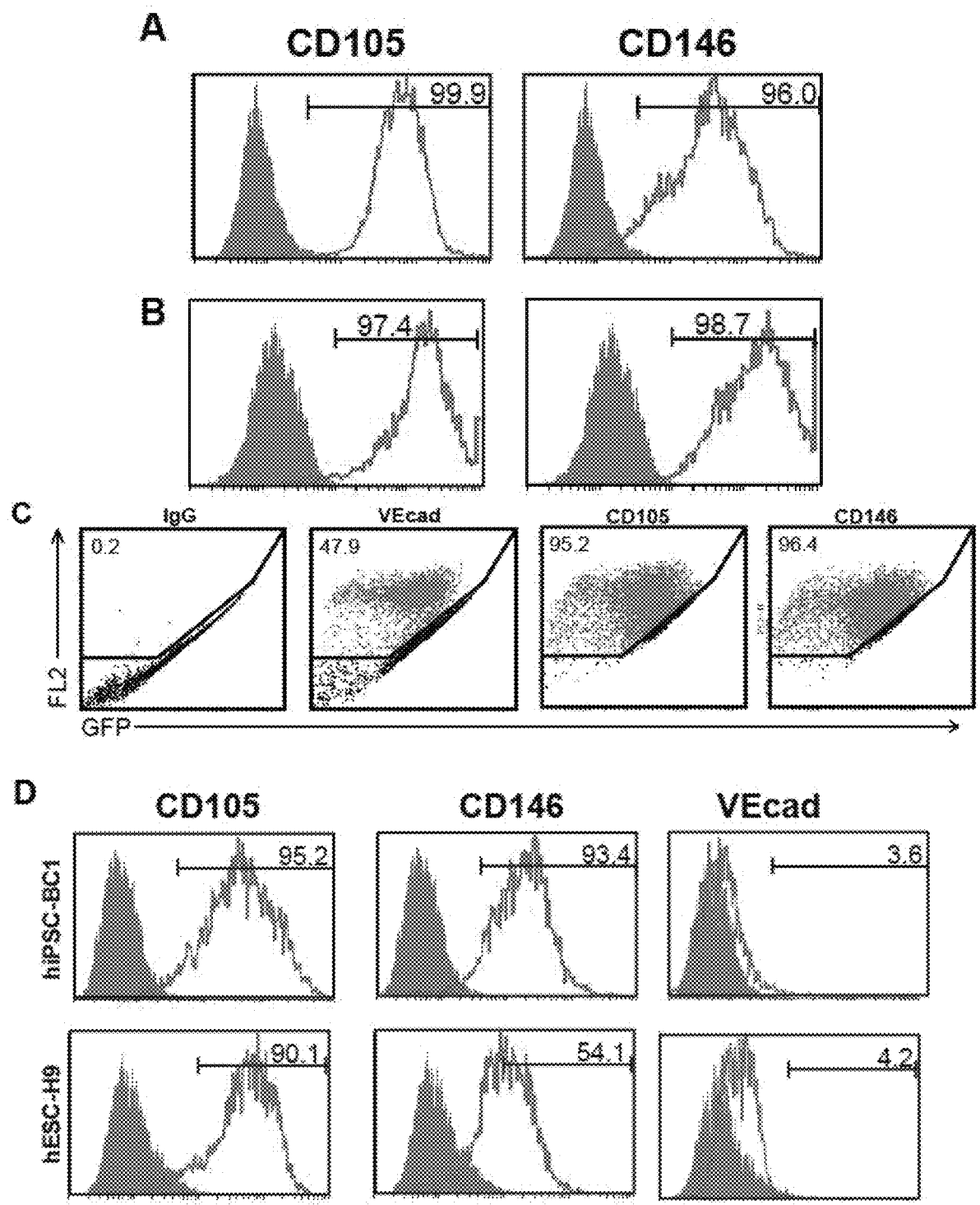
FIG. 8A-8D shows marker expression in EVCs. hPSCs were differentiated in monolayer for 12 days and EVC derivatives were analyzed using flow cytometry (n=3) assessing co-expression of CD105, CD146, CD73 with VE-cad from (FIG. 8A) hESC-H9 and (FIG. 8B) hiPSC-BC1 differentiated cells.

According to embodiments of the invention, EVCs derived from multiple hPSC lines using high VEGF concentrations and SB431542 can be highly purified (>95%) for CD105 and CD146, surface antigens common to both ECs and pericytes (FIG. 1D; FIG. 8A-C). Previous approaches sorted out a CD105+ population from spontaneously differentiating EBs with a focus toward pericytes (Wanjare M, e al. (2012)). By eliminating the sorting step and guiding hPSCs toward a bipotent population, the present invention provides a new concept yielding a CD105+CD146+ population in a controlled, efficient and robust manner that comprises the bicellular microvascular architecture. In the absence of the protocol described herein (i.e. removal of VEGF and SB431542 supplementation), hiPSC-BC1 cells differentiated for 12 days were still fairly enriched in CD105 (95%) and CD146 (93%); however, hESC-H9 cells differentiated for 12 days without use of the present invention expressed approximately 90% CD105+ cells and only 54% CD146+ cells (FIG. 8D). Importantly, both H9 and BC1 differentiated cell populations expressed very low levels of VEcad. These results, in addition to the finding that high VEGF supplementation ensures <1% Tra-1-60+ cells in the various hPSC types (from FIG. 1C, FIG. 7), demonstrate additional unexpected advantages of the of inductive media conditions utilizes according to the present invention.

Figure 9:
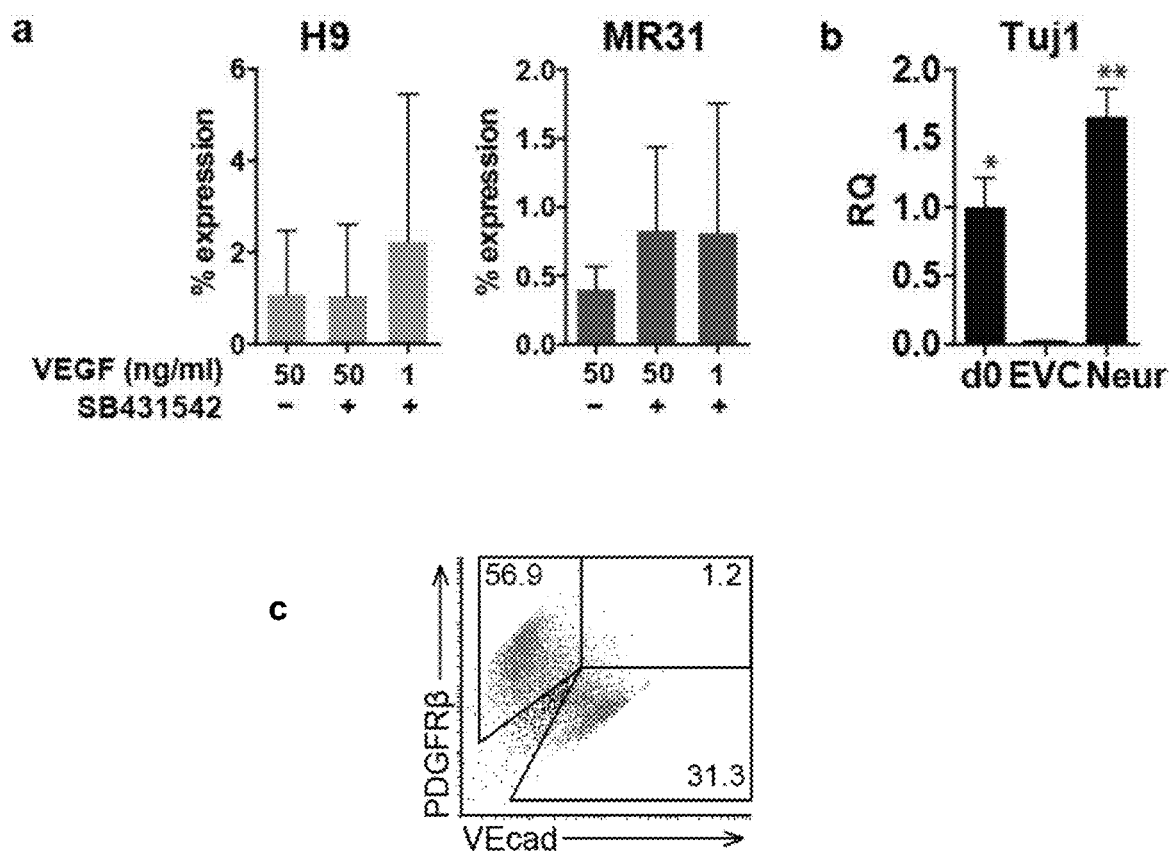
FIG. 9A-9C shows pluripotent and neuronal marker expression in EVCs.

Thus, according to embodiments of the present invention, CD105+CD146+ EVCs at an approximate ratio of 1:1 of input hPSC to EVC (FIG. 1E) can be derived. The number of input hPSCs is calculated as the number seeded at day 0 (and not the number of cells present after 1 day of differentiation) as in previously reported methods (James D, et al. (2010)). The yield of VEcad+ cells in EVCs can vary among cell lines, ranging from approximately $8\times10^4$ to $2.5\times10^5$ per $10^6$ hPSCs (FIG. 1E), similar to what has been recently reported for KDR+ EC derivatives (White M P, et al. (2013)). Flow cytometry analysis of EVCs double labeled with antibodies against CD105 and VEcad confirmed that a subset of cells co-expressed CD105 and VEcad (FIG. 1F left). In contrast, EVCs double labeled for VEcad and PDGFRβ revealed two distinct VEcad+PDGFRβ$^{lo}$ and VEcad-PDGFRβ+ populations (FIG. 1F right; FIG. 9C). RT-PCR analysis of sorted VEcad+ and VEcad− subpopulations from EVCs revealed distinct phenotypes (FIG. 1G). VEcad+ cells from both hESC-H9 and hiPSC-BC1 cell lines demonstrated greater expression of EC markers VEcad and CD31 compared to unsorted EVCs and sorted VEcad− subpopulation. Notably, endothelial nitric oxide synthase (eNOS)—a mature EC marker—was highly expressed in H9-VEcad+ cells compared to H9 EVCs and sorted VEcad− cells, whereas eNOS was undetected in all tested BC1 samples. Sorted VEcad− cells exhibited greater expression of pericyte markers, PDGFRβ and NG2, compared to EVCs and sorted VEcad+ cells. These analyses also reveal differences in the differentiation potential between hESC-H9 and hiPSC-BC1 lines using the adherent, step-wise differentiation protocol; they suggest that hESC-H9 differentiating cells may mature more rapidly toward these lineages due to the finding that 12-day differentiated H9-EVCs start to express eNOS at the mRNA level and yielded a greater percentage of VEcad+ (from FIG. 1B) and CD31+ cells at the protein level (from FIG. 7) compared to the tested hiPSC lines.

Figure 10:
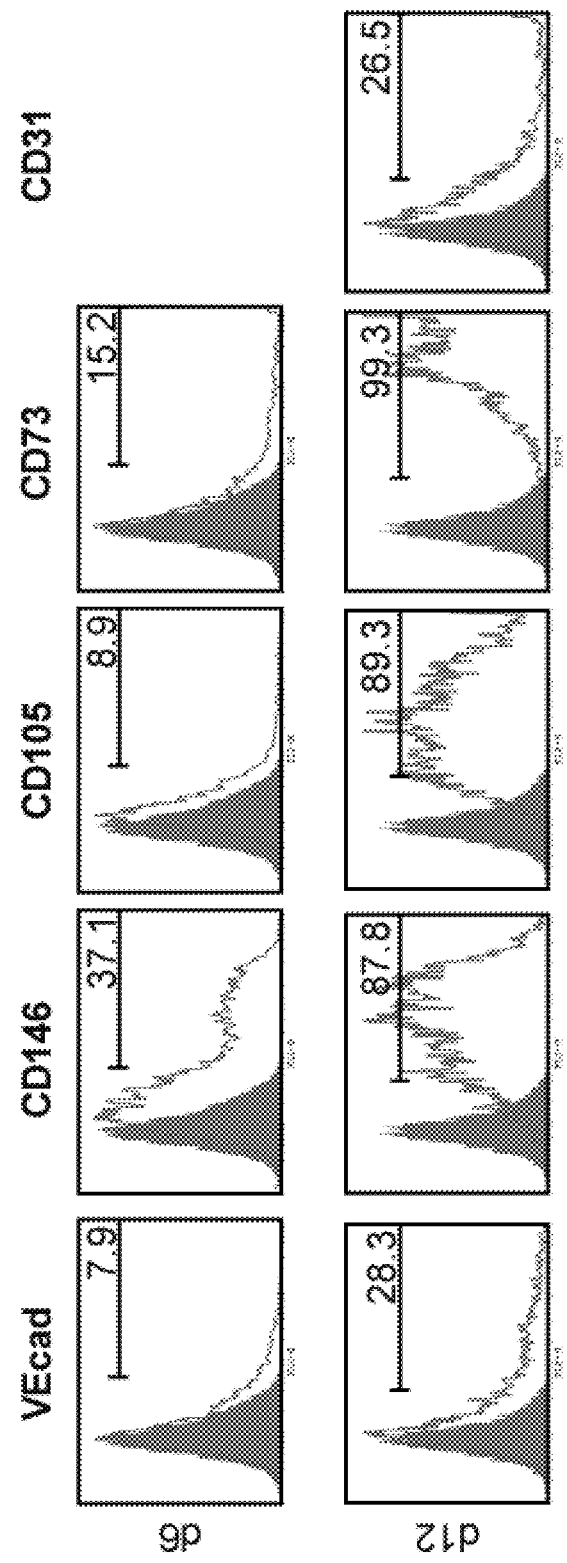
FIG. 10 shows EVCs derived using serum-free conditions. Flow cytometry (n=3) analysis of hiPSC-BC1-derivatives after 6 and 12 days of differentiation in serum-free conditions reveals marker expressions comparable to that of the standard differentiation scheme. Results shown are typical of the independent experiments.

EVCs were negative for hematopoietic marker CD45 (FIG. 1H), and demonstrated negligible expression of smooth muscle cell marker, smooth muscle myosin heavy chain (SMMHC), as well as peripheral neuron marker, peripherin (FIG. 1I and FIG. 9b). Comparable marker expression profiles were obtained from EVCs derived using serum free conditions in our adherent differentiation scheme (see FIG. 10). Thus, this derived population can be considered to be vascular lineage specific and comprised of early ECs and early pericytes. It should be noted that these are not mature ECs and pericytes, as only twelve days of differentiation is not sufficient to mature hPSCs toward matured phenotypes, in agreement with numerous previous studies (Dar A, et al. (2011); Wang L, et al. (2004); Ferreira L S, et al. (2007)).

Differentiation Protocol.

Human PSCs were collected through digestion with ethylenediaminetetraacetic acid (EDTA; Promega), separated into an individual cell suspension using a 40-μm mesh strainer (BD Biosciences) and plated onto collagen IV (Trevigen) coated plates at a concentration of $5 \times 10^4$ cells/cm$^2$. Cells were cultured for 6 days in a differentiation medium composed of alpha-MEM (Invitrogen), 10% FBS (Hyclone) and 0.1 mM β-mercaptoethanol (β-ME), with the media changed daily. On day 6, differentiated cells were collected through digestion with TrypLE (Invitrogen), separated with a 40-μm mesh strainer, and seeded at a concentration of $1.25 \times 10^4$ cells/cm$^2$ on collagen-type-IV-coated plates in endothelial cell growth media (ECGM) (Promo-Cell) supplemented with 2% FBS, 50 ng/ml VEGF with or without TGF-β (10 μM SB431542 (Tocris)), or 1 ng/ml VEGF+10 μM SB431542 for 6 days. Media was changed every other day. To elucidate whether serum-free conditions could be used to derive EVCs, we followed the aforementioned protocol except differentiating the cells in alpha-MEM media supplemented with 20% knockout serum replacement, 0.1 mM β-ME, 1× non-essential amino acids (Gibco), and 1× L-glutamine (Invitrogen) for 6 days, followed by 6 days in ECGM base media (Promocell) supplemented with 50 ng/ml VEGF, 10 μM SB431542, 10% knockout serum replacement, β-ME, essential amino acids, and glutamine. For this process the plates can be coated with a variety of suitable materials which include type I collagen and fibronectin as well as type IV collagen. SB431542 is a convenient TGF-β inhibitor for this process. Other TGF-β inhibitors or siRNA inhibition of TGF-β are also operational.

Maturation of EVCs: ECs

To examine the endothelial potential of hPSC-EVCs, two approaches were examined: we either sub-cultured EVCs or sorted and expanded VEcad+ cells, both under the same culture conditions (i.e., 50 ng/ml VEGF and SB431542). Sub-culturing yielded ECs that were enriched in VEcad and CD31 (FIGS. 11A, B); however, this approach and enrichment without cell sorting varied among three different hPSC lines; a hiPSC line with vector integration gave rise to the best result as seen in FIG. 11C. Sorted VEcad+ cells from EVCs matured toward VEcad+CD31+CD146+ ECs as shown in FIG. 2A. The cells exhibited typical membrane expression of VEcad and CD31, lectin binding, cytoplasmic expression of eNOS and von Willebrand factor (vWF), uptake of acetylated low density lipoprotein (AcLDL), upregulation of intercellular adhesion molecule 1 (ICAM1) in response to tumor necrosis factor α, and network formation on Matrigel (FIG. 2B, and FIG. 11D). Lectin, eNOS, vWF, or acLDL uptake via immunofluorescence could not be detected in unsorted EVC populations, revealing that no subpopulation of EVCs expresses these EC characteristics and additional culture is necessary to mature early ECs from EVCs. These data were consistent among the different hPSC lines examined.

Maturation of EVCs: Pericytes

Figure 13:
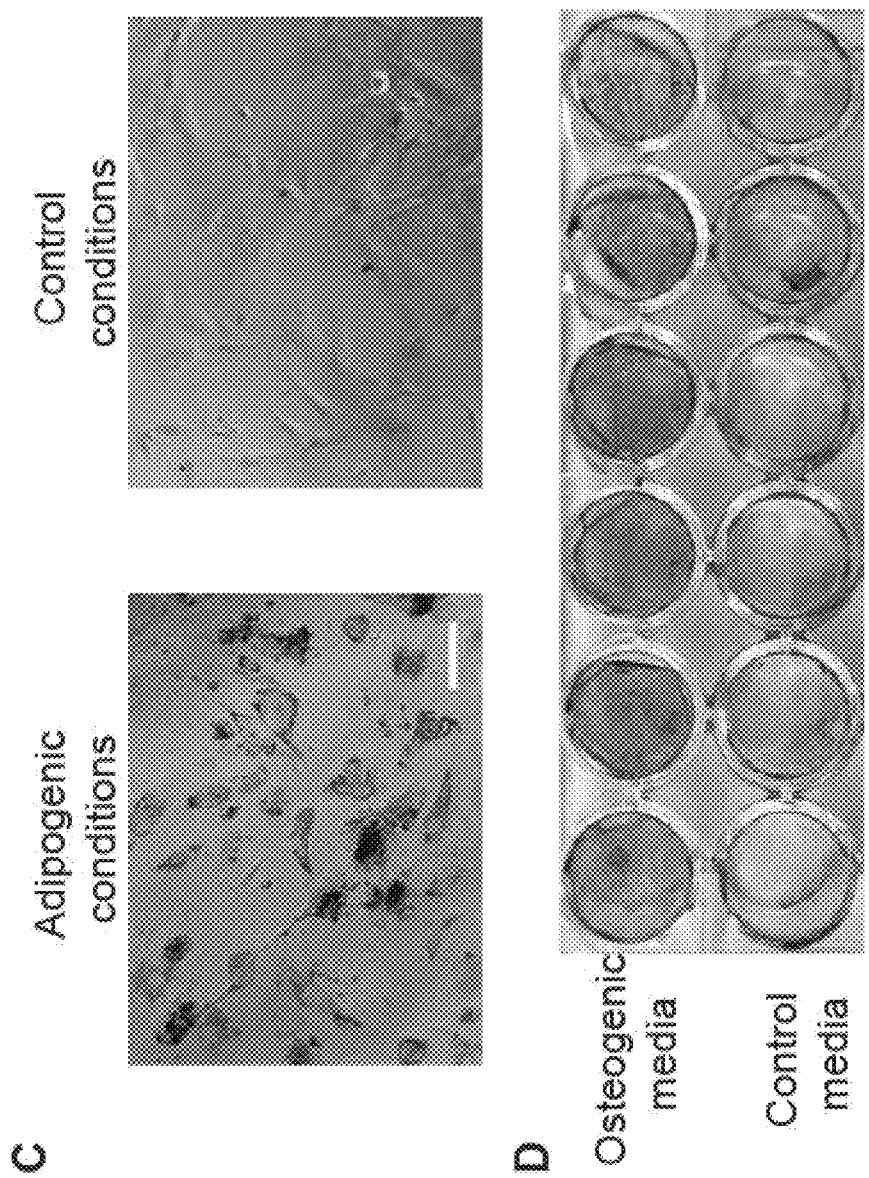
FIG. 13A-13O shows pericyte maturation and mesenchymal differentiation potential.
FIG. 13B: hiPSC-BC1-derived EVCs sub-cultured for an additional 6 days in pericyte-inducing conditions (Orlidge and D'Amore, 1987) were analyzed for the expression of CD31 and VEcad via flow cytometry (representative flow cytometry plots; n=3). Results shown are typical of the independent experiments.
(FIGS. 13C,D) Derived pericytes differentiated into mesenchymal lineages including (13C) adipocytes (Oil Red O stain) and (13D) osteoblasts (Alizarin Red S stain). Scale bar is 50 µm.
Figure 14:
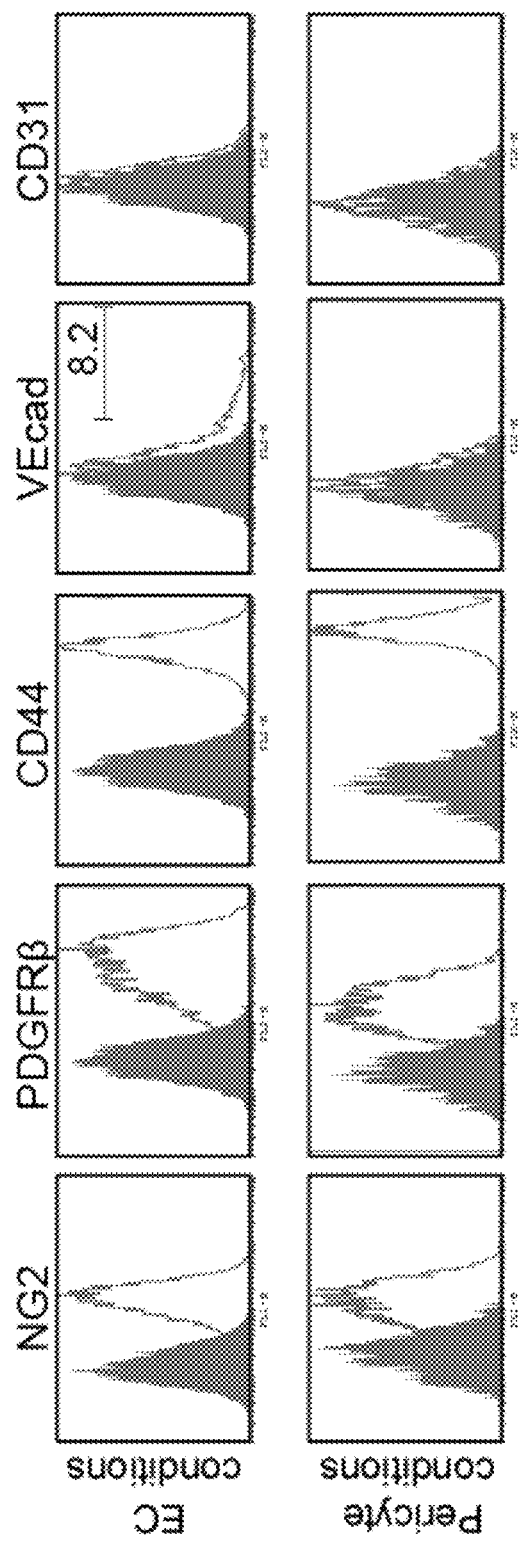
FIG. 14 shows sorted VEcad⁻ cells from hiPSC-BC1-derived EVCs sub-cultured for an additional 6 days in EC conditions (50 ng/ml VEGF and SB431542) or pericyte maturation conditions analyzed for the expression of NG2, PDGFRβ, CD44, VEcad, and CD31 (representative flow cytometry plots; n=3). Results shown are typical of the independent experiments.

EVCs, which do not express NG2 (FIG. 13A), were cultured under pericyte-inducing conditions (Orlidge and D'Amore, 1987). After 6 days of culture, the cells were enriched in pericyte markers CD73, NG2, PDGFRβ, and CD44 (Crisan et al., 2012) and depleted in EC markers VEcad and CD31 (FIG. 2C and FIG. 13A). Surprisingly, most cells remained CD146+, but some cells lost CD105 expression (FIG. 2Cc). The spindle-shaped pericyte derivatives expressed PDGFRβ and NG2 proteoglycan and exhibited filamentous calponin expression (FIG. 2d), as expected for pericytes derived from fetal and adult sources. Sorted VEcad+ cells were unable to attach and grow under pericyte-maturing conditions. An important functionality of pericytes is their ability to behave as mesenchymal precursors (Crisan et al., 2008; Dar et al., 2011). Indeed, the pericyte derivatives in our culture could be differentiated to adipocytes and osteoblasts (see FIGS. 13B-C), demonstrating their mesenchymal potential. Furthermore, sorted VEcad− cells, cultured in either EC maturation conditions (50 ng/ml VEGF and SB431542) or pericyte-maturing conditions for 6 days, expressed NG2, PDGFRβ, and CD44 (FIG. 14). A small population (~8%) of sorted VEcad− cells acquired VEcad expression (but not CD31 expression) when cultured in EC maturation conditions, depicting some degree of cellular plasticity. Taken together, the cellular analyses demonstrate that EVCs, which are made up of CD105+CD146+, VEcad and CD105+CD146+PDGFRβ+ subtypes, contain the cellular makeup imperative to construct a functional microvasculature.

Self-Organization of Bicellular Vascular Networks in Hydrogels

Figure 15:
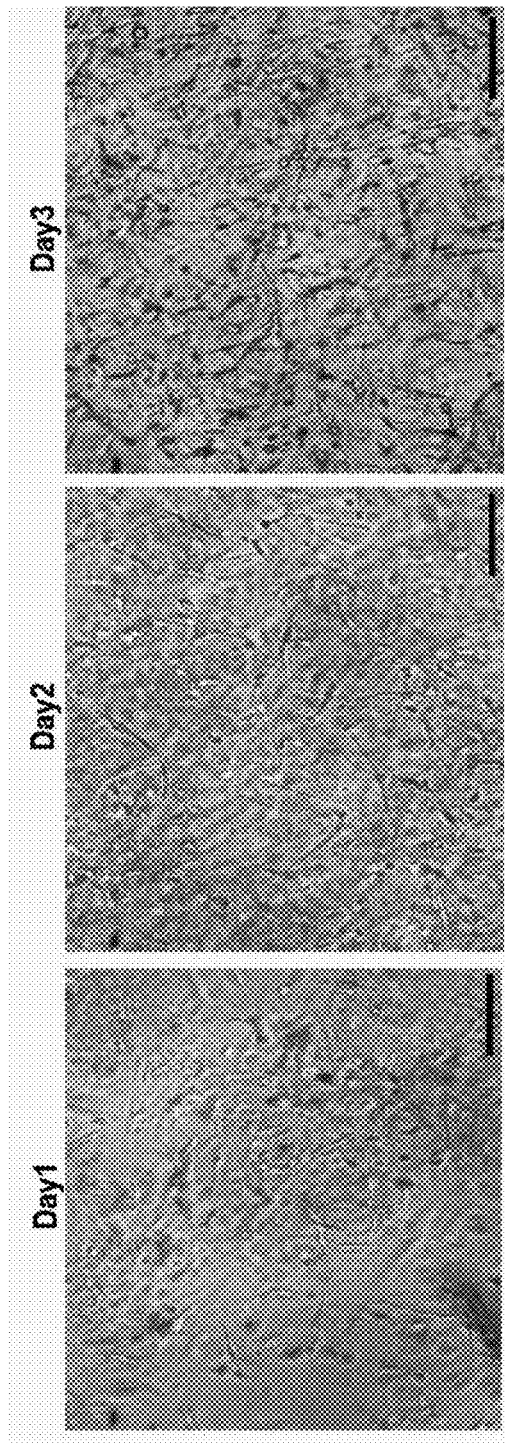
FIG. 15 shows cord formation by EVCs in collagen gels.

To examine whether EVCs could be leveraged to self-organize into a bicellular microvascular bed, network formation in collagen (Stratman et al., 2009a; Stratman et al., 2009b) and in completely synthetic hyaluronic acid (HA)-based hydrogel (Hanjaya-Putra et al., 2011) (FIG. 3A, and FIG. 15) was tested. We reasoned that derived EVCs would be able to work synergistically to form stable vascular networks in a three-dimensional matrix. Indeed, in both hydrogel systems, EVCs were found to form lavish networks (FIG. 3A); sorted VEcad+ or VEcad− cells were individually unable to form such networks when encapsulated within collagen gels (FIG. 3B). VEcad+ cells primarily formed vacuoles and started to form nascent structures within the collagen gel with some instances of sprouting (average circularity of 0.70±0.15 versus 0.36±0.23 for EVCs; FIG. 3B). The lack of robust network formation from derived ECs in collagen gels can be attributed to the lack of pericytes in culture and speculate that the addition of support cells help form the networks seen with EVC encapsulation. VEcad− cells exhibited cell spreading and a characteristic stellate morphology, but no network formation.

Vascular Morphogenesis of EVCs within HA Hydrogels

The progress of EVC network formation within the HA hydrogel, a xeno-free, synthetic, construct engineered to recapitulate tubulogenesis-inducing signals was examined (Hanjaya-Putra et al., 2011). In vitro assessment of cellular behavior revealed the formation of multicellular networks via a sequential process typical of vascular morphogenesis. After one day of culture, we observed vacuole formation in many, but not all, of the cells. Some of these vacuoles had coalesced into a larger structure, resembling lumen (FIG. 3A and FIG. 16A). To elucidate the phenotype of either cell type after one day, VEcad+ and VEcad− subpopulations were encapsulated independently. After one day, we could clearly observe vacuoles in the encapsulated sorted VEcad+ subpopulation; however, encapsulated sorted VEcad− cells primarily spread with no vacuole formation (FIG. 16B,C).

After 2 days of EVC encapsulation, we could observe the progression of tubulogenesis including extensive sprouting and occasions of open lumen (FIG. 3). By day 3, vascular networks grew; we clearly observed comprehensive multicellular networks within HA hydrogels. Complex vascular networks with patent lumen structures were easily detected throughout the hydrogels, suggesting a mature vascular network (FIG. 3C and FIG. 17A). Interestingly, on day 3 we could also observe instances of NG2+ pericytes incorporated in the luminal structures and encircling the forming tubular structures (FIG. 3D and FIG. 12).

Functionality of hPSC-Bicellular Vascular Constructs

Figure 4F:
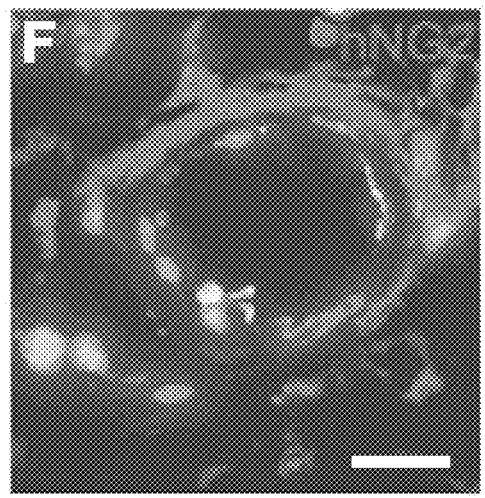

In vivo integration of vascular networks is crucial to the success of derived EVCs for regenerative medicine endeavors. We first tested whether EVCs will survive implantation, assemble into microvascular networks, integrate with the host vasculature, and establish blood flow. Using a Matrigel plug assay (Ferreira et al., 2007), human EVCs incorporated with perfused host microvasculature, as well as generated human-only microvascular structures (see FIG. 19). To harness the self-organizing capability of EVCs in HA hydrogels, the engineered microvascular networks were subcutaneously implanted and assessed the survival and integration assessed after two weeks. Human EVCs (derived from BC1 or a GFP-hiPSC line) were found to incorporate into or wrap around the mouse microvasculature (FIG. 4A and FIG. 20) and the hydrogels were largely degraded by two weeks. HA gels without encapsulated cells exhibited slower remodeling and degradation in vivo compared to gels with cells, as we have previously reported (Hanjaya-Putra D, et al. (2011)). Perfused microvasculatures (as indicated by tail-injected, mouse-specific fluorescein-conjugated GS-IB4 lectin) containing human ECs (with cross-sectional areas ranging from 100 to 25,000 µm$^2$) were abundant throughout the explant (~15 vessels per mm$^2$), demonstrating that the transplanted human vascular networks had anastomosed with the hosts' circulatory systems (FIGS. 4 C-E). Moreover, NG2+ human pericytes were found to migrate towards and encircle the perfused vasculature (FIG. 4F and FIG. 21).

The present bicellular constructs present several fundamental advancements to the future of cell-based therapies. Further investigations will focus on clinical translation, including understanding of the cells' interactions with one another and appreciation of the longevity and durability of the human vascular networks.

The balance between commitment and plasticity of the EVCs specifically within the vascular lineage allows for vascular fate and network maturation. This controlled system is reproducible, generates physiologically relevant vascular networks in implantable matrices, and thus presents the next fundamental step toward patient-specific engineered tissue with clinically translatable potential.

Differences Among Perivascular Cells Derived from Human PSCs

Examining differences in perivascular cell types is complicated by, among other things, heterogeneities within the subtypes (Hedin and Thyberg, 1987; Kusuma and Gerecht, 2013). Two distinct vSMC phenotypes have been elucidated: synthetic and contractile (Beamish et al., 2010; Hedin and Thyberg, 1987; Wanjare et al., 2013a). Both participate in neovascularization, but synthetic vSMCs predominate in the embryo and in diseased or injured adult vessels while contractile vSMCs predominate in healthy adult vessels.

Building off of the studies above, we sought to comprehensively define differences between con-vSMCs, syn-vSMCs, and pericytes derived from a common hPSC source in order to uncover cellular and functional differences in vitro, toward the long term goal of rebuilding vasculature for therapeutic applications. For example, the quality of tissue-engineered blood vessels is dependent on the characteristics of the in vitro perivascular cells used. Current challenges of engineering blood vessels include precise mechanical requirements and tissue-specific cell types (Kumar et al., 2011). The in vitro characterization of our hPSC-derived perivascular cells may mediate the production of tissue-engineered blood vessels that have the patency and mechanical responsiveness equivalent to the native tissue (Chan-Park et al., 2009). Of clinical relevance, hiPSC-BC1 line is used as the hPSC source for our studies. BC1 is derived without viral integration and has been fully genetically sequenced (Cheng et al., 2012; Chou et al., 2011). Here we focus on differences in perivascular cells derived from BC1 cells with respect with respect to cellular characteristics, protein expression, ECM deposition and remodeling, migration, invasion and contractility.

The major function of both pericytes and vSMCs is to stabilize blood vessels and thus, both exhibit a great deal of similarities. Distinguishing between the three perivascular cells will facilitate their use in tissue engineering applications. Because pericytes are found in capillaries (<10 µm diameter) and microvessels (10-100 µm diameter), while vSMCs are found in larger vessels (>100 µm diameter), we sought to investigate methods that could elucidate similarities and differences between pericytes and vSMCs in vitro.

In addition to deriving pericytes as above, both hiPSC synvSMCs and hiPSC con-vSMCs (Wanjare et al., 2013a) have been derived. In performing direct comparisons between these perivascular cell derivatives, we observed numerous differences that enable the study of human perivascular development and functionality and may shed light on means to not only distinguish between them but also clearly define their functionality for future use in tissue regenerative strategies. A summary of key features of pericytes derived from hiPSC-BC1 is shown in Table 3.

TABLE 3

Summary of features hPSC-derived pericytes.

| Cell Type/Features | Pericytes |
|---|---|
| Morphology | Colony-like flat polygonal |

TABLE 3-continued

Summary of features hPSC-derived pericytes.

| Cell Type/Features | Pericytes |
| --- | --- |
| Proliferation rate | + |
| Cell Size | + |
| Endoplasmic Reticulum | Dilated + non-dilated |
| Markers | SMA, Calponin, NG2, PDGFβ |
| ECM mRNA expression | Collagen I<br>Collagen IV<br>Fibronectin$^{high}$<br>Laminin |
| ECM deposition | Collagen IV$^{globular}$<br>Fibronectin<br>Laminin$^{punctate}$ |
| MMPs | 2, 14 |
| Mesenchymal Differentiation | Adipogenic, Osteogenic |
| In vivo integration | Alignment<br>Circumferential-wrapping |
| Migration | ++ |
| Invasion | + |
| Contractility | −/+ |

By assessing marker expression from day 6 differentiating cells compared to derived EVCs and SMLCs, we were able to label our day 6 cells as early mesoderm, characterized by expression of CD56 and CD73. Via EVC differentiation, day 6 cells differentiate into VEcad+ and PDGFRβ+ cells (Kusuma et al., 2013); in SMLC differentiation, day 6 cells were induced to differentiate into cells positive for SMMHC, SM22, and calponin (Vo et al., 2010).

In vivo perivascular cell characteristics are dependent on the local 3-dimensional cellular environment, which is comprised of cell-cell interactions, surrounding ECM, local mechanical conditions, and chemical cues. Although endothelial-pericyte interactions have been studied extensively, pericyte-pericyte interactions are not well understood. Here we show the colony-like growth of hiPSC pericytes, suggesting that profound gap junction interactions are needed to activate contact inhibited proliferation of our hiPSC pericytes (Li et al., 2003).

The endoplasmic reticulum (ER) is a major organelle involved in cell protein synthesis. We show in vitro that hiPSC pericytes have both dilated and non-dilated ER. Expansion of the ER in mammalian cells has been reported to be necessary in order to accommodate increasing luminal content, mostly unfolded proteins, as a result of ER stress or improper ER function (Görlach et al., 2006; Schönthal 2012). Consequently, the observed ER expansion may indicate that serum deprivation activates vSMC contraction signaling while halting ER dependent protein synthesis, folding, and transport signaling; thus creating a bottleneck in the ER machinery giving rise to the dilated appearance. The proximity of mitochondria to the nucleus as well as the presence of autophagosomes in both placental and hiPSCs pericytes but not in hiPSC vSMCs may also indicate differences in the cellular machinery of pericytes.

We also found clear differences in the amount of stress fibers between the perivascular derivatives. Pericyte derivatives demonstrated the lowest levels of stress fibers per cell and had stress fibers located at the basal lateral surface. All perivascular cells expressed α-SMA in similar levels while calponin was found to be highly expressed in hiPSC pericytes, suggesting that this typical early vSMC marker may also be helpful to identify pericytes. The markers NG2 (or CSPG4) and PDGFR-β are widely utilized markers to identify pericytes; however, vSMCs also express these markers making it difficult to distinguish which cell type is actually represented (Murfee et al., 2005). NG2 has been observed to be expressed by both pericytes and vSMCs in arterioles and capillaries but not beyond post-capillaries (along venules) in rats (Murfee et al., 2005). Here we showed that con-vSMCs can be distinguished from pericytes and syn-vSMCs by colocalization of NG2 with stress fibers.

The in vitro production and expression of ECM proteins collagens I and IV and laminin differed between the perivascular derivatives. In the body, pericytes produce ECM in the subendothelial basement membrane of capillaries, while both vSMCs and pericytes produce ECM in the tunica media layer of larger blood vessels (Niland, 2009). Collagen I, a fibrillar collagen, is a substantial component of the interstitial connective tissue in contrast to collagen IV, which is present in all basal lamina, forming the basic irregular fibrous 2-D network of vasculature (Eble and Niland, 2009). Similarly, laminin is an indispensable component of the vascular basement membrane, the primary site where collagen IV and laminin form an interdependent network (Eble and Niland, 2009). We report that in vitro, hiPSC pericytes, associated with small vasculature have a greatly diminished collagen I expression compared to both hiPSC syn-vSMCs and hiPSC con-vSMCs, found in larger vessels (Shekhonin et al., 1987). Both our in vitro findings and in vivo studies illustrate that perivascular cells associated with larger vessels express more collagen I. From our in vitro study, we also observed that a morphologically distinct high density globular collagen IV expression is deposited by both hiPSC syn-vSMCs and pericytes, while a more fibrous collagen IV deposition as well as increased collagen IV expression is exhibited by hiPSC con-vSMCs. The in vitro laminin expression was different in hiPSC pericytes compared to both phenotypes of hiPSC vSMCs. hiPSC con-vSMCs had diffuse cytoplasmic expression of laminin while hiPSC pericytes had punctate expression around the cell membrane. Fibronectin was expressed and deposited by all tested perivascular cell types, with hiPSC pericytes expressing the highest fibronectin mRNA levels.

Pericytes and vSMCs have been known to express the gelatinases MMP2 and MMP9 needed to degrade basement membranes during vessel remodeling (Candelario-Jalil et al., 2009; Newby, 2006; Virgintino et al., 2007). The expression of MMP2 and MMP9 in hiPSC pericytes coincided with pericytes' close contact with basement membranes of vessels. A membrane-associated MMP, MMP14 was more greatly expressed by derived pericytes, compared to control placental pericytes. MMP14 is known for its ability to degrade various ECM proteins; thus, we had expected that control pericytes would express this MMP type more greatly given the abundance of these ECM proteins in microvessels and capillaries. We suspect the discrepancy may be due to a loss of this site-specific feature due to in vitro culture of harvested pericytes, emphasizing the advantages of derived perivascular cell types over primary cells.

Not surprisingly, only hiPSC-derived pericytes had the potential to differentiate to mesenchymal lineages, including adipogenic and osteogenic, while neither hiPSC-vSMC types could differentiate. In vivo, all transplanted perivascular cells aligned next to the host vasculature, with both pericytes and con-vSMCs occasionally wrapping the microvasculature. These differences correlated with in vivo phenotypes of these various perivascular cell types; both pericytes and con-vSMCs support vasculature in vivo and are thus closely associated with the endothelial lining, providing support. While the hiPSC pericytes migrated in response to wounding, they failed to invade through ECM toward ECs, indicative on their short-distance migratory nature. This result coincides with the fact that pericytes have a close spatial relation to ECs in vessels (Diaz-Flores et al., 2009).

In summary, these perivascular derivatives demonstrate an important building block toward not only reconstructing physiologically-relevant vasculature but also the study of developmental processes and diseases implicating these cell types. Important elements of our system are the several noted discrepancies between our in vitro results and in vivo phenotypes, alluding to the complexity of the field. Some of our study's in vitro results actually yield a more useful phenotype for engineering blood vessels, such as increased ECM production from the hiPSC derivatives compared to control cell lines; however, other discrepancies, such as lower expression of fibronectin splice variant ED-A in derived synvSMCs compared to con-vSMCs, drives the need for continued study on the derivation of specialized cell types to rebuild tissue. Additionally, studies in a three dimensional environment would allow further investigation of morphological features such as nucleic size that may better match in vivo properties.

Overall, the ability to generate human perivascular cells including contractile vSMCs, synthetic vSMCs, and pericytes with identical genetic backgrounds offers unprecedented opportunities to study the development and functionality of well-defined human perivascular derivatives from healthy and disease hiPSCs. Furthermore, by employing a viral integration-free and fully genetically sequenced hiPSC line, BC1, we anticipate that these findings hold translational importance.

Results

Pericytes and vSMCs Differ in Morphological Features and Proliferation Rates

Figure 22A:
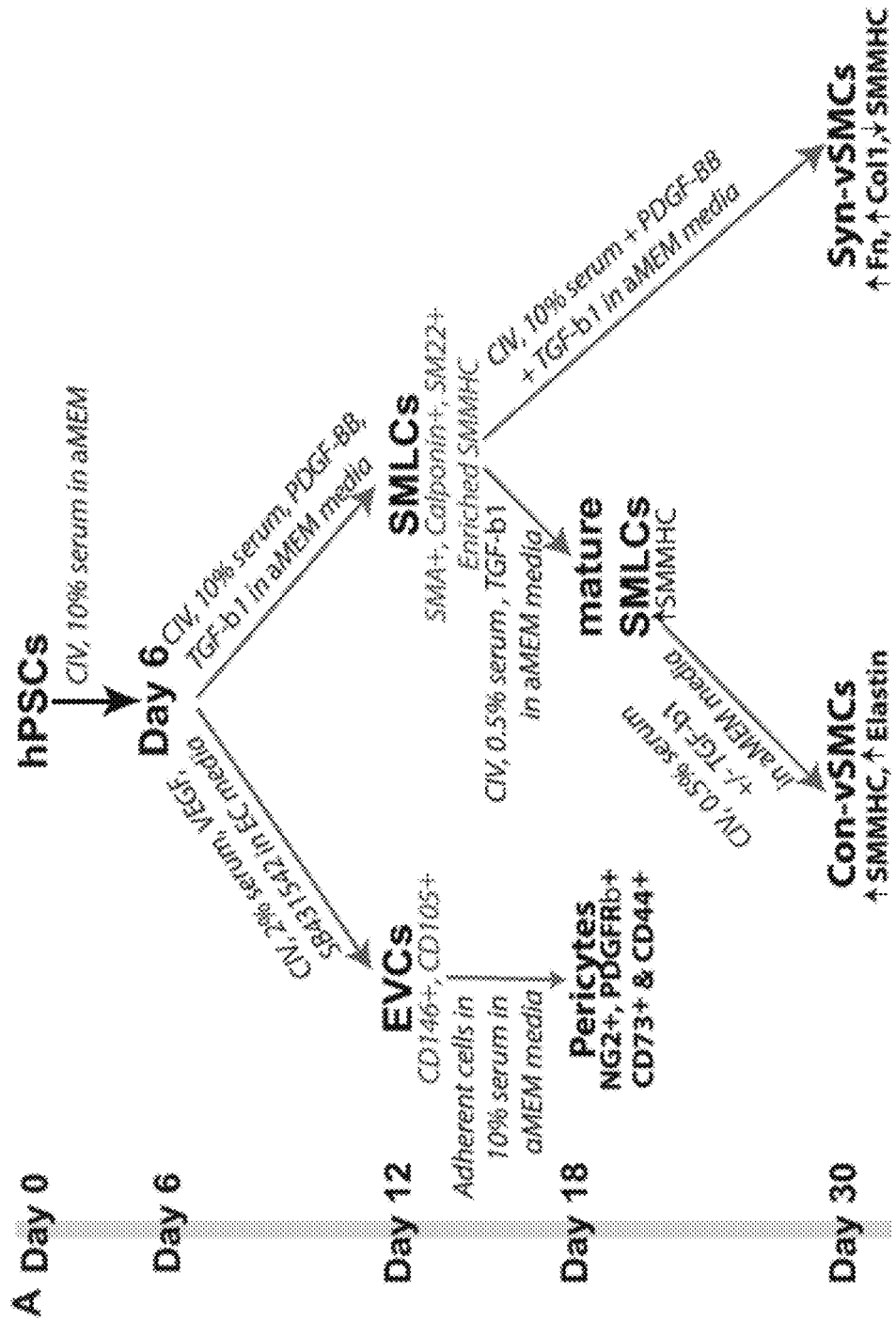
FIG. 22A-22B shows characterization of cellular properties of perivascular derivatives (A) Schema for the differentiation procedure to derive perivascular cells from hPSCs. (B) Flow cytometry analysis of day 6 differentiating cells, EVCs, and SMLCs. Isotype control in gray. Flow cytometry results shown are representative of independent experiments. CIV=collagen IV.

Perivascular cells were derived from hPSCs using differentiation protocols from previous studies (Kusuma et al., 2013; Vo et al., 2010; Wanjare et al., 2013a). Using this protocol, hPSC SMLCs subjected to long-term differentiation and in the presence of high serum and growth factors were guided toward a synthetic fate, whereas deprivation of serum and growth factors yielded a contractile fate (FIG. 1A; (Wanjare et al., 2013a). Early pericytes were derived as part of a bicellular population with early ECs named early vascular cells (EVCs) and further differentiated toward mature pericytes by a selective plating strategy (i.e. removal of collagen IV substrate and constrained adhesion time) in the presence of high serum (FIG. 22A; (Kusuma et al., 2013)). For pericytes, EVCs highly express CD105 and CD146 while pericyte derivatives express NG2, PDGF-receptor β (PDGFRβ), CD44 and CD73 (FIG. 22A; (Kusuma et al., 2013)).

Figure 22B:
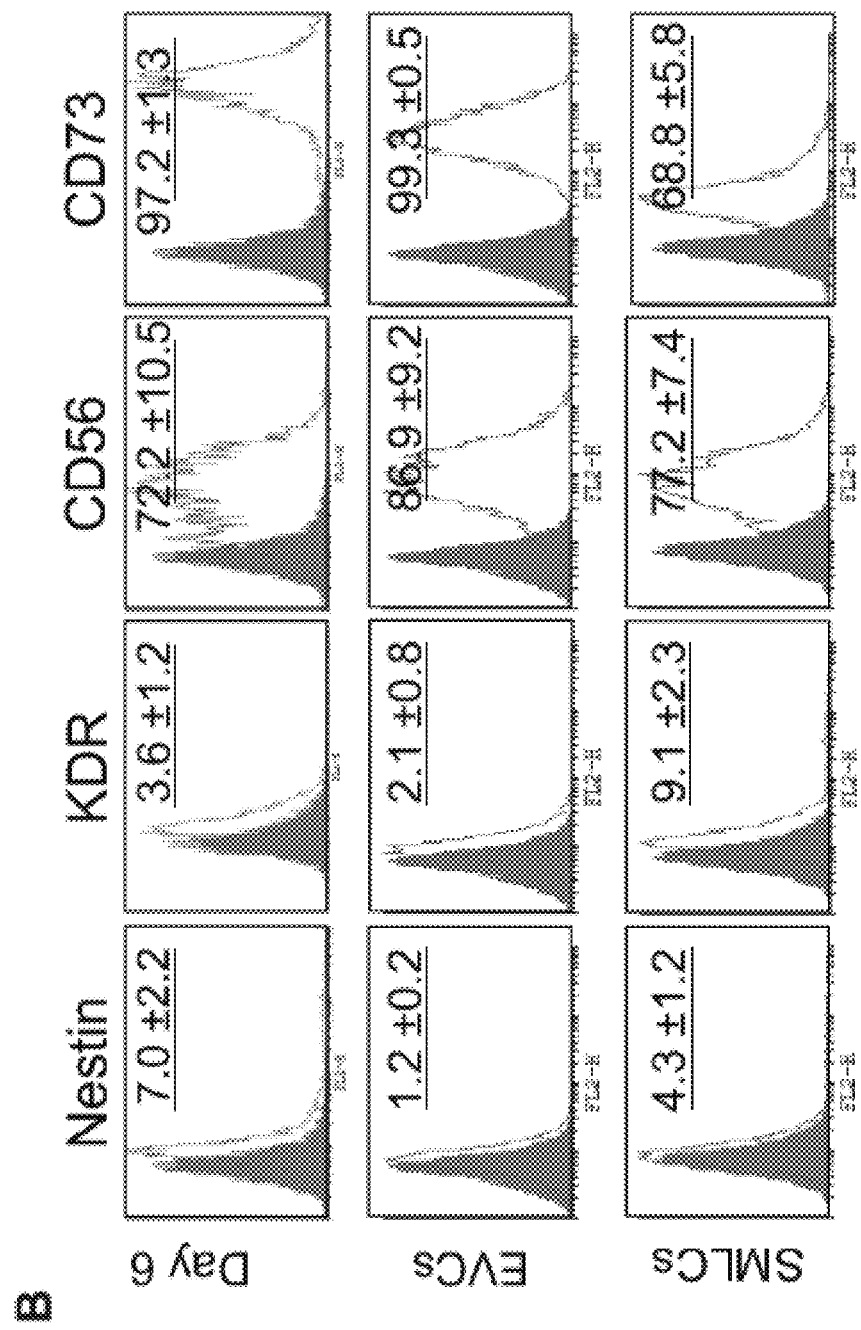

To better understand progression in differentiation, we examined marker expression at different time points along the differentiation of hPSCs. Over the first 6 days of differentiation, the three classes of perivascular cells underwent identical differentiation conditions. During embryonic development, vSMCs may arise from a number of precursors from different germ layers (Cheung et al., 2012; Majesky, 2007). We found that expression of mesodermal genes KDR, APLNR, and TCF21 increased over the first six days of differentiation in both BC1 and H9 cell lines whereas expression of neural crest markers SOX1, PAX6, and WNT1 remained stagnant (FIG. 27A). Additionally, WNT1 was not expressed in BC1 differentiating cells. These data suggest the emergence of a mesodermal population. Furthermore, our day 6 differentiating cells were assessed for the expression of markers indicative of several intermediate lineages: neuroectoderm (Nestin), lateral plate mesoderm (KDR), paraxial mesoderm (Pax1) (Cheung et al., 2012), early mesoderm (CD56) (Evseenko et al., 2010) and general mesoderm (CD73) (Boyd et al., 2009; Vodyanik et al., 2010). We found that a small fraction of day 6 differentiating cells was positive for Nestin (FIG. 22B). KDR was only slightly expressed. Pax1 was not detected via PCR or by immunofluorescence (data not shown). Mesoderm markers CD56 and CD73, however, exhibited more pronounced expression; day 6 differentiating cells were 72% positive for CD56 and >95% positive for CD73. To distinguish the subsequently derived cell populations (i.e. EVCs and SMLCs), we performed flow cytometry analysis for the aforementioned markers. After differentiation toward EVCs, we observed that Nestin expression was completely abolished; however, a small fraction of SMLCs remained Nestin+ (FIG. 22B). Similarly to day 6 differentiating cells, EVCs exhibited >95% positive expression for CD73, whereas CD73 expression decreased to ~70% in SMLCs. An important differentiator between EVCs and SMLCs is the presence of VEcad. Our previous studies demonstrated that BC1-EVCs exhibited approximately 30% VEcad+ cells (Kusuma et al., 2013). Contrastingly, we could not detect VEcad expression on SMLCs (Vo et al., 2010). A similar trend of marker expression was observed at different time points along the differentiation of hESC line H9 (FIG. 27B).

Figure 23A:
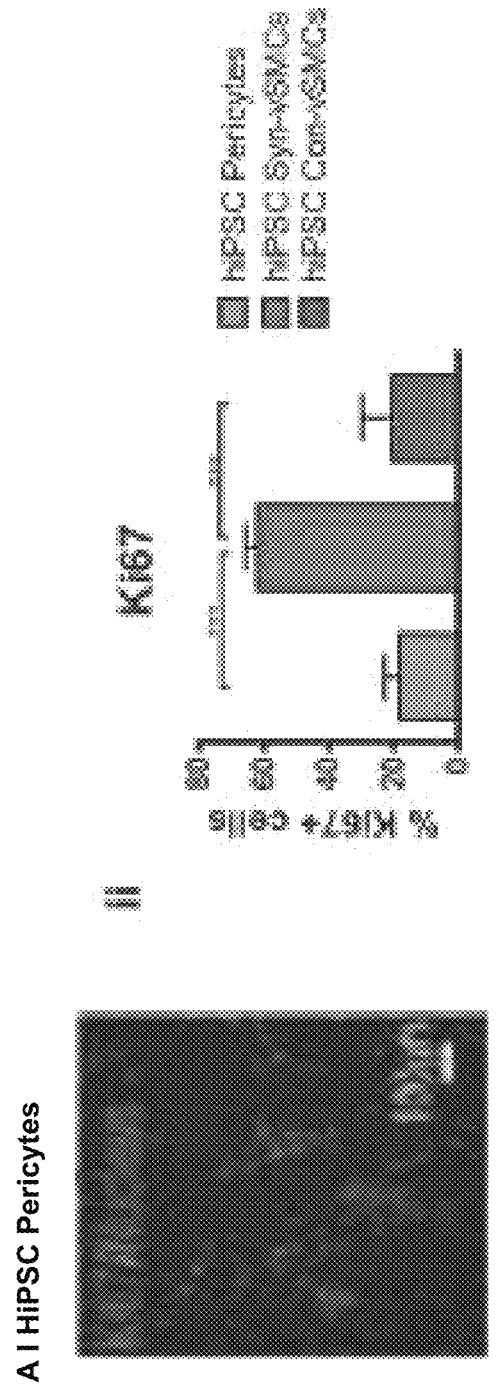

We next evaluated the differences in proliferation rates among the hPSC-derived mature perivascular cells. Although hiPSC pericytes were cultured using media containing 10% serum, they exhibited contact inhibited proliferation and grew in cell colonies (FIG. 23A-B). Next, we evaluated the morphological features after culture on 2D surfaces (FIG. 23B). hiPSC pericytes arranged themselves into colony-like structures. hiPSC con-vSMCs displayed the largest cell areas and nuclei sizes compared to hiPSC syn-vSMCs and hiPSC pericytes (FIG. 23C). Human ESC-derivatives exhibited the same trend (FIG. 27C).

Figure 23D:
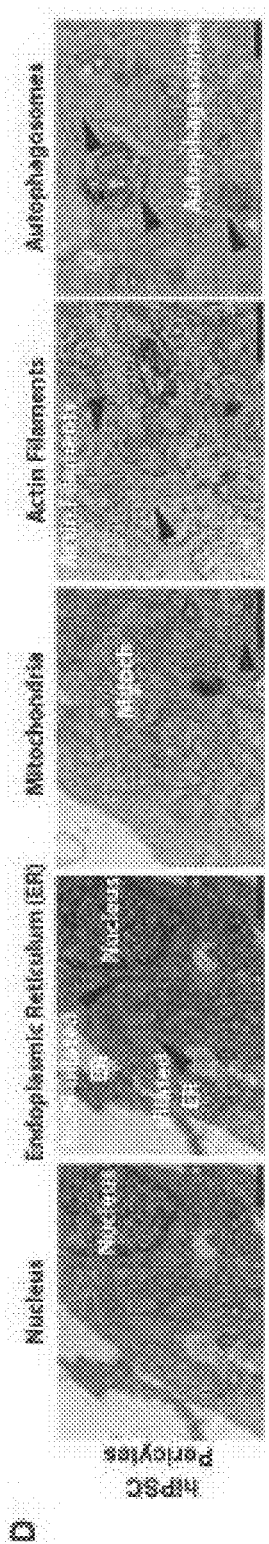
Figure 28:
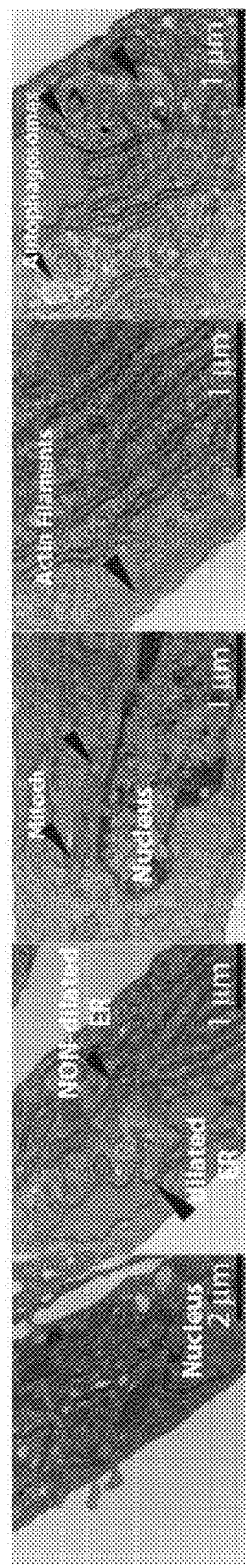
FIG. 28 shows control pericytes, related to FIG. 23. Placenta pericytes were analyzed for sub-cellular organelle organization using TEM.

There were stark differences in endoplasmic reticulum (ER), mitochondria location, stress fibers, and the presence of autophagosomes observed between pericytes and vSMCs. hiPSC pericytes (as well as cell line placental pericytes) contained both dilated and non-dilated ER (FIG. 23D; FIG. 28A). The mitochondria of hiPSC pericytes were in close proximity to the nucleus in contrast to vSMCs, whose mitochondria were located further away from the nucleus. Both hiPSC syn-vSMCs and hiPSC pericytes primarily had stress fibers located at the basal lateral surface (FIG. 23D). Pericytes also had autophagosomes present whereas both hiPSC syn-vSMCs and con-vSMCs did not (FIG. 23D; FIG. 28)

Differential Expression of Perivascular Markers

Figure 24A:
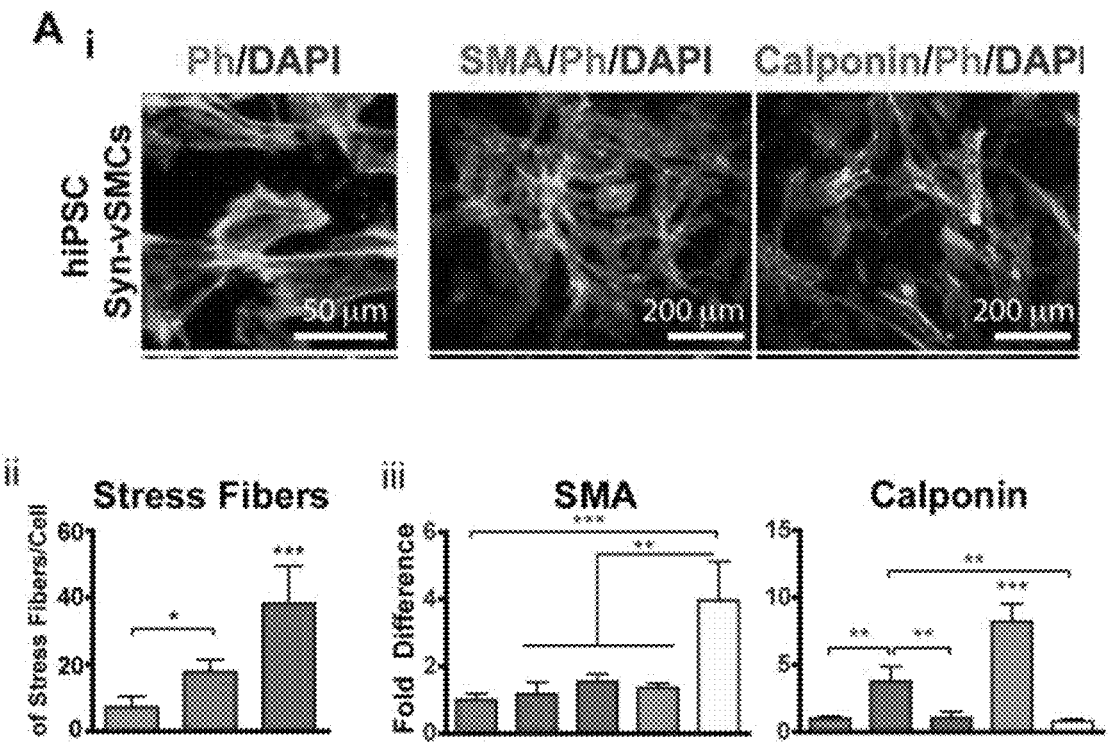
FIG. 24A-24D shows differences in stress fiber and contractile marker expression. Perivascular derivatives were assessed for (A) (i) organization of stress fibers (confocal z-stacks), αSMA, and calponin (in red; phalloidin in green; nuclei in blue); (ii) stress fiber number and (iii) αSMA and calponin expression via quantitative real time RT-PCR; (B) (i) organization of NG2 (green) and αSMA (red; nuclei in blue) and (ii) NG2 expression using quantitative real time RT-PCR; (iii) (C) (i) PDGFRβ (green), and SMMHC and (ii) PDGFRβ and SMMHC expression using quantitative real time RT-PCR; (iii) flow cytometry analysis of SMMHC; and (D) caldesmon expression via quantitative real time RT-PCR. Flow cytometry results shown are representative of independent experiments. All graphical data are reported as mean±SEM.*p<0.05, p<0.01, and *p<0.001.

We next examined the expression and localization of specific cytoskeleton proteins that have been reported to distinguish vSMCs and pericytes. Stress fibers are bundles of actin filaments that are important in mechanotransduction of adherent cells by anchoring to substrates and creating isometric tension (Deguchi et al., 2006). Perivascular cell contraction is associated with a more filamentous cytoskeleton within the cells. Accordingly, the hiPSC con-vSMCs demonstrated elevated stress fibers per cell compared to both hiPSCs syn-vSMCs and hiPSC pericytes, which had significantly lower stress fibers per cell (FIG. 24Ai-ii). While differences in α-SMA expression and organization could not be observed, calponin expression was upregulated in hiPSC pericytes (FIG. 24Ai, iii).

Figure 24B:
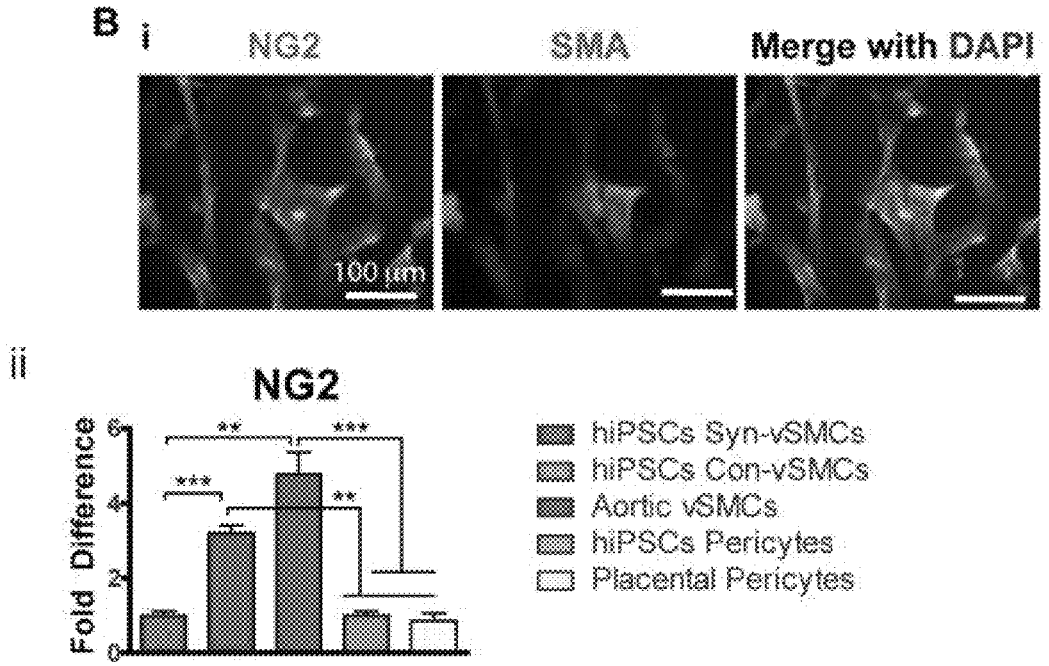

The cell surface proteins NG2 and PDGFRβ are also commonly associated with perivascular cells. The proteoglycan NG2 has been shown to be widely expressed by perivascular cells in both vasculogenic and angiogenic vasculature (Ozerdem et al., 2001). While NG2 is an appropriate marker for identifying pericytes in microvessels, it is merely a supplemental vSMC identifier considering the variety of vSMC markers (Ozerdem et al., 2001). Interestingly, profuse stress fibers were observed with the expression of NG2 protein only in hiPSC con-vSMC cultures (FIG. 24Bi). Indeed, NG2 mRNA expression in hiPSC con-vSMCs was significantly elevated compared to hiPSC syn-vSMCs and hiPSC pericytes (FIG. 24Bii). Similarly, aortic vSMCs exhibited NG2 expression with profuse stress fibers compared to placental pericytes (FIG. 24Bii; FIG. 29A). We observed differences in the expression of PDGFRβ in our hiPSC derivatives. Human iPSC con-vSMCs exhibited elevated PDGFRβ mRNA expression that had a punctuate membrane expression as well as nuclear expression (FIG. 24Ci,ii) comparable to aortic vSMCs (FIG. 29B).

Figure 24C:
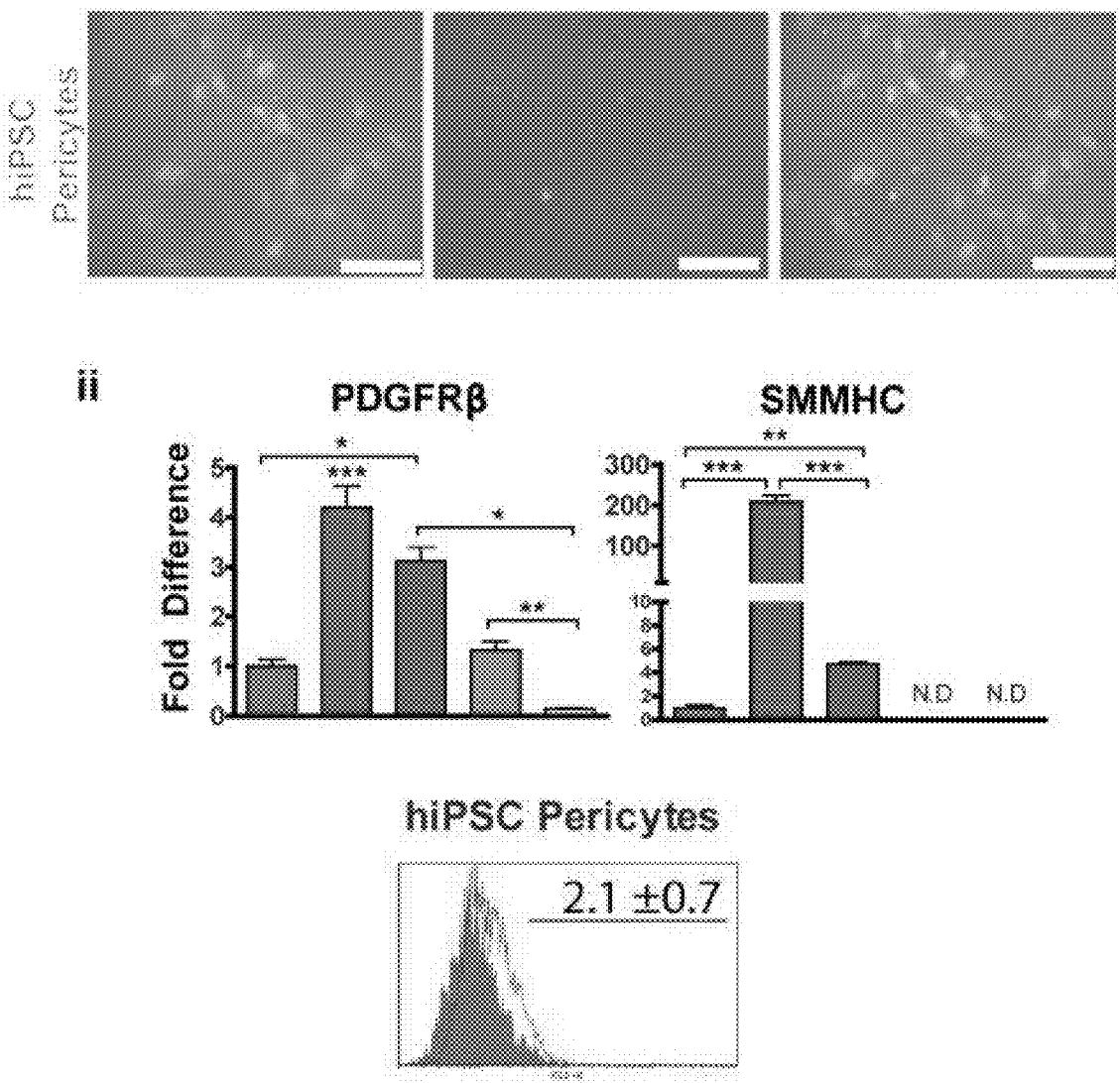
Figure 24D:
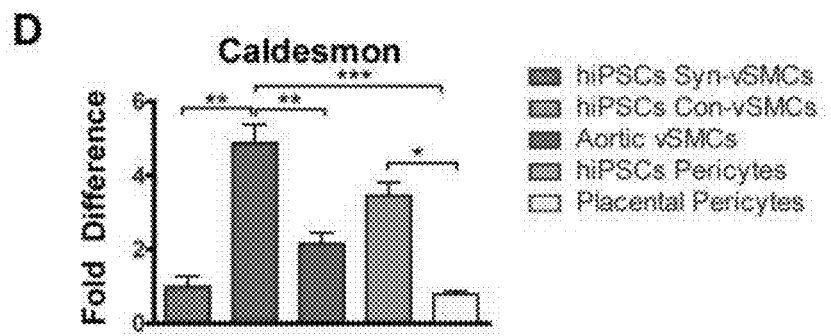
Figure 29C:
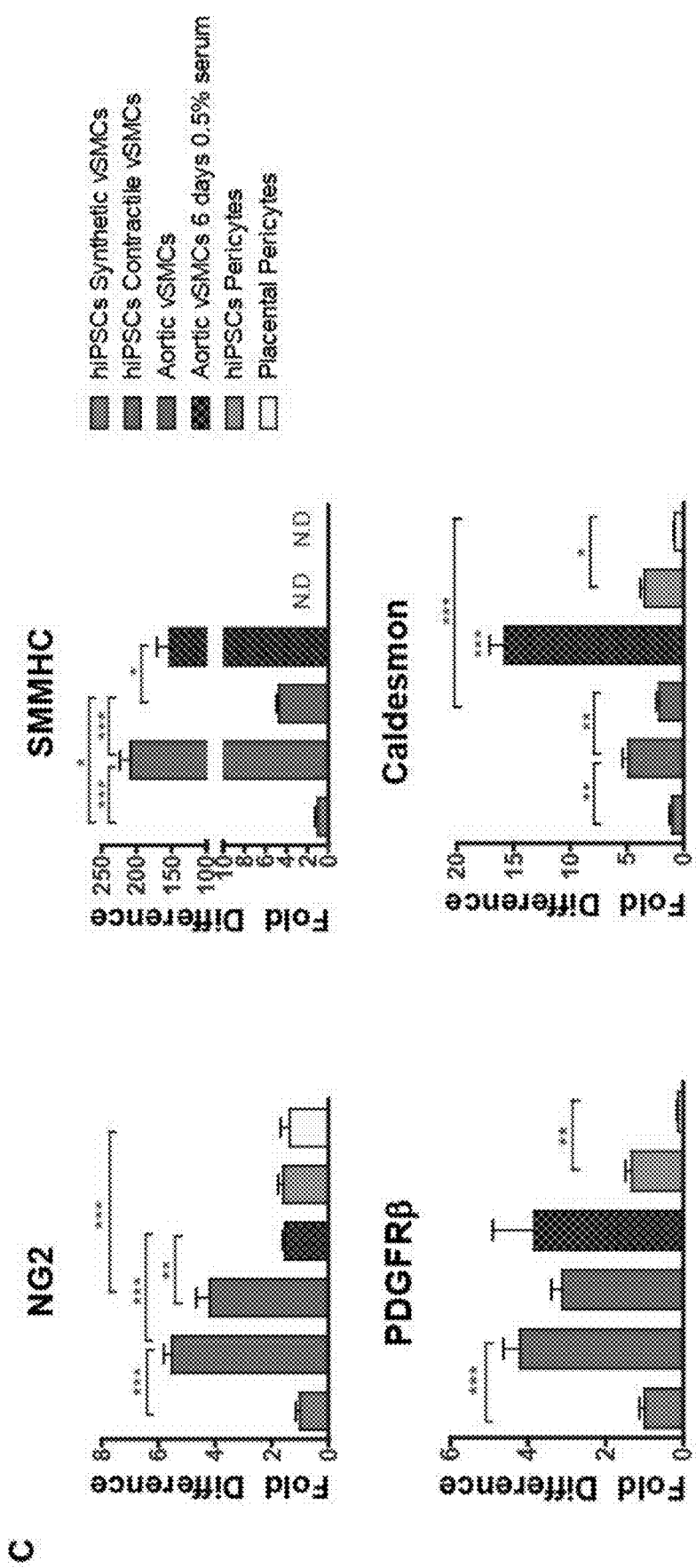

Mature vSMC marker SMMHC is associated with the contractile vSMC phenotype (Babu et al., 2000; Patel et al., 2006). Human iPSC con-vSMCs exhibited elevated SMMHC expression compared to hiPSC syn-vSMCs and pericytes (FIG. 24C). Correspondingly, aortic vSMCs exhibited elevated SMMHC expression and SMMHC stress fibers while placental pericytes did not (FIG. 24C; FIG. 29B). We further evaluated mRNA and protein expression of SMMHC on our perivascular cell derivatives. Interestingly, SMMHC was not detected in either hiPSC pericytes or control placental pericytes (FIG. 24Cii-iii). Finally, the expression of caldesmon, which plays an important role in the perivascular contraction function, was assessed in the different types of perivascular cells. We found that caldesmon was elevated in con-vSMCs compared to syn-vSMCs and pericyte derivatives (FIG. 24D). We note that the expression of perivascular markers in aortic vSMCs cultured in low serum (0.5%) conditions was slightly altered yet exhibited a similar trend of aortic vSMCs cultured in 10% serum and hiPSC con-vSMCs (FIG. 29C).

ECM Protein Production

Figure 25A:
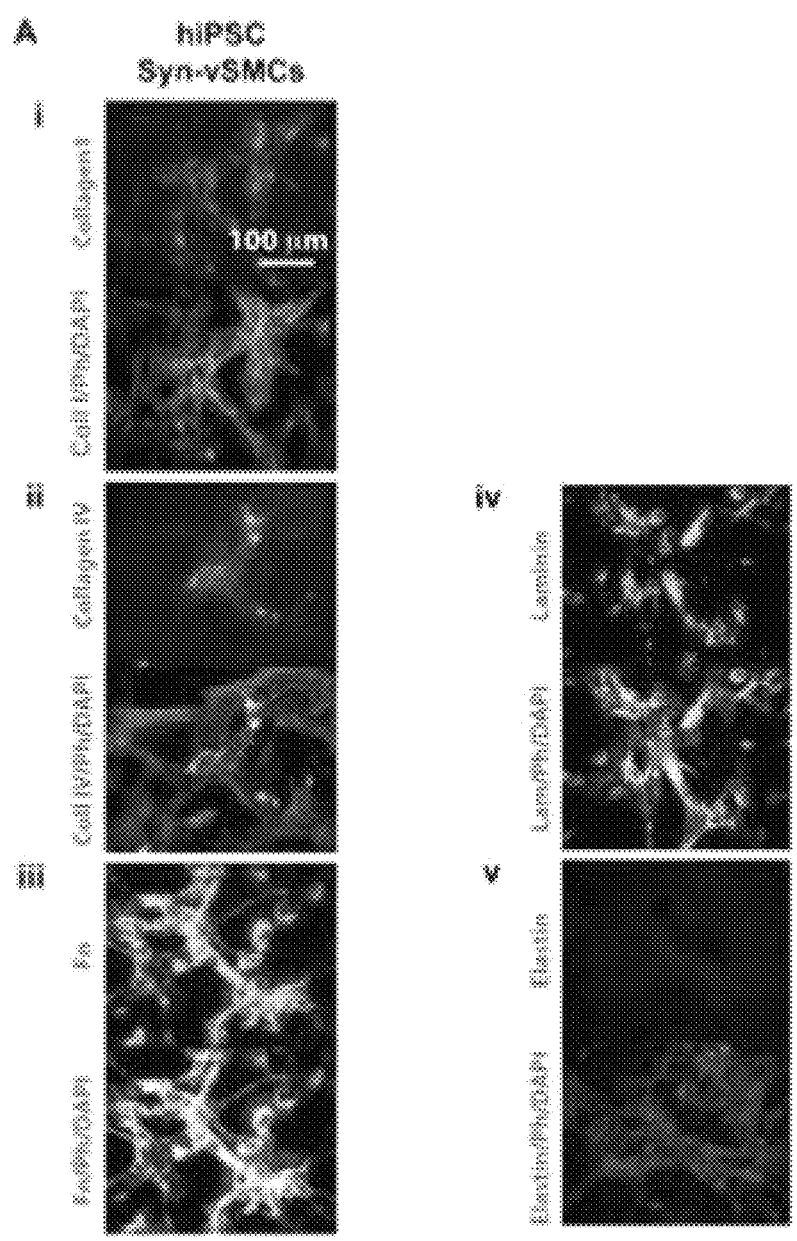
FIG. 25A-25C shows differential ECM and MMP expression by perivascular derivatives. (A) Perivascular derivatives were examined for the deposition of ECM proteins (i) collagen I, (ii) collagen IV, (iii) fibronectin, (iv) laminin, and (v) elasin after 6 days in culture and (B) their relative expression via quantitative real time RT-PCR. (C) Perivascular derivatives were compared for (i) the production of MMP2 and 9 using zymography and (ii) the relative expression MMP14 using quantitative real time RT-PCR. All graphical data are reported as mean±SEM. *p<0.05, p<0.01, and *p<0.001.
Figure 25B:
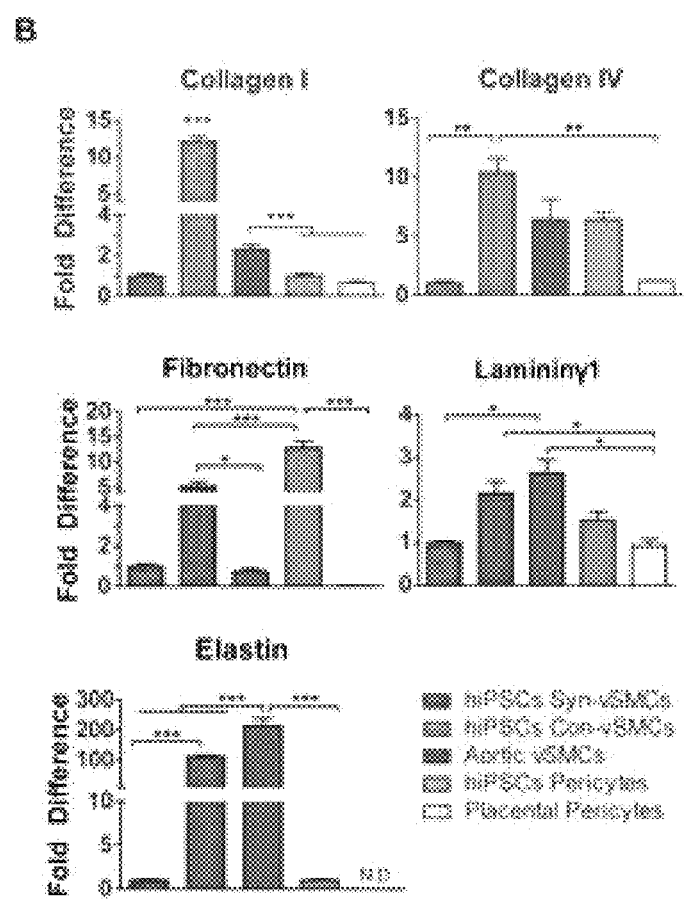
Figure 30A:
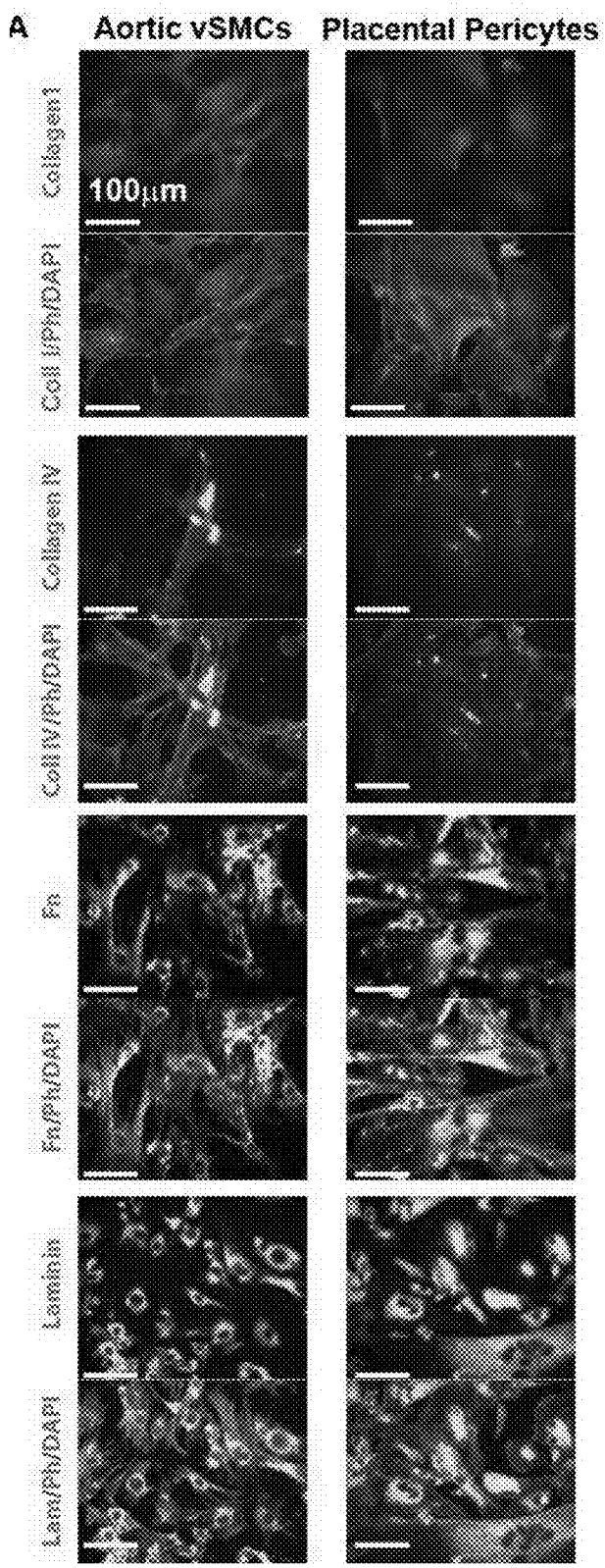

A primary function of perivascular cells is the deposition of ECM proteins to help stabilize vasculature. Because the ECM composition of various vessel types differs, we next assessed the different perivascular cell types for expression and production of ECM proteins collagen I, collagen IV, fibronectin, laminin, and elastin in vitro (FIG. 25). We found that both phenotypes of vSMCs exhibited concentrated perinuclear collagen I expression while hiPSC pericytes demonstrated diffuse expression of collagen I around the cytoplasm (FIG. 25Ai). hiPSC syn-vSMCs and hiPSC pericytes exhibited similar extracellular and globular expression of collagen IV, while hiPSC con-vSMCs had abundant fibrous intracellular and extracellular collagen IV (FIG. 4Aii). Though abundant fibronectin production was detected by hiPSC syn-vSMCs and pericytes, we observed fibronectin production was primarily intracellular (FIG. 25Aiii). Laminin appeared perinuclearly around the three perivascular derivatives (FIG. 25Aiv). However, hiPSC pericytes exhibited a punctate expression compared to the diffuse laminin protein expression in vSMC derivatives (FIG. 25Aiv). Comparable deposition of ECM proteins was observed in aortic vSMCs placental pericytes (FIG. 30A).

We could not detect elastin in either hiPSC pericytes (FIG. 25Av).

Figure 25C:
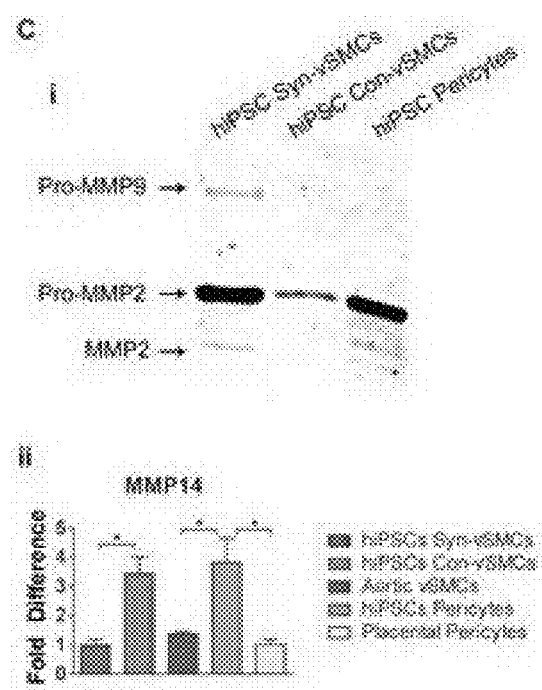

Corroborating our immunofluorescence data, we performed RT-PCR analysis on the tested perivascular cells (FIG. 25B). hiPSC-pericytes demonstrated the highest expression of fibronectin and its extra domain A (ED-A fibronectin; FIG. 30C), suggesting the propensity of the derived pericytes to produce fibronectin under amenable in vitro culture conditions. Placental pericytes exhibited lower expression of collagen IV and fibronectin compared to hiPSC pericytes (FIG. 25B; S4C). In the vasculature, there exists a wide range of matrix metalloproteinases (MMPs), which are proteolytic enzymes that degrade the ECM and remodel the architecture of associated vessels. The degradation of ECM allows perivascular cells to migrate and proliferate (Raffetto and Khalil, 2008). hiPSC pericytes produce pro-MMP2 and its active form (FIG. 25Ci). We could not detect MMP1 expression using zymography (data not shown). Molecular analysis revealed that hiPSC pericytes have greater MMP14 mRNA expression while syn-vSMCs have the lowest expression (FIG. 25Cii).

Functionality

In the body, the cellular dynamics of perivascular cells can provide information regarding whether a vessel is emergent, pathogenic, remodeling, or at a stable steady state. Of particular functional importance are multipotency, in vivo behavior, migration, invasion, and contractility of perivascular cells.

Multipotency

A major feature of pericytes is their ability to behave as mesenchymal precursors (Crisan et al., 2008). Indeed, our previous studies have demonstrated that pericyte derivatives could be differentiated to adipocytes and osteoblasts (Kusuma et al., 2013). Contrastingly, neither hiPSC con-vSMCs nor syn-vSMCs demonstrated the potential to differentiate toward adipogenic or osteogenic lineages (FIG. 26A).

In Vivo Integration

To compare in vivo functionality, we employed a Matrigel plug assay using our hiPSC perivascular cells. After one week of subcutaneous transplantation, all three types of perivascular cells aligned next to the host's growing functional vasculature, with occasional circumferential wrapping observed by con-vSMCs and pericytes (FIG. 26B), and vascular tube narrowing observed only by con-vSMCs (Kusuma et al., 2013; Wanjare et al., 2013a).

Migration

Mechanisms that induce cell motility include chemokinesis, chemotaxis, responses to interactions with ECM, and random increases such as in wound healing (Louis and Zahradka, 2010). In a wound healing assay, hiPSC pericytes and hiPSC syn-vSMCs migrated inward from the wound margin (FIG. 26Ci). Human iPSC pericytes exhibited a significant number of trajectories that were not perpendicular to the wound margin.

Invasion

Invasion is the cell motility associated with ECM degradation. To assess the ability of perivascular cells to invade toward ECs, we cultured a monolayer of ECs beneath a three-dimensional collagen gel. Each perivascular cell type was cultured atop the collagen gel and migration was measured after 48 hours. Human iPSC syn-vSMCs exhibited increased invasion toward ECs after 48 h compared to hiPSC con-vSMCs and hiPSC pericytes (FIG. 26Di), Quantification of this dynamic behavior further revealed that not only more hiPSC syn-vSMCs invaded the collagen gels compared to the other perivascular cells but also invaded to a deeper distance (FIG. 26Dii-iii).

Experimental Procedures:
Cell Culture.
All cells were cultured in humidified incubators, with atmospheres at 37° C. and 5% CO2.
hPSC Culture.
Human ESC lines H9 and H13 (passages 15 to 40; WiCell Research Institute, Madison, Wis.) and hiPSC lines MR31 (Mali et al., 2010), MMW2 (Zou et al., 2011), BC1 (Cheng et al., 2012; Chou et al., 2011), and a GFP transgenic hiPSC line (Clone 26 hCBiPS aMHCneoPGKhygro+pCAGGS2 Passage 47+10, kindly provided by Dr. Ulrich Martin, Hannover Medical School, Germany) (Haase et al., 2009) were cultured as previously described (Vo et al., 2010; Wanjare et al., 2012). Cell lines were routinely examined for pluripotent markers using immunofluorescence staining and flow cytometry analysis for TRA-1-60, TRA-1-81, SSEA4, and Oct4. See Table 1 (above) for details on the various hPSCs.

Human iPSC line BC1 (Cheng et al., 2012; Chou et al., 2011) used for Examining differences in derived perivascular cells was kindly provided by Dr. Cheng, SOM JHU and Human ESC line H9 (passages 15 to 40; WiCell Research Institute, Madison, Wis.) were grown on inactivated mouse embryonic fibroblast feeder layers GlobalStem, Rockville, Md.) in growth medium composed of 80 percent ES-DMEM/F12 GlobalStem), 20 percent knockout serum replacement (Invitrogen, Carlsbad, Calif.), and 4 ng/ml basic fibroblast growth factor (bFGF; Invitrogen) for hESCs of 10 ng/ml bFGF for hiPSCs, as previously reported (Wanjare et al., 2013). Human iPSCs were passaged every four to six days using 1 mg/ml of type IV collagenase (Invitrogen). Media were changed daily.

Control Cells.
Human v-SMCs. The control cell type used was human aorta v-SMCs (passages 4-7; ATCC, Manassas, Va.). The cells were cultured in the specified ATCC complete SMC growth medium, composed of Kaighn's Modification of Ham's F-12 Medium (F-12K Medium; ATCC), 10% or 0.5% fetal bovine serum (FBS; Hyclone), 0.01 mg/ml transferrin (Sigma-Aldrich, St. Louis, Mo.), 0.01 mg/ml insulin (Sigma), 10 mM HEPES buffer (Sigma), 10 mM 2-Tris (hydroxymethyl)methylamino)ethane-1-sulphonic acid (TES)(Sigma), 0.05 mg/ml ascorbic acid (Sigma), 10 ng/mL sodium selenite (Sigma), and 0.03 mg/ml Endothelial Cell Growth Supplement (Sigma). Human v-SMCs were passaged every three to four days using 0.25 percent trypsin (Invitrogen). Media was changed every two to three days.

Human Pericytes.
The control cell type used was human placental pericytes (passages 3-5; Promocell). The cells were cultured in the specified Pericyte Growth Media (Promocell) and were passaged every three to four days using a detachment kit (Promocell).

vSMC differentiation protocol vSMCs were derived as previously described (Wanjare et al., 2012).

Differentiation Protocol.
Human PSCs were collected through digestion with ethylenediaminetetraacetic acid (EDTA; Promega), separated into an individual cell suspension using a 40-μm mesh strainer (BD Biosciences), and plated onto collagen IV (Trevigen) coated plates at a concentration of $5 \times 10^4$ cells/$cm^2$. Cells were cultured for 6 days in a differentiation medium composed of alpha-MEM (Invitrogen), 10% FBS (Hyclone) and 0.1 mM β-mercaptoethanol (β-ME), with the media changed daily. On day 6, differentiated cells were collected through digestion with TrypLE (Invitrogen), separated with a 40-μm mesh strainer, and seeded at a concentration of $1.25 \times 10^4$ cells/$cm^2$ on collagen-type-IV-coated plates in endothelial cell growth media (ECGM) (PromoCell) supplemented with 2% FBS, 50 ng/ml VEGF with or without 10 μM SB431542 (Tocris), or 1 ng/ml VEGF+10 μM SB431542, as described in the text for 6 days. Media was changed every other day. To elucidate whether serum-free conditions could be used to derive EVCs, we followed the aforementioned protocol except differentiating the cells in alpha-MEM media supplemented with 20% knockout serum replacement, 0.1 mM β-ME, 1× non-essential amino acids (Gibco), and 1× L-glutamine (Invitrogen) for 6 days, followed by 6 days in ECGM base media (Promocell) supplemented with 50 ng/ml VEGF, 10 μM SB431542, 10% knockout serum replacement, β-ME, essential amino acids, and glutamine. These conditions were used only where specified in the text.

Flow Cytometry.
Flow cytometry was performed as previously described (Kusuma et al., 2012). Briefly, cells were incubated with FITC- or PE-conjugated antigen specific antibodies for markers (see Table 2 for antibody types and sources) and as otherwise outlined in the text including KDR-PE (1:10; BD), Nestin-PE (1:10; BD), CD56-PE (1:10; BD); SMMHC-PE (1:10; MYH11; Santa Cruz). To detect SMMHC –PE, cells were fixed with 3.7% formaldehyde for 10 minutes, washed, incubated with 0.1% Triton X for 10 minutes, washed, and finally incubated with SMMHC-PE for 45 minutes. All analyses were done using corresponding isotype controls. Forward versus side light scatter plots were used to exclude dead cells. User guide instructions were followed to complete the flow cytometry analysis via Cyflogic v1.2 software.

TABLE 2

| Antibody | Source | Catalog # | Purpose | Host Species & Reactivity | Concentration |
| --- | --- | --- | --- | --- | --- |
| AcLDL | Invitrogen | L-3484 | IF | ECs | 10 μg/ml |
| Alexa Fluor 488 | Invitrogen | A11008 | IF | Goat anti-rabbit | 1:1,000 |
| Calponin | Dako | M3556 | IF | Mouse anti-human | 1:100 |
| CD105-PE | eBioscience | 12-1057-41 | FC | Mouse anti-human | 1:10 |
| CD146-PE | BD | 550315 | FC | Mouse anti-human | 1:10 |
| CD31 | Dako | M0823, clone JC70/A | IF; IHC | Mouse anti-human | 1:200; 1:50 |
| CD31-PE | BD | 555446 | FC | Mouse anti-human | 1:10 |
| CD44-PE | BD | 550989 | FC | Mouse anti-human | 1:10 |
| CD45-PE | BD | 555483 | FC | Mouse anti-human | 1:10 |
| CD73-PE | eBioscience | 12-0739-41 Clone AD2 | FC | Mouse anti-human | 1:10 |
| Cy3 | Sigma | C2181-1ML | IF | Sheep anti-mouse | 1:50 |
| Dapi | Roche | 10236276 | IF | Nucleus | 1:1,000 |
| eNOS | BD | 610297 | IF | Mouse anti-human | 1:100 |
| FITC | Sigma | F2883 | IF | Sheep anti-mouse | 1:50 |

TABLE 2-continued

| Antibody | Source | Catalog # | Purpose | Host Species & Reactivity | Concentration |
|---|---|---|---|---|---|
| IgG-Alexa Fluor 488 | eBioscience | 53-4724-80 Clone eMB2a | FC | Mouse IgG Isotype control | 1:10 |
| IgG-FITC | BD | 554679 | FC | Mouse IgG Isotype Control | 1:10 |
| IgG-PE | BD | 555749 | FC | Mouse IgG Isotype Control | 1:10 |
| HRP-secondary | Dako | K4063 | IHC | HRP polymer anti-mouse | 1:1 |
| NG2 | Santa Cruz | sc-53389 | IF; IHC | Mouse anti-human | 1:100 |
| NG2-Alexa Fluor 488 | eBioscience | 53-6504-82 Clone 9.2.27 | FC; IF | Mouse anti-human | 1:10; 1:100 |
| PDGFRβ | Santa Cruz | SC-432 | IF | Rabbit anti-human | 1:100 |
| PDGFRβ-PE | R&D | FAB1263P | FC | Mouse anti-human | 1:10 |
| Tra-1-60-FITC | BD | 560380 | FC | Mouse anti-human | 1:10 |
| Tra-1-81-FITC | BD | 560194 | FC | Mouse anti-human | 1:10 |
| Ulex lectin | Vector Lab | FL-1061 | IF | Human ECs | 1:50 |
| VEcad | Santa Cruz | sc-9989 | IF | Mouse anti-human | 1:200 |
| VEcad-FITC | BD | 560411 | FC | Mouse anti-human | 1:10 |
| VEcad-PE | BD | 560410 | FC | Mouse anti-human | 1:10 |
| VEGFR2-PE | BD | 560494 | FC | Mouse anti-human | 1:10 |
| vWF | Dako | M0616 Clone F8/86 | IF | Mouse anti-human | 1:200 |

Real-Time Quantitative RT-PCR.

Two-step reverse transcription polymerase chain reaction (RT-PCR) was performed on differentiated and undifferentiated (day 0) hPSCs as previously described in accordance with Applied Biosystems' instructions (Kusuma et al., 2012). For each primer set (VEcad, CD31, eNOS, PDGFRβ, NG2, SMMHC, Tuj1, peripherin, ICAM), the comparative computerized tomography method (Applied Biosystems) was used to calculate the amplification differences between different samples. The values for experiments were averaged and graphed with standard deviations.

Zymography.

Zymography was performed to determine MMP activities as previously (Hanjaya-Putra et al., 2012). MMP1 was detected using SDS-Page casein zymography while both MMP2 and MMP9 were detected using SDS-Page gelatin zymography. Cells were cultured in serum free media for 72 hours. We collected the media of each sample and loaded the media of the samples per well into either a casein gel (BioRad) or gelatin gel (BioRad). Quantification of protein was done using the Bradford Assay. After electrophoresis, the gels were renatured by washing in renaturation buffer (Invitrogen) and incubated at 37° C. in denaturation buffer (Invitrogen) for 24 h. The proteins were fixed in 50% methanol and 10% acetic acid for 30 min and then stained in 0.02% commasie blue (Sigma). Gels were destained in 20% methanol and 10% acetic acid and were visualized using the ChemiDoc XRS+ System (BioRad). Images were acquired using BioRad Quantity One software.

Immunofluorescence.

Cells were prepared for immunofluorescence as previously described (Kusuma et al., 2012; Wanjare et al., 2012). Briefly, fixed cells were blocked in 1% BSA, treated with 0.1% Triton-X (Sigma), and incubated with the antigen specific antibodies for the markers in Table 2, followed by an appropriate secondary antibody, and DAPI (Roche Diagnostics) to label nuclei. For other markers, cells were fixed using 3.7% formaldehyde fixative for 15 minutes, washed with phosphate buffered saline (PBS), blocked with 1% bovine serum albumin (BSA) in PBS for 1 hour minimum, permeabilized with a solution of 0.1% Triton-X (Sigma) for ten minutes, washed with PBS, and incubated for one hour with anti-human SMA (1:200; Dako, Glostrup, Denmark), anti-human NG2 (1:100; Santa Cruz), anti-human PDGFRβ (1:100, Santa Cruz), and anti-human SMMHC (3:100; Dako). For ECM staining, cells were incubated with anti-human fibronectin (1:200; Sigma), anti-human collagen1 (1:200; Abcam), anti-human collagen IV (1:100; Abcam), anti-human laminin (1:200; Abcam) or anti-human elastin (3:100 Abcam) for one hour. Cells were rinsed twice with PBS and incubated with Alexa 546 conjugated phalloidin (1:100; Molecular Probes, Eugene, Oreg.) or anti-mouse IgG Cy3 conjugate (1:50; Sigma), anti-mouse FITC (1:50; Sigma), or anti-rabbit IgG Alexa Fluor 488 conjugate (1:1000; Molecular Probes, Eugene, Oreg.) for one hour, rinsed with PBS, and incubated with DAPI (1:1000; Roche Diagnostics) for ten minutes. Coverslips were rinsed once more with PBS and mounted with fluorescent mounting medium (Dako).

The immunolabeled cells were examined using fluorescence microscopy (Olympus BX60; Olympus, Center Valley, Pa.) and confocal microscopy (LSM 510 Meta; Carl Zeiss).

Cellular Characterizations.

The nuclei size of cells was quantified in ImageJ by thresholding fluorescence intensities of DAPI. The cellular area was quantified by thresholding the fluorescent intensities of the membrane dyes FM464. At least three fields of view were imaged at 10× for each sample. The percentage of replicating cells was quantified in ImageJ by taking the ratio between the number of Ki67 fluorescent positive cells and the fluorescent DAPI. At least three fields of view were imaged at 10× for each sample.

Transmission Electron Microscopy (TEM).

Differentiated cells, placental pericytes, and aortic vSMCs were prepared for TEM analysis as described previously (Hanjaya-Putra et al., 2011). Serial sections were cut, mounted onto copper grids, and viewed using a Phillips EM 410 TEM (FEI, Hillsboro, Oreg., USA). Images were captured using a SIS Megaview III CCD (Lakewood, Colo., USA).

Stress Fiber Quantification.

The number of stress fibers per cell was quantified using line intensity profiles of cells in ImageJ (Wei et al., 2011). Stress fibers were labeled with fluorescent Alexa-488 phalloidin and imaged at 20× and 40×. A line intensity profile across a single cell was generated with each peak representing a single stress fiber.

EC Maturation.

On day 12, derived EVCs were either sub-cultured in differentiation medium or sorted for VEcad+ cells. For the latter, EVCs were collected through digestion with Magnetic Activated Cell Sorting (MACS) buffer (0.5M EDTA and 1% BSA in PBS), incubated with 10 ul anti-human, PE-conjugated VEcad (BD) in MACS buffer for 45 minutes on ice, washed, incubated with 20 ul anti-PE microbeads (Miltenyi Biotec) in 80 ul MACS buffer for 15 minutes at 4° C., and washed twice. Cells were re-suspended in 500 µl MACS buffer and separated using a MS MACS separation column (Miltenyi Biotec). VEcad enrichment or depletion was confirmed by flow cytometry. Sorted cells were cultured on collagen-type-IV-coated dishes for an additional 6 days in ECGM supplemented with 50 ng/ml VEGF and 10 µM SB431542. Media was changed every other day.

Dil-Labeled Ac-LDL Uptake.

Derived ECs were incubated with 10 µg/ml Dil-labeled Ac-LDL (Invitrogen) for 4 hours at 37° C., rinsed three times with PBS, fixed with 4% paraformaldehyde for 30 minutes, and visualized using a fluorescence microscope (Olympus).

Tumor Necrosis Factor Alpha (TNF-α) Activation.

A previously established protocol for the activation of ECs was used (Dickinson et al., 2010). Briefly, cultured cells were stimulated for 24 hours with 10 ng/ml tumor necrosis factor-alpha (TNF-α; R&D) or blank as a control and analyzed for ICAM (Applied Biosystems).

Matrigel Cord Formation.

Cells were labeled with PKH-26 (red) according to the manufacturer's protocol. Briefly, cells were mixed with diluents C and PKH-26 for 5 minutes. The reaction was stopped by adding Hyclone FBS and the cells were washed three times. Cells were observed for their ability to form cord structures on Matrigel (BD Bioscience) as previously described (Ferreira L S, et al. (2007)). Briefly, Matrigel was cast into µ-Slide Angiogenesis wells (iBidi, Munich, Germany). After polymerization, 20,000 PKH-stained cells were seeded per well. Visualization and image acquisition were performed using fluorescence microscopy (Olympus BX60) after 24 hours.

Pericyte Maturation.

We followed a published protocol for pericyte maturation (Orlidge and D'Amore, 1987). On day 12, derived EVCs were collected through digestion with TrypLE and re-plated on tissue culture treated 6 well plates in media comprised of DMEM and 10% FBS. After 2-3 hours, unattached cells were removed and media was replaced. Cells were cultured for 6 days, changing the media every second day.

Mesenchymal Differentiation (Adipogenic and Osteogenic).

For adipogenic differentiation (Pittenger et al., 1999), we cultured derived pericytes at 10,000 cells/cm$^2$ in media comprised of DMEM, 10% FBS, 1% Penicillin/Streptomycin, 200 µM Indomethacin, 500 µM 3-Isobutyl-1-methyl xanthine (IBMX), and 5 µg/ml Insulin (all from Sigma) for 4 weeks. To assess adipogenic potential, cells were fixed with 3.7% formaldehyde, and then dehydrated with 60% isopropanol for 5 minutes. Cells were incubated with Oil Red 0 (Sigma) at 1.8 mg/ml in 60/40 isopropanol/DI H$_2$O, for 10 minutes and imaged using an inverted light microscope (Olympus).

For osteogenic differentiation (Grayson et al., 2010), we cultured derived pericytes at 5,000 cells/cm$^2$ in media comprised of low glucose DMEM, 10% FBS, 1% Penicillin/Streptomycin, 10 mM β-glycerophosphate, 100 nM dexamethasone, and 50 µM ascorbic acid (all from Sigma) for 2 weeks. Media were prepared fresh weekly. To assess osteogenic potential, samples were fixed with 3.7% formaldehyde, and washed with DI H$_2$O. Samples were incubated with Alizarin Red S (40 mM in DI H$_2$O, pH ~4.2; Sigma) for 10-20 minutes.

Collagen Gel Assay.

Collagen gels (7.1 mg/ml, BD Biosciences) were prepared as previously described (Abaci et al., 2011). EVCs, VEcad+, or VEcad− cells were encapsulated at a density of 2 million cells/ml.

Alternatively, Stock solution was used to prepare collagen gels at a density of 2.5 mg/ml, as previously described in the literature. Gel formation was achieved by simultaneously decreasing the solution's pH and increasing the temperature to 37° C. To prepare 1 ml of 2.5 mg/ml collagen gel, we added 2 million derived cells (EVCs, VEcad+ cells, or VEcad− cells) resuspended in 200 ul M199 [1×] to a mixture of 39 µl M199 [10×]+400.6 µl M199 [1×]. To this, we added 350 µl Collagen Type I. After the addition of approximately 10 µl of 1M NaOH, the solution was thoroughly mixed and transferred to wells of a 96 well plate.

In either case, ECGM supplemented with 50 ng/ml VEGF was added to the gels after 30 minutes at 37° C. in a CO$_2$ incubator. Visualization and image acquisition were performed using an inverted light microscope (Olympus).

HA Gels.

Acrylated hyaluronic acid (AHA) hydrogels were prepared as previously reported (Hanjaya-Putra et al., 2011; Khetan and Burdick, 2010; Khetan et al., 2009). Briefly, AHA was synthesized using a two-step protocol: (1) the tetrabutylammonium salt of HA (HA-TBA) was formed by reacting sodium hyaluronate (64 kDa; Lifecore Biomedical, Chaska, Minn.) with the highly acidic ion exchange resin Dowex-100 and neutralizing with 0.2 M TBA-OH; (2) acrylic acid (2.5 Eq) was coupled to HA-TBA (1 Eq, repeat unit) in the presence of dimethylaminopyridine (DMAP; 0.075 Eq) and di-tert-butyl dicarbonate (1.5 Eq) in DMSO, followed by dialysis and lyophilization. $^1$H NMR was used to confirm the final percent modification of the AHA.

Derived EVCs were encapsulated in HA hydrogels at a density of 4×10$^6$ cells/ml and cultured for up to three days in endothelial growth media 2 (EGM2; Lonza). Visualization and image acquisition were performed using an inverted light microscope (Olympus) and a confocal microscope (LSM 510 Meta; Carl Zeiss, Inc.) along the culture. We performed FM-464 vacuole staining (Invitrogen) following the manufacturers protocol (Hanjaya-Putra et al., 2011). To test parallel differentiation, EVCs were also cultured in adherent culture in EGM 2 (Lonza) for 3 days with media changed daily.

Peptides. The cell adhesive peptide GCG*YGRGDS*PG (MW: 1025.1 Da; bold italics indicates the RGD integrin-binding domain) and matrix metalloproteinases (MMP) sensitive crosslinker GCRDGPQG↓IWGQDRCG (MW: 1754.0 Da; down arrow indicates the site of proteolytic cleavage) were obtained from GenScript Corporation (Piscataway), all with more than 95 percent purity (per manufacturer high-performance liquid chromatography analysis).

EVC, sorted VE-Cad+ and sorted VE-Cad− subpopulation encapsulation and culture. AHA polymer (3 wt %) was dissolved in a sodium phosphate buffered saline (NaPBS buffer: 0.1 M sodium phosphate, 0.3 M total osmolarity, pH 8.0. The cell adhesive peptides (RGDS; GenScript) were dissolved in NaPBS buffer and added to the AHA solution at final peptide concentration of 3.7 mM and allowed to react for one hour with gentle shaking. Recombinant human VEGF165 (Pierce), bFGF (Invitrogen), Ang-1 (R&D), tumor necrosis factor-alpha (TNF-α; R&D) and stromal cell-derived factor-1 (SDF-1; R&D) were added at 50 ng/ml into the AHA-RGDS mixture. Derived EVCs or sorted subpoluations were encapsulated in HA hydrogels at a density of 4×106 cells/ml. Following the resuspension of cells, the MMP solution was added at 4.83 mM (corresponding to the 25 percent of available acrylate groups within the 3 wt % AHA). Immediately after adding the MMP crosslinker, 40 μl of this mixture was pipetted into sterile molds (5 mm diameter, 2 mm height) and allowed to react for 15 minutes at room temperature inside the laminar flow hood. The formed constructs were cultured for up to three days in endothelial growth media 2 (EGM2; Lonza). Visualization and image acquisition were performed using an inverted light microscope (Olympus) and a confocal microscope (LSM 510 Meta; Carl Zeiss) at various times during culture. We performed FM-464 vacuole staining (Invitrogen) following the manufacturers protocol. To test parallel differentiation, day 12 EVCs were also cultured in adherent culture in EGM 2 (Lonza) for 3 days with media changed daily.

Subcutaneous Implantation of Cells.

Except for GFP-hiPSC derived cells, all other PSC-derived cells were labeled with PKH-26 (red) according to the manufacturer's protocol and as previously (Wanjare et al., 2012). PKH-26 labeled cells, which were re-suspended with Matrigel (BD Biosciences) and 50 ng/ml bFGF or engineered vascular networks in HA gels for 3 days were implanted subcutaneously into nude 6-8 week old female mice in quadruplicate. To visualize angiogenesis in the implants prior to sample removal after 2 weeks, we injected Alexa Fluor® 488 (or, in some instances, Alexa Fluor® 647) conjugated isolectin GS-IB4 from *Griffonia simplicifolia* (Invitrogen) through the tail veins of the mice (Kang et al., 2011). After 20 minutes, mice were euthanized by $CO_2$ asphyxiation and the explants were harvested and fixed in 3.7 percent formaldehyde (Sigma) and proceeded for visualization and sectioning. The Johns Hopkins University Institutional Animal Care and Use Committee approved all animal protocols.

Histology.

The fixed explants were dehydrated in graded ethanol (70%-100%), embedded in paraffin, serially sectioned using a microtome (5 μm), and stained with immunohistochemistry for anti-human CD31 (Dako) and anti-human NG2 (Santa Cruz) (Hanjaya-Putra et al., 2011; Mead et al., 2007). Mouse tissue was used as controls. Blood vessels containing human CD31 cells were counted and measured using ImageJ (NIH). We sampled a minimum of 6 images for each construct.

Wound Healing Assay.

Migration of the derived hiPSC perivascular cells was assessed using a wound healing assay (Rodriguez et al., 2005). Cells were cultured to a confluent monolayer in a 6 well plate. Cell monolayers were wounded by scratching a strip of cells with a 200 uL pipette tip. After the detached cells were removed and the cells were washed, fresh medium containing 0.5% serum was added. Cells were incubated in a humidified incubator coupled to a microscope, which took a series of images of the migration of the cells into the gap every 10 min for 24 h. Migration trajectories and speed was calculated using the MTrackJ plugin of ImageJ (NIH).

Invasion Toward ECs.

A downward invasion toward ECs assay was used to assess invasion of perivascular cells. Human umbilical vein endothelial cells (HUVECs) were seeded on 16 well detachable wells (Fisher). After 24 h, 150 ul of collagen gel was added on top of the HUVECs. Stock solution was used to prepare collagen gels at a density of 2.5 mg/ml. Gel formation was achieved by simultaneously decreasing the solution's pH and increasing the temperature to 37° C. To prepare 150 ul of collagen gels, we mixed 66.1 ul M199 1× with 6.44 ul M199 10×. To this, we added 57.8 ul collagen type I. After the addition of approximately 2 ul 1M NaOH, the solution was thoroughly mixed and added to the HUVEC monolayer. The gel was allowed to polymerize for 1 h at 37° C. in a CO2 incubator. Upon polymerization, hiPSC perivascular cells were cultured on top of the gels to allow downward invasion. After 48 h the gels were fixed using 3% gluteraldehyde for 30 min, stained with 0.1% toluidine blue dye for 15 min, and washed with distilled water. Cross-sections of the gels were imaged using Accuscope. Quantification of invasion distance into the collagen gel was performed using ImageJ.

Statistical Analysis.

Real-time RT-PCR, functionality assays and image analyses were performed in at least triplicate biological samples. Real-time RT-PCR analyses were also performed with triplicate readings. Flow cytometry was performed on at least duplicate biological samples. Statistical analyses were performed with GraphPad Prism 4.02 (GraphPad Software Inc., La Jolla, Calif.). Unpaired two-tailed t-tests and one-way ANOVA analysis and Bonferonni post tests were performed where appropriate using GraphPad Prism 4.02 (GraphPad Software Inc., La Jolla, Calif.). Significance levels were set at $*p<0.05$, $p<0.01$, and $*p<0.001$. All graphical data are reported as mean±SEM.

REFERENCES

1. Abaci, H. E., Truitt, R., Tan, S., and Gerecht, S. (2011). Unforeseen decreases in dissolved oxygen levels affect tube formation kinetics in collagen gels. American Journal of Physiology—Cell Physiology 301, C431-C440.
2. Airas, L., Hellman, J., Salmi, M., Bono, P., Puurunen, T., Smith, D. J., and Jalkanen, S. (1995). CD73 is involved in lymphocyte binding to the endothelium: characterization of lymphocyte-vascular adhesion protein 2 identifies it as CD73. The Journal of Experimental Medicine 182, 1603-1608.
3. Armulik A, Abramsson A, & Betsholtz C (2005) Endothelial/Pericyte Interactions. Circulation Research 97(6): 512-523.
4. Bardin, N., Anfosso, F., MassÃ©, J. M., Cramer, E., Sabatier, F., Bivic, A. L., Sampol, J., and Dignat-George, F. (2001). Identification of CD146 as a component of the endothelial junction involved in the control of cell-cell cohesion. Blood 98, 3677-3684.
5. Cheng, L., Hansen, Nancy F., Zhao, L., Du, Y., Zou, C., Donovan, Frank X., Chou, B.-K., Zhou, G., Li, S., Dowey, Sarah N., et al. (2012). Low Incidence of DNA Sequence Variation in Human Induced Pluripotent Stem Cells Generated by Nonintegrating Plasmid Expression. Cell Stem Cell 10, 337-344.
6. Chou, B. K., Mali, P., Huang, X., Ye, Z., Dowey, S. N., Resar, L. M. S., Zou, C., Zhang, Y. A., Tong, J., and Cheng, L. (2011). Efficient human iPS cell derivation by a non-integrating plasmid from blood cells with unique epigenetic and gene expression signatures. Cell Research 21, 518-529.

7. Crisan M, Corselli M, Chen W C, & Péault B (2012) Perivascular cells for regenerative medicine. Journal of Cellular and Molecular Medicine 16(12):2851-2860.
8. Dar, A., Domev, H., Ben-Yosef, O., Tzukerman, M., Zeevi-Levin, N., Novak, A., Germanguz, I., Amit, M., and Itskovitz-Eldor, J. (2011). Multipotent Vasculogenic Pericytes From Human Pluripotent Stem Cells Promote Recovery of Murine Ischemic Limb/Clinical Perspective. Circulation 125, 87-99.
9. Dickinson, L. E., Moura, M. E., and Gerecht, S. (2010). Guiding endothelial progenitor cell tube formation using patterned fibronectin surfaces. Soft Matter 6, 5109-5119.
10. Discher, D. E., Mooney, D. J., and Zandstra, P. W. (2009). Growth Factors, Matrices, and Forces Combine and Control Stem Cells. Science 324, 1673-1677.
11. Drukker, M., Tang, C., Ardehali, R., Rinkevich, Y., Seita, J., Lee, A. S., Mosley, A. R., Weissman, I. L., and Soen, Y. (2012). Isolation of primitive endoderm, mesoderm, vascular endothelial and trophoblast progenitors from human pluripotent stem cells. Nature Biotechnology 30, 531-542.
12. Duff, S. E., Li, C., Garland, J. M., and Kumar, S. (2003). CD105 is important for angiogenesis: Evidence and potential applications. FASEB Journal 17, 984-992.
Ferreira, L. S., Gerecht, S., Shieh, H. F., Watson, N., Rupnick, M. A., Dallabrida, S. M., Vunjak-Novakovic, G., and Langer, R. (2007). Vascular progenitor cells isolated from human embryonic stem cells give rise to endothelial and smooth muscle-like cells and form vascular networks in vivo. Circulation Research 101, 286-294.
13. Forte, A., Della Corte, A., Grossi, M., Bancone, C., Provenzano, R., Finicelli, M., De Feo, M., De Santo, L. S., Nappi, G., Cotrufo, M., et al. (2013). Early cell changes and TGF pathway alterations in the aortopathy associated with bicuspid aortic valve stenosis. Clinical Science 124, 97-108.
14. Gerecht-Nir S, Ziskind A, Cohen S, & Itskovitz-Eldor J (2003) Human Embryonic Stem Cells as an in Vitro Model for Human Vascular Development and the Induction of Vascular Differentiation. Laboratory Investigation 83(12):1811-1820.
16. Grayson, W. L., Frohlich, M., Yeager, K., Bhumiratana, S., Chan, M. E., Cannizzaro, C., Wan, L. Q., Liu, X. S., Guo, X. E., and Vunjak-Novakovic, G. (2010). Engineering anatomically shaped human bone grafts. Proceedings of the National Academy of Sciences of the United States of America 107, 3299-3304.
17. Grayson, W. L., Frohlich, M., Yeager, K., Bhumiratana, S., Chan, M. E., Cannizzaro, C., Wan, L. Q., Liu, X. S., Guo, X. E., and Vunjak-Novakovic, G. (2010). Engineering anatomically shaped human bone grafts. Proceedings of the National Academy of Sciences of the United States of America 107, 3299-3304.
18. Haase, A., Olmer, R., Schwanke, K., Wunderlich, S., Merkert, S., Hess, C., Zweigerdt, R., Gruh, I., Meyer, J., Wagner, S., et al. (2009). Generation of Induced Pluripotent Stem Cells from Human Cord Blood. Cell Stem Cell 5, 434-441.
19. Hanjaya-Putra, D., Bose, V., Shen, Y.-I., Yee, J., Khetan, S., Fox-Talbot, K., Steenbergen, C., Burdick, J. A., and Gerecht, S. (2011). Controlled activation of morphogenesis to generate a functional human microvasculature in a synthetic matrix. Blood 118, 804-815.
20. Hanjaya-Putra, D., Wong, K. T., Hirotsu, K., Khetan, S., Burdick, J. A., and Gerecht, S. (2012). Spatial control of cell-mediated degradation to regulate vasculogenesis and angiogenesis in hyaluronan hydrogels. Biomaterials 33, 6123-6131.
21. Hofmann, J. J., and Iruela-Arispe, M. L. (2007). Notch Signaling in Blood Vessels: Who Is Talking to Whom About What? Circulation Research 100, 1556-1568.
22. James, D., Nam, H. S., Seandel, M., Nolan, D., Janovitz, T., Tomishima, M., Studer, L., Lee, G., Lyden, D., Benezra, R., et al. (2010). Expansion and maintenance of human embryonic stem cell-derived endothelial cells by TGFb inhibition is Idi dependent. Nature Biotechnology 28, 161-166.
23. Kang, K.-T., Allen, P., and Bischoff, J. (2011). Bioengineered human vascular networks transplanted into secondary mice reconnect with the host vasculature and re-establish perfusion. Blood.
24. Khetan, S., and Burdick, J. A. (2010). Patterning network structure to spatially control cellular remodeling and stem cell fate within 3-dimensional hydrogels. Biomaterials 31, 8228-8234.
25. Khetan, S., Katz, J. S., and Burdick, J. A. (2009). Sequential crosslinking to control cellular spreading in 3-dimensional hydrogels. Soft Matter 5, 1601-1606.
26. Kusuma, S., Shen, Y.-I., Hanjaya-Putra, D., Mali, P., Cheng, L., and Gerecht, S. (2013). Self-organized vascular networks from human pluripotent stem cells in a synthetic matrix. Proceedings of the National Academy of Sciences.
27. Kusuma, S., Zhao, S., and Gerecht, S. (2012). The extracellular matrix is a novel attribute of endothelial progenitors and of hypoxic mature endothelial cells. FASEB Journal 26, 4925-4936.
28. Lee, G., Chambers, S. M., Tomishima, M. J., and Studer, L. (2010). Derivation of neural crest cells from human pluripotent stem cells. Nat Protocols 5, 688-701.
29. Mali, P., Chou, B. K., Yen, J., Ye, Z., Zou, J., Dowey, S., Brodsky, R. A., Ohm, J. E., Yu, W., Baylin, S. B., et al. (2010). Butyrate greatly enhances derivation of human induced pluripotent stem cells by promoting epigenetic remodeling and the expression of pluripotency-associated genes. Stem Cells 28, 713-720.
30. Mead, L. E., Prater, D., Yoder, M. C., and Ingram, D. A. (2007). Isolation and Characterization of Endothelial Progenitor Cells from Human Blood. In Current Protocols in Stem Cell Biology (John Wiley & Sons, Inc.).
31. Orlidge, A., and D'Amore, P. A. (1987). Inhibition of capillary endothelial cell growth by pericytes and smooth muscle cells. The Journal of Cell Biology 105, 1455-1462.
32. Park, S.-W., Jun Koh, Y., Jeon, J., Cho, Y.-H., Jang, M.-J., Kang, Y., Kim, M.-J., Choi, C., Sook Cho, Y., Chung, H.-M., et al. (2010). Efficient differentiation of human pluripotent stem cells into functional CD34+ progenitor cells by combined modulation of the MEK/ERK and BMP4 signaling pathways. Blood 116, 5762-5772.
33. Pittenger, M. F., Mackay, A. M., Beck, S. C., Jaiswal, R. K., Douglas, R., Mosca, J. D., Moorman, M. A., Simonetti, D. W., Craig, S., and Marshak, D. R. (1999). Multilineage potential of adult human mesenchymal stem cells. Science 284, 143-147.
34. Rodriguez, L. G., Wu, X., and Guan, J.-L. (2005). Wound-healing assay. In Cell Migration (Springer), pp. 23-29.
35. Rufaihah A J, et al. (2013) Human induced pluripotent stem cell-derived endothelial cells exhibit functional heterogeneity. American Journal of Translational Research 5(1):21-35.

36. Sainson, R. A., and Harris, A. (2008). Regulation of angiogenesis by homotypic and heterotypic notch signalling in endothelial cells and pericytes: from basic research to potential therapies. Angiogenesis 11, 41-51.
37. Stewart, K. S., Zhou, Z., Zweidler-McKay, P., and Kleinerman, E. S. (2011). Delta-like ligand 4-Notch signaling regulates bone marrow-derived pericyte/vascular smooth muscle cell formation. Blood 117, 719-726.
38. Stratman, A. N., Malotte, K. M., Mahan, R. D., Davis, M. J., and Davis, G. E. (2009a). Pericyte recruitment during vasculogenic tube assembly stimulates endothelial basement membrane matrix formation. Blood 114, 5091-5101.
39. Stratman, A. N., Saunders, W. B., Sacharidou, A., Koh, W., Fisher, K. E., Zawieja, D. C., Davis, M. J., and Davis, G. E. (2009b). Endothelial cell lumen and vascular guidance tunnel formation requires MT1-MMP-dependent proteolysis in 3-dimensional collagen matrices. Blood 114, 237-247.
470. Thomson, J. A. (1998). Embryonic stem cell lines derived from human blastocysts. Science 282, 1145-1147.
41. van der Straaten, H. M., Canninga-van Dijk, M. R., Verdonck, L. F., Castigliego, D., Borst, H., Aten, J., and Fijnheer, R. (2004). Extra-Domain-A Fibronectin: A New Marker of Fibrosis in Cutaneous Graft-Versus-Host Disease. J Investig Dermatol 123, 1057-1062.
42. Vo, E., Hanjaya-Putra, D., Zha, Y., Kusuma, S., and Gerecht, S. (2010). Smooth-muscle-like cells derived from human embryonic stem cells support and augment cord-like structures in vitro. Stem Cell Rev 6, 237-247.
43. Vodyanik, M. A., Yu, J., Zhang, X., Tian, S., Stewart, R., Thomson, J. A., and Slukvin, I. I. (2010). A mesoderm-derived precursor for mesenchymal stem and endothelial cells. Cell Stem Cell 7, 718-729.
44. Vunjak-Novakovic, G., and Scadden, David T. (2011). Biomimetic Platforms for Human Stem Cell Research. Cell Stem Cell 8, 252-261.
45. Wang L, et al. (2004) Endothelial and Hematopoietic Cell Fate of Human Embryonic Stem Cells Originates from Primitive Endothelium with Hemangioblastic Properties. Immunity 21(1):31-41.
46. Wang, Z. Z., Au, P., Chen, T., Shao, Y., Daheron, L. M., Bai, H., Arzigian, M., Fukumura, D., Jain, R. K., and Scadden, D. T. (2007). Endothelial cells derived from human embryonic stem cells form durable blood vessels in vivo. Nat Biotech 25, 317-318.
47. Wanjare, M., Kuo, F., and Gerecht, S. (2012). Derivation and maturation of synthetic and contractile vascular smooth muscle cells from human pluripotent stem cells. Cardiovascular Research 97, 321-330.
48. Wei, S., Gao, X., Du, J., Su, J., and Xu, Z. (2011). Angiogenin Enhances Cell Migration by Regulating Stress Fiber Assembly and Focal Adhesion Dynamics. PLoS ONE 6, e28797.
49. White M P, et al. (2013) Limited gene expression variation in human embryonic stem cell and induced pluripotent stem cell-derived endothelial cells. Stem Cells 31(1):92-103.
50. Yamashita J, et al. (2000) Flk1-positive cells derived from embryonic stem cells serve as vascular progenitors. Nature 408(6808):92-96.
51. Yang, L., Soonpaa, M. H., Adler, E. D., Roepke, T. K., Kattman, S. J., Kennedy, M., Henckaerts, E., Bonham, K., Abbott, G. W., Linden, R. M., et al. (2008). Human cardiovascular progenitor cells develop from a KDR+ embryonic-stem-cell-derived population. Nature 453, 524-528.
52. Zou, J., Mali, P., Huang, X., Dowey, S. N., and Cheng, L. (2011). Site-specific gene correction of a point mutation in human iPS cells derived from an adult patient with sickle cell disease. Blood 118, 4599-4608.

The following claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

The invention claimed is:

1. A bipotent cell population comprised of early endothelial cells and early pericytes, wherein said cell population is created by differentiating human pluripotent stem cells (hPSCs) and/or human induced pluripotent stem cells (hiPSCs) into early vascular cells (EVCs) in vitro, wherein 95% or more of the EVCs in said cell population are positive for vascular endothelial cadherin (VEcad+), and wherein said EVCs comprise said early endothelial cells and early pericytes.

2. The bipotent cell population of claim 1, wherein the cell population can self-organize into vascular networks in vitro.

3. The bipotent cell population of claim 1, wherein the cell population is greater than 72% positive for CD56.

4. The bipotent cell population of claim 1, wherein the cell population is greater than 95% positive for CD73.

5. The bipotent cell population of claim 1, wherein the ratio of VEcad+ derived from hPSC is in the range of $8 \times 10^4$ to $2.5 \times 10^6$ per $10^6$ hPSC.

6. The bipotent cell population of claim 1, wherein the cell population is comprised within a hydrogel.

7. The bipotent cell population of claim 6, wherein the cell population is implanted in a tissue.

* * * * *